(12) United States Patent  (10) Patent No.: US 8,192,351 B2
Fishler et al.  (45) Date of Patent: Jun. 5, 2012

(54) MEDICAL DEVICE DELIVERY SYSTEM HAVING INTEGRATED INTRODUCER

(75) Inventors: Matthew G. Fishler, Sunnyvale, CA (US); Alan R. Klenk, San Jose, CA (US); Joshua Wallin, San Jose, CA (US); Peter M. Martin, Mountain View, CA (US)

(73) Assignee: Paracor Medical, Inc., Sunnyvale, CA (US)

( * ) Notice: Subject to any disclaimer, the term of this patent is extended or adjusted under 35 U.S.C. 154(b) by 476 days.

(21) Appl. No.: 12/565,669

(22) Filed: Sep. 23, 2009

(65) Prior Publication Data
US 2010/0081867 A1  Apr. 1, 2010

Related U.S. Application Data

(63) Continuation-in-part of application No. 11/837,619, filed on Aug. 13, 2007.

(51) Int. Cl.
*A61F 2/00* (2006.01)
(52) U.S. Cl. ........................................................ 600/37
(58) Field of Classification Search .................. 600/7, 8, 600/37; 128/897, 898
See application file for complete search history.

(56) References Cited

U.S. PATENT DOCUMENTS

| | | |
|---|---|---|
| 1,682,119 A | 8/1928 | Field |
| 2,278,926 A | 4/1942 | Hartwell |
| 2,826,193 A | 3/1958 | Vineberg |
| 2,985,172 A | 5/1961 | Jones |
| 3,464,322 A | 9/1969 | Pequignot |
| 3,513,836 A | 5/1970 | Sausse |
| 3,587,567 A | 6/1971 | Schiff |
| 3,613,672 A | 10/1971 | Schiff |
| 3,789,278 A | 1/1974 | Bingham et al. |
| 3,828,119 A | 8/1974 | Warburton et al. |
| 3,966,401 A | 6/1976 | Hancock et al. |
| 3,983,863 A | 10/1976 | Janke et al. |
| 3,988,782 A | 11/1976 | Dardik et al. |

(Continued)

FOREIGN PATENT DOCUMENTS

DE  3831 540 A1  4/1989

(Continued)

OTHER PUBLICATIONS

Bencini, Adriano, M.D., The "Pneumomassage" of the Heart, *Surgery*, vol. 39, No. 3, Mar. 1956.

(Continued)

*Primary Examiner* — Samuel Gilbert
(74) *Attorney, Agent, or Firm* — Fulwider Patton LLP

(57) ABSTRACT

An apparatus for delivering a medical device onto a heart includes a housing within which is releasably disposed the medical device. The housing in one embodiment comprises inner and outer deflectors between which is delivered the medical device. Both deflectors are self-expanding. A deflector compression sheath is slidable longitudinally over the housing to a delivery position at which it moves the deflectors to a collapsed configuration. The compression sheath is retracted to a deployment position to permit the deflectors to deploy by self-expanding to their larger diameters. The outer deflector has an expanded diameter sufficient to engage the inner surface of the pericardium to hold it away from the delivery site while the second deflector guides the medical device into position over the heart while protecting the heart. In another embodiment, the housing includes only an outer deflector. The apparatus also functions as an introducer when the compression sheath is moved to the delivery or "introducer" position at which configuration, the apparatus functions as an introducer.

15 Claims, 33 Drawing Sheets

U.S. PATENT DOCUMENTS

| | | | |
|---|---|---|---|
| 4,011,947 A | 3/1977 | Sawyer | |
| 4,048,990 A | 9/1977 | Goetz | |
| 4,065,816 A | 1/1978 | Sawyer | |
| 4,108,161 A | 8/1978 | Samuels et al. | |
| 4,192,293 A | 3/1980 | Asrican | |
| 4,211,325 A | 7/1980 | Wright | |
| 4,261,342 A | 4/1981 | Aranguren Duo | |
| 4,306,318 A | 12/1981 | Mano et al. | |
| 4,372,293 A | 2/1983 | Vijil-Rosales | |
| 4,403,604 A | 9/1983 | Wilkinson et al. | |
| 4,428,375 A | 1/1984 | Ellman | |
| 4,512,471 A | 4/1985 | Kaster et al. | |
| 4,536,893 A | 8/1985 | Parravicini | |
| 4,545,783 A | 10/1985 | Vaughn | |
| 4,628,937 A | 12/1986 | Hess et al. | |
| 4,630,597 A | 12/1986 | Kantrowitz et al. | |
| 4,690,134 A | 9/1987 | Snyders | |
| 4,697,703 A | 10/1987 | Will | |
| 4,750,619 A | 6/1988 | Cohen et al. | |
| 4,821,723 A | 4/1989 | Baker, Jr. et al. | |
| 4,827,932 A | 5/1989 | Ideker et al. | |
| 4,834,707 A | 5/1989 | Evans | |
| 4,838,288 A | 6/1989 | Wright et al. | |
| 4,840,626 A | 6/1989 | Linsky et al. | |
| 4,863,016 A | 9/1989 | Fong et al. | |
| 4,878,890 A | 11/1989 | Bilweis | |
| 4,936,857 A | 6/1990 | Kulik | |
| 4,957,477 A | 9/1990 | Lundbäck | |
| 4,960,424 A | 10/1990 | Grooters | |
| 4,973,300 A | 11/1990 | Wright | |
| 4,976,730 A | 12/1990 | Kwan-Gett | |
| 5,031,762 A | 7/1991 | Heacox | |
| 5,057,117 A | 10/1991 | Atweh | |
| 5,087,243 A | 2/1992 | Avitall | |
| 5,098,369 A | 3/1992 | Heilman et al. | |
| 5,106,386 A | 4/1992 | Isner et al. | |
| 5,119,804 A | 6/1992 | Anstadt | |
| 5,131,905 A | 7/1992 | Grooters | |
| 5,150,706 A | 9/1992 | Cox et al. | |
| 5,169,381 A | 12/1992 | Snyders | |
| 5,186,711 A | 2/1993 | Epstein | |
| 5,192,314 A | 3/1993 | Daskalakis | |
| 5,197,978 A | 3/1993 | Hess | |
| 5,256,132 A | 10/1993 | Snyders | |
| 5,279,539 A | 1/1994 | Bohan et al. | |
| 5,290,217 A | 3/1994 | Campos | |
| 5,333,624 A | 8/1994 | Tovey | |
| 5,336,254 A | 8/1994 | Brennen et al. | |
| 5,344,442 A | 9/1994 | Deac | |
| 5,352,184 A | 10/1994 | Goldberg et al. | |
| 5,356,432 A | 10/1994 | Rutkow et al. | |
| 5,366,460 A | 11/1994 | Eberbach | |
| 5,383,840 A | 1/1995 | Heilman et al. | |
| 5,385,156 A | 1/1995 | Oliva | |
| 5,385,229 A | 1/1995 | Bittmann et al. | |
| 5,385,528 A | 1/1995 | Wilk | |
| 5,391,200 A | 2/1995 | KenKnight et al. | |
| 5,405,360 A | 4/1995 | Tovey | |
| 5,429,584 A | 7/1995 | Chiu | |
| 5,433,727 A | 7/1995 | Sideris | |
| 5,456,711 A | 10/1995 | Hudson | |
| 5,460,962 A | 10/1995 | Kemp | |
| 5,500,015 A | 3/1996 | Deac | |
| 5,507,779 A | 4/1996 | Altman | |
| 5,509,428 A | 4/1996 | Dunlop | |
| 5,524,633 A | 6/1996 | Heaven et al. | |
| 5,533,958 A | 7/1996 | Wilk | |
| 5,534,024 A | 7/1996 | Rogers et al. | |
| 5,545,210 A | 8/1996 | Hess et al. | |
| 5,558,617 A | 9/1996 | Heilman et al. | |
| 5,571,215 A | 11/1996 | Sterman et al. | |
| 5,582,616 A | 12/1996 | Bolduc et al. | |
| 5,584,803 A | 12/1996 | Stevens et al. | |
| 5,593,424 A | 1/1997 | Northrup, III | |
| 5,593,441 A | 1/1997 | Lichtenstein et al. | |
| 5,603,337 A | 2/1997 | Jarvik | |
| 5,607,477 A | 3/1997 | Schindler et al. | |
| 5,647,372 A | 7/1997 | Tovey et al. | |
| 5,647,380 A | 7/1997 | Campbell et al. | |
| 5,695,525 A | 12/1997 | Mulhauser et al. | |
| 5,702,343 A | 12/1997 | Alferness | |
| 5,713,954 A | 2/1998 | Rosenberg et al. | |
| 5,727,569 A | 3/1998 | Benetti et al. | |
| 5,749,839 A | 5/1998 | Kovacs | |
| 5,782,746 A | 7/1998 | Wright | |
| 5,799,661 A | 9/1998 | Boyd et al. | |
| 5,800,334 A | 9/1998 | Wilk | |
| 5,800,528 A | 9/1998 | Lederman et al. | |
| 5,814,097 A | 9/1998 | Sterman et al. | |
| 5,824,028 A | 10/1998 | Knisley | |
| 5,836,311 A | 11/1998 | Borst et al. | |
| 5,848,962 A | 12/1998 | Feindt et al. | |
| 5,849,005 A | 12/1998 | Garrison et al. | |
| 5,849,033 A | 12/1998 | Mehmanesh et al. | |
| 5,853,422 A | 12/1998 | Huebsch et al. | |
| 5,855,601 A | 1/1999 | Bessler et al. | |
| 5,865,791 A | 2/1999 | Whayne et al. | |
| 5,876,432 A | 3/1999 | Lau et al. | |
| 5,910,124 A | 6/1999 | Rubin | |
| 5,927,284 A | 7/1999 | Borst et al. | |
| 5,948,019 A | 9/1999 | Shu et al. | |
| 5,957,977 A | 9/1999 | Melvin | |
| 5,961,440 A | 10/1999 | Schweich, Jr. et al. | |
| 5,976,069 A | 11/1999 | Navia et al. | |
| 5,979,456 A | 11/1999 | Magovern | |
| 5,984,857 A | 11/1999 | Buck et al. | |
| 5,990,378 A | 11/1999 | Ellis | |
| 6,007,486 A | 12/1999 | Hunt et al. | |
| 6,015,378 A | 1/2000 | Borst et al. | |
| 6,024,096 A | 2/2000 | Buckberg | |
| 6,045,497 A | 4/2000 | Schweich, Jr. et al. | |
| 6,050,936 A | 4/2000 | Schweich, Jr. et al. | |
| 6,059,715 A | 5/2000 | Schweich, Jr. et al. | |
| 6,071,303 A | 6/2000 | Laufer | |
| 6,076,013 A | 6/2000 | Brennan et al. | |
| 6,077,214 A | 6/2000 | Mortier et al. | |
| 6,077,218 A | 6/2000 | Alferness | |
| 6,079,414 A | 6/2000 | Roth | |
| 6,095,968 A | 8/2000 | Snyders | |
| 6,110,100 A | 8/2000 | Talpade | |
| 6,117,159 A | 9/2000 | Huebsch et al. | |
| 6,117,979 A | 9/2000 | Hendriks et al. | |
| 6,123,662 A | 9/2000 | Alferness et al. | |
| 6,125,852 A | 10/2000 | Stevens et al. | |
| 6,126,590 A | 10/2000 | Alferness | |
| 6,155,968 A | 12/2000 | Wilk | |
| 6,155,972 A | 12/2000 | Nauertz et al. | |
| 6,162,168 A | 12/2000 | Schweich, Jr. et al. | |
| 6,165,119 A | 12/2000 | Schweich, Jr. et al. | |
| 6,165,120 A | 12/2000 | Schweich, Jr. et al. | |
| 6,165,121 A | 12/2000 | Alferness | |
| 6,165,122 A | 12/2000 | Alferness | |
| 6,166,184 A | 12/2000 | Hendriks et al. | |
| 6,169,922 B1 | 1/2001 | Alferness et al. | |
| 6,174,279 B1 | 1/2001 | Girard | |
| 6,179,791 B1 | 1/2001 | Krueger | |
| 6,183,411 B1 | 2/2001 | Mortier et al. | |
| 6,190,408 B1 | 2/2001 | Melvin | |
| 6,192,280 B1 | 2/2001 | Sommer et al. | |
| 6,193,648 B1 | 2/2001 | Krueger | |
| 6,206,820 B1 | 3/2001 | Kazi et al. | |
| 6,214,047 B1 | 4/2001 | Melvin | |
| 6,217,894 B1 | 4/2001 | Sawhney et al. | |
| 6,221,103 B1 | 4/2001 | Melvin | |
| 6,224,540 B1 | 5/2001 | Ledermann et al. | |
| 6,230,714 B1 | 5/2001 | Alferness et al. | |
| 6,258,023 B1 | 7/2001 | Rogers et al. | |
| 6,260,552 B1 | 7/2001 | Mortier et al. | |
| 6,261,222 B1 | 7/2001 | Schweich, Jr. et al. | |
| 6,264,602 B1 | 7/2001 | Mortier et al. | |
| 6,282,445 B1 | 8/2001 | Reinhardt et al. | |
| 6,287,250 B1 | 9/2001 | Peng et al. | |
| 6,293,906 B1 | 9/2001 | Vanden Hoek et al. | |
| 6,360,749 B1 | 3/2002 | Jayaraman | |
| 6,375,608 B1 | 4/2002 | Alferness | |
| 6,390,976 B1 | 5/2002 | Spence et al. | |
| 6,402,679 B1 | 6/2002 | Mortier et al. | |

| | | |
|---|---|---|
| 6,402,680 B2 | 6/2002 | Mortier et al. |
| 6,406,420 B1 | 6/2002 | McCarthy et al. |
| 6,409,760 B1 | 6/2002 | Melvin |
| 6,416,459 B1 | 7/2002 | Haindl |
| 6,425,856 B1 | 7/2002 | Shapland et al. |
| 6,432,039 B1 | 8/2002 | Wardle |
| 6,451,025 B1 | 9/2002 | Jervis |
| 6,482,146 B1 | 11/2002 | Alferness et al. |
| 6,517,570 B1 | 2/2003 | Lau et al. |
| 6,537,203 B1 | 3/2003 | Alferness et al. |
| 6,544,168 B2 | 4/2003 | Alferness |
| 6,547,716 B1 | 4/2003 | Milbocker |
| 6,547,821 B1 | 4/2003 | Taylor et al. |
| 6,564,094 B2 | 5/2003 | Alferness et al. |
| 6,567,699 B2 | 5/2003 | Alferness et al. |
| 6,572,533 B1 | 6/2003 | Shapland et al. |
| 6,575,921 B2 | 6/2003 | Vanden Hoek et al. |
| 6,579,226 B2 | 6/2003 | Vanden Hoek et al. |
| 6,582,355 B2 | 6/2003 | Alferness et al. |
| 6,587,734 B2 | 7/2003 | Okuzumi |
| 6,602,184 B2 | 8/2003 | Lau et al. |
| 6,612,978 B2 | 9/2003 | Lau et al. |
| 6,612,979 B2 | 9/2003 | Lau et al. |
| 6,620,095 B2 | 9/2003 | Taheri |
| 6,633,780 B1 | 10/2003 | Berger |
| 6,645,139 B2 | 11/2003 | Haindl |
| 6,663,558 B2 | 12/2003 | Lau et al. |
| 6,673,009 B1 | 1/2004 | Vanden Hoek et al. |
| 6,682,474 B2 | 1/2004 | Lau et al. |
| 6,682,475 B2 | 1/2004 | Cox et al. |
| 6,682,476 B2 | 1/2004 | Alferness et al. |
| 6,685,620 B2 | 2/2004 | Gifford, III et al. |
| 6,685,627 B2 | 2/2004 | Jayaraman |
| 6,689,048 B2 | 2/2004 | Vanden Hoek et al. |
| 6,695,769 B2 | 2/2004 | French et al. |
| 6,699,259 B2 | 3/2004 | Fogarty et al. |
| 6,701,929 B2 | 3/2004 | Hussein |
| 6,702,732 B1 | 3/2004 | Lau et al. |
| 6,723,041 B2 | 4/2004 | Lau et al. |
| 6,730,016 B1 | 5/2004 | Cox et al. |
| 6,755,779 B2 | 6/2004 | Vanden Hoek et al. |
| 6,759,431 B2 | 7/2004 | Hunter et al. |
| 6,818,018 B1 | 11/2004 | Sawhney |
| 6,833,408 B2 | 12/2004 | Sehl et al. |
| 6,846,296 B1 | 1/2005 | Milbocker et al. |
| 6,876,887 B2 | 4/2005 | Okuzumi |
| 6,881,185 B2 | 4/2005 | Vanden Hoek et al. |
| 6,887,192 B1 | 5/2005 | Whayne et al. |
| 6,893,392 B2 | 5/2005 | Alferness |
| 6,896,652 B2 | 5/2005 | Alferness et al. |
| 6,902,522 B1 | 6/2005 | Walsh et al. |
| 6,902,524 B2 | 6/2005 | Alferness et al. |
| 6,908,426 B2 | 6/2005 | Shapland et al. |
| 7,022,063 B2 | 4/2006 | Lau et al. |
| 7,077,802 B2 | 7/2006 | Lau et al. |
| 7,081,086 B2 | 7/2006 | Lau et al. |
| 7,097,613 B2 | 8/2006 | Lau et al. |
| 7,155,295 B2 | 12/2006 | Lau et al. |
| 7,158,839 B2 | 1/2007 | Lau |
| 7,189,203 B2 | 3/2007 | Lau et al. |
| 7,252,632 B2 | 8/2007 | Shapland et al. |
| 7,255,674 B2 | 8/2007 | Alferness |
| 7,261,684 B2 | 8/2007 | Alferness |
| 7,278,964 B2 | 10/2007 | Alferness |
| 2001/0029314 A1 | 10/2001 | Alferness et al. |
| 2001/0047122 A1 | 11/2001 | Vanden Hoek et al. |
| 2002/0007216 A1 | 1/2002 | Melvin |
| 2002/0019580 A1 | 2/2002 | Lau et al. |
| 2002/0022880 A1 | 2/2002 | Melvin |
| 2002/0028981 A1 | 3/2002 | Lau et al. |
| 2002/0052538 A1 | 5/2002 | Lau et al. |
| 2002/0068849 A1 | 6/2002 | Schweich, Jr. et al. |
| 2002/0077524 A1 | 6/2002 | Schweich, Jr. et al. |
| 2002/0077637 A1 | 6/2002 | Vargas et al. |
| 2002/0082647 A1 | 6/2002 | Alferness et al. |
| 2002/0091296 A1 | 7/2002 | Alferness |
| 2002/0103511 A1 | 8/2002 | Alferness et al. |
| 2002/0151950 A1 | 10/2002 | Okuzumi |
| 2003/0004547 A1 | 1/2003 | Owen et al. |
| 2003/0023296 A1 | 1/2003 | Osypka |
| 2003/0060674 A1 | 3/2003 | Gifford, III et al. |
| 2003/0060677 A1 | 3/2003 | French et al. |
| 2003/0060895 A1 | 3/2003 | French et al. |
| 2003/0065248 A1 | 4/2003 | Lau et al. |
| 2003/0125774 A1 | 7/2003 | Salo |
| 2003/0199733 A1 | 10/2003 | Shapland et al. |
| 2003/0199955 A1 | 10/2003 | Struble et al. |
| 2003/0229265 A1 | 12/2003 | Girard et al. |
| 2004/0002626 A1 | 1/2004 | Feld et al. |
| 2004/0064014 A1 | 4/2004 | Gelvin et al. |
| 2004/0102804 A1 | 5/2004 | Chin |
| 2004/0106848 A1 | 6/2004 | Lau et al. |
| 2004/0133069 A1 | 7/2004 | Shapland et al. |
| 2004/0143154 A1 | 7/2004 | Lau et al. |
| 2004/0171907 A1 | 9/2004 | Alferness et al. |
| 2004/0171908 A1 | 9/2004 | Alferness et al. |
| 2004/0210104 A1 | 10/2004 | Lau et al. |
| 2004/0230091 A1 | 11/2004 | Lau et al. |
| 2004/0267086 A1 | 12/2004 | Anstadt et al. |
| 2005/0033322 A1 | 2/2005 | Lau et al. |
| 2005/0049611 A1 | 3/2005 | Lau et al. |
| 2005/0055032 A1 | 3/2005 | Lau et al. |
| 2005/0059854 A1 | 3/2005 | Hoek et al. |
| 2005/0059855 A1 | 3/2005 | Lau et al. |
| 2005/0085688 A1 | 4/2005 | Girard et al. |
| 2005/0090707 A1 | 4/2005 | Lau et al. |
| 2005/0102010 A1 | 5/2005 | Lau et al. |
| 2005/0102016 A1 | 5/2005 | Lau et al. |
| 2005/0107661 A1 | 5/2005 | Lau et al. |
| 2005/0119717 A1 | 6/2005 | Lau et al. |
| 2005/0137673 A1 | 6/2005 | Lau et al. |
| 2005/0169958 A1 | 8/2005 | Hunter et al. |
| 2005/0169959 A1 | 8/2005 | Hunter et al. |
| 2005/0182290 A1 | 8/2005 | Lau et al. |
| 2005/0256175 A1 | 11/2005 | Lau et al. |
| 2005/0283042 A1 | 12/2005 | Meyer et al. |
| 2006/0009831 A1 | 1/2006 | Lau et al. |
| 2006/0041183 A1 | 2/2006 | Massen et al. |
| 2006/0041309 A1 | 2/2006 | Massen et al. |
| 2007/0106359 A1 | 5/2007 | Schaer et al. |

FOREIGN PATENT DOCUMENTS

| | | |
|---|---|---|
| DE | 38 31 540 C2 | 6/1993 |
| DE | 295 17 393 U1 | 3/1996 |
| EP | 0 370 931 A1 | 5/1990 |
| EP | 0 280 564 B1 | 6/1993 |
| EP | 0 590 431 A1 | 4/1994 |
| EP | 0 583 012 B1 | 7/1996 |
| EP | 0 791 330 A3 | 8/1997 |
| EP | 0812928 A1 | 12/1997 |
| EP | 0 919 193 A1 | 6/1999 |
| FR | 2 527 435 | 12/1983 |
| FR | 2 588 758 A1 | 10/1986 |
| FR | 2 645 739 | 10/1990 |
| GB | 2 115 287 A | 9/1983 |
| GB | 2 209 678 A | 5/1989 |
| JP | 60-203250 | 10/1985 |
| JP | 1-145066 | 6/1989 |
| JP | 1-271829 | 10/1989 |
| SU | 3316206/28-13 | 4/1983 |
| SU | 1734767 A1 | 5/1992 |
| WO | WO 91/19465 | 12/1991 |
| WO | WO 95/06447 | 3/1995 |
| WO | WO 96/64852 | 2/1996 |
| WO | WO 96/40356 | 12/1996 |
| WO | WO 97/20505 | 6/1997 |
| WO | WO 97/24101 | 7/1997 |
| WO | WO 98/03213 | 1/1998 |
| WO | WO 98/14136 | 4/1998 |
| WO | WO 98/26738 | 6/1998 |
| WO | WO 98/29041 | 7/1998 |
| WO | WO 98/58598 | 12/1998 |
| WO | WO 99/11201 | 3/1999 |
| WO | WO 99/30647 | 6/1999 |
| WO | WO 99/44534 | 9/1999 |
| WO | WO 99/44680 | 9/1999 |
| WO | WO 99/53977 | 10/1999 |
| WO | WO 99/56655 | 11/1999 |

| | | |
|---|---|---|
| WO | WO 00/02500 | 1/2000 |
| WO | WO 00/06026 | 2/2000 |
| WO | WO 00/06027 | 2/2000 |
| WO | WO 00/06028 | 2/2000 |
| WO | WO 00/13722 | 3/2000 |
| WO | WO 00/16700 | 3/2000 |
| WO | WO 00/18320 | 4/2000 |
| WO | WO 00/28912 | 5/2000 |
| WO | WO 00/28918 | 5/2000 |
| WO | WO/0036995 | 6/2000 |
| WO | WO 00/42919 | 7/2000 |
| WO | WO 00/45735 | 8/2000 |
| WO | WO 00/48795 | 8/2000 |
| WO | WO 00/62727 | 10/2000 |
| WO | WO 00/74769 | 12/2000 |
| WO | WO 01/17437 | 3/2001 |
| WO | WO 01/21098 | 3/2001 |
| WO | WO 01/50981 | 7/2001 |
| WO | WO 01/67985 | 9/2001 |
| WO | WO 01/85061 | 11/2001 |
| WO | WO 01/91667 | 12/2001 |
| WO | WO 01/95830 | 12/2001 |
| WO | WO 01/95831 | 12/2001 |
| WO | WO 01/95832 | 12/2001 |
| WO | WO 02/13726 | 2/2002 |
| WO | WO 02/19917 | 3/2002 |
| WO | WO 03/026483 | 4/2003 |
| WO | WO 03/026484 | 4/2003 |
| WO | WO 03/026485 | 4/2003 |
| WO | WO 2004/021927 | 3/2004 |
| WO | WO 2005/028025 | 3/2005 |

OTHER PUBLICATIONS

Anstadt, George L., et al., A New Instrument for Prolonged Mechanical Cardiac Massage, *Abstracts of the 38th Scientific Sessions*, Supplement II to *Circulation*, vols. 31 and 32, pp. 375-384, Oct. 1965.

Paling, D.F., *Warp Knitting Technology*, 1970.

Edie, Richard N., M.D., et al., Surgical Repair of Single Ventricle, *The Journal of Thoracic and Cardiovascular Surgery*, vol. 66, No. 3, pp. 350-360, Sep. 1972.

McGoon, Dwight C., M.D., et al., Correction of the Univentricular Heart Having Two Atriovantricular Valves, *The Journal of Thoracic and Cardiovascular Surgery*, vol. 74, No. 2, pp. 218-226, Aug. 1977.

Doty, Donald B., et al., Septation of the Univentricular Heart: Transatrial Approach, *The Journal of Thoracic and Cardiovascular Surgery*, vol. 78, No. 3, pp. 424-430, Sep. 1979.

Schetky, L. McDonald, Shape-Memory Alloys, *Scientific American*, vol. 241, No. 5, pp. 74-82, Nov. 1979.

Melton, K.N., et al., Alloys With Two-Shape Memory Effect, *Mechanical Engineering*, pp. 42-43, Mar. 1980.

Feldt, Robert H., M.D., et al., Current Status of the Septation Procedure for Univentricular Heart, *The Journal of Thoracic and Cardiovascular Surgery*, vol. 82, No. 1, pp. 93-97, Jul. 1981.

Carpentier, A., et al., Myocardial Substitution With Stimulated Skeletal Muscle: First Successful Clinical Case, *The Lancet*, Jun. 1, 1985.

Anstadt, George L. et al., Direct Mechanical Ventricular Actuation: A Review, *Resuscitation*, pp. 7-23, 1991.

Anstadt, Mark P., M.D., et al., Pulsatile Reperfusion After Cardiac Arrest Improves Neurologic Outcome, *American Surgery*, vol. 214, No. 4, pp. 478-490, Oct. 1991.

Schumacker, Harris B., Jr., Chapter 21: Cardiac Aneurysms, *The Evolution of Cardiac Surgery*, pp. 159-165, 1992.

Savage, Edward B., M.D., et al., Repair of Left Ventricular Aneurysm, *The Journal of Thoracic and Cardiovascular Surgery*, vol. 104, No. 3, pp. 752-762, Sep. 1992.

Carpentier, Alain, M.D., Ph.D., et al., Dynamic Cardiomyoplasty at Seven Years, *The Journal of Thoracic and Cardiovascular Surgery*, vol. 106, No. 1, pp. 42-54, Jul. 1993.

Capouya, Eli R., M.D., et al., Girdling Effect of Nonstimulated Cardiomyoplasty on Left Ventricular Function, *Annals of Thoracic Surgeons*, vol. 56, pp. 867-871, 1993.

Chekanov, Valeri, M.D., Ph.D., Nonstimulated Cardiomyoplasty Wrap Attenuated the Degree of Left Ventricular Enlargement, *Annals of Thoracic Surgeons*, vol. 57, pp. 1684-1690, 1997.

Chiu, Ray C.-J, Using Skeletal Muscle for Cardiac Assistance, *Scientific American*, pp. 68-77, Nov./Dec. 1994.

Kass, David A., M.D., et al., Reverse Remodeling From Cardiomyoplasty in Human Heart Failure: External Constraint Versus Active Assist, *Circulation*, vol. 91, No. 9, pp. 2314-2318, May 1, 1995.

Vaynblat, Mikhail, M.D., et al., Cardiac Binding in Experimental Heart Failure, Annals of Thoracic Surgery (Abstract), Supplement to *Circulation*, vol. 92, Suppl. 1, 1995.

Levin, Howard R., M.D., et al., Reversal of Chronic Ventricular Dilation in Patients With End-Stage Cardiomyopathy by Prolonged Mechanical Unloading, *Circulation*, vol. 91, No. 11, pp. 2717-2720, 1995.

Chaudhry, Pervaiz A., M.D., et al., Acute Ventricular Reduction with Acorn's Cardiac Support Device Prevents Progressive Left Ventricular Dysfunction and Remodeling in Dogs With Advanced Heart Failure, *Cardiothoracic Surgery*, pp. 146-148, 1996.

Oh, Joong Hwan, M.D., et al., Mechanisms of Dynamic Cardiomyoplasty: Current Concepts, *Journal of Cardiac Surgery*, vol. 11, pp. 194-199, 1996.

Badhwar, Vinay, Power Generation From Four Skeletal Muscle Configurations Design Implications for a Muscle Powered Cardiac Assist Device, *ASAIO Journal*, vol. 43, pp. M651-M657, 1997.

Westaby, Stephen, et al., *Landmarks in Cardiac Surgery*, pp. 198-199, 1997.

Cox, James L., Left Ventricular Aneurysms: Pathophysiologic Observations and Standard Resection, *Seminars in Thoracic and Cardiovascular Surgery*, vol. 9, No. 2, pp. 113-122, Apr. 1997.

Coletta, C., et al., Prognostic Value of Left Ventricular Volume Response During Dobutamine Stress Echocardiography, *European Heart Journal*, vol. 18, pp. 1599-1603, Oct. 1997.

Capomolla, Soccorso, M.D., et al., Dobutamine and Nitroprusside Infusion in Patients With Severe Congestive Heart Failure: Hemodynamic Improvement by Discordant Effects on Mitral Regurgitation, Left Atrial Function, and Ventricular Function, *American Heart Journal*, 1089-1098, Dec. 1997.

Oh, Joong Hwan, The Effects of Prosthetic Cardiac Binding and Adynamic Cardiomyoplasty in a Model of Dilated Cardiomyopathy, *The Journal of Thoracic and Cardiovascular Surgery*, vol. 116, No. 1, pp. 148-153, 1998.

Cohn, Jay N., M.D., Preventing Congestive Heart Failure, *American Family Physician*, 6 pages, Apr. 15, 1998.

Cohn, Jay N., M.D., Structural Basis for Heart Failure: Ventricular Remodeling and Its Pharmacological Inhibition, *Circulation*, vol. 91, No. 10, pp. 2504-2507, May 15, 1995.

Gaudron, Peter, M.D., et al., Progressive Left Ventricular Dysfunction and Remodeling After Myocardial Infarction, *Circulation*, vol. 87, pp. 755-763, Mar. 1993.

Pfeffer, Marc A., M.D., et al., Ventricular Remodeling After Myocardial Infarction: Experimental Observations and Clinical Implications, *Circulation*, vol. 81, No. 4, pp. 1161-1172, Apr. 1990.

Guasp, Francisco Torrent, Una protesis contentiva para el tratamiento de le microcardiopatia dilatads, *Revista Española de Cardiologia*, vol. 51, No. 7, Jul. 1998.

Power, J.M., et al., Passive Ventricular Constraint Amends the Course of Heart Failure: A Study in an Ovine Model of Dilated Cardiomyopathy, *Cardiovascular Research*, vol. 44, pp. 549-555, 1999.

Frazier, O.H., M.D., et al., Left Ventricular Assist System as a Bridge to Myocardial Recovery, *Annals of Thoracic Surgery*, vol. 68, pp. 734-741, 1999.

Melvin, David B., Ventricular Radius Reduction Without Resection: A Computational Analysis, *ASAIO Journal*, pp. 160-165, 1999.

*Abstracts—Heart Failure*, JACC Feb. 1999.

Raman, Jai S., Fracs, et al., Ventricular Containment as an Adjunctive Procedure in Ischemic Cardiomyopathy: Early Results, *Annals of Thoracic Surgery*, vol. 70, pp. 1124-1126, Jan. 2000.

McCarthy, Patrick M., et al., *Device Based Left Ventricular Shape Change Immediately Reduces Left Ventricular Volume and Increases Ejection Fraction in a Pacing Induced Cardiomyopathy Model in Dogs*, JACC, Feb. 2000.

Chaudhry, Pervaiz A., M.D., et al., Passive Epicardial Containment Prevents Ventricular Remodeling in Heart Failure, *Annals of Thoracic Surgeons*, vol. 70, pp. 1275-1280, 2000.

Acorn Cardiovascular, Inc., *CSD Specifications Acorn Cardiac Support Device*, 2000.

Heart "jacket" could help stop heart failure progression, *Clinicia*, No. 916, Jul. 2000.

Acorn Cardiovascular, Inc., *CorCap™ Cardiac Support Device* Pamphlet, Jun. 2001.

*Medtronic's InSync Cardiac Resynchronization Therapy Device Approved by FDA*, (Press Release) Aug. 28, 2001.

Oz, Mehmet C., M.D., Passive Ventricular Constraint for the Treatment of Congestive Heart Failure, *Annals of Thoracic Surgery*, vol. 71, pp. 5185-5187, 2001.

Abstract Supplement, *European Heart Journal*, vol. 22, Sep. 2001.

Gorman, J., Self-Sutures: New Material Knots Up on Its Own, *Science News*, vol. 161, p. 262, Apr. 27, 2002.

Mann, Douglas L., M.D., *Basic Mechanisms of Remodeling and Reverse Remodeling*, presented at $6^{th}$ Annual Scientific Meeting of the Heart Failure Society of America, Sep. 24, 2002.

Bocchi, Edimar A., M.D., Arrhythmias and Sudden Death After Dynamic Cardiomyoplasty, *Circulation*, vol. 90, No. 5, Part 2, pp. II-107 thru II-111, Nov. 1994.

Chachques, Juan C., M.D., Study of Muscular and Ventricular Function in Dynamic Cardiomyoplasty: A Ten-Year Follow-Up, *The Journal of Heart and Lung Transplantation*, vol. 16, No. 8, pp. 854-868, Aug. 1997.

Dullum, Mercedes K.C., M.D., et al., *Less Invasive Surgical Management of Heart Failure by Cardiac Support Device Implantation on the Beating Heart*, The Heart Surgery Forum, #2001-1818, pp. 361-363, Jan. 4-7, 2001.

Macris, Michael P. M.D., et al., Minimally Invasive Access of the Normal Preicardium: Initial Clinical Experience with a Novel Device, *Clinical Cardiology*, vol. 22 (Suppl. I), pp. I-36 thru I-39, 1999.

Thakur, Ranjan K., M.D., et al., Latissimus Dorsi Dynamic Cardiomyoplasty: Role of Combined ICD Implantation, *Journal of Cardiac Surgery*, vol. 10, pp. 295-297, 1995.

Wharton, J. Marcus, et al., Electrophysiological Effects of Monophasic and Biphasic Stimuli in Normal and Infarcted Dogs, *PACE*, vol. 13, pp. 1158-1172, Sep. 1990.

Shabetai, Ralph, The Role of the Pericardium in the Pathophysiology of Heart Failure, *Congestive Heart Failure*, Second Edition, Chapter 9, pp. 157-187, 2000.

Cohn, Jay N., M.D., The Management of Chronic Heart Failure, *The New England Journal of Medicine*, vol. 335, No. 7, pp. 490-498, Aug. 15, 1996.

Zhou, Xiaohong, et al., Epicardial Mapping of Ventricular Defibrillation With Monophasic and Biphasic Shocks in Dogs, *Circulation Research*, vol. 72, No. 1, pp. 145-160, Jan. 1993.

Shorofsky, Stephen R., et al., Comparison of Step-Down and Binary Search Algorithms for Determination of Defibrillation Threshold in Humans, *PACE*, vol. 27, pp. 218-220, Feb. 2004.

Gold, Michael R., M.D., et al., Comparison of Single- and Dual-Coil Active Pectoral Defibrillation Lead Systems, *Journal of the American College of Cardiology*, vol. 31, No. 6, pp. 1391-1394, May 1998.

Rinaldi, C. Aldo, A Randomized Prospective Study of Single Coil Versus Dual Coil Defibrillation in Patients With Ventricular Arrhythmias Undergoing Implantable Cardioverter Defibrillator Therapy, *PACE*, vol. 26, pp. 1684 1690, Aug. 2003.

Schwartzman, David, M.D., et al., Serial Defibrillation Lead Impedance in Patients with Epicardial and Nonthoracotomy Lead Systems, *Journal of Cardiovascular Electrophysiology*, vol. 7, No. 8, pp. 697-703, Aug. 1996.

Sandstedt, Bengt, et al., Bidirectioinal Defibrillation Using Implantable Defibrillators: A Prospective Randomized Comparison Between Pectoral and Abdominal Active Generators, *PACE*, vol. 24, Part I, pp. 1343-1353, Sep. 2001.

Schulte, B., et al., Dual-Coil vs. Single-Coil Active Pectoral Implantable Defibrillator Lead Systems: Defibrillation Lead Requirements and Probability of Defibrillation Success at Multiples of the Defibrillation Energy Requirements, *Europace*, vol. 3, pp. 177-180, Jul. 2001.

Lin, Z.C., et al., The Effect of Cold Work Texture on the Superelastic characteristics of Nitinol Sheet, *Materials Science Forum*, vol. 394-395, 2002, pp. 313-316, SP9009041321, Switzerland; See experimental section and the first conclusion.

Application for U.S. Letters U.S. Appl. No. 11/097,405, filed Apr. 1, 2005; Inventor: Lau et al.

Application for U.S. Letters U.S. Appl. No. 11/158,913, filed Jun. 21, 2005; Inventor: Lau et al.

Application for U.S. Letters U.S. Appl. No. 11/193,043, filed Jul. 29, 2005; Inventor: Lau et al.

Application for U.S. Letters U.S. Appl. No. 11/304,070, filed Dec. 14, 2005; Inventor: Lau et al.

Application for U.S. Letter U.S. Appl. No. 11/317,624, filed Dec. 22, 2005; Inventor: Lau et al.

Application for U.S. Letters U.S. Appl. No. 11/343,926, filed Jan. 30, 2006; Inventor: Lau et al.

Application for U.S. Letters U.S. Appl. No. 11/515,226, filed Sep. 1, 2006; Inventor: Schaer et al.

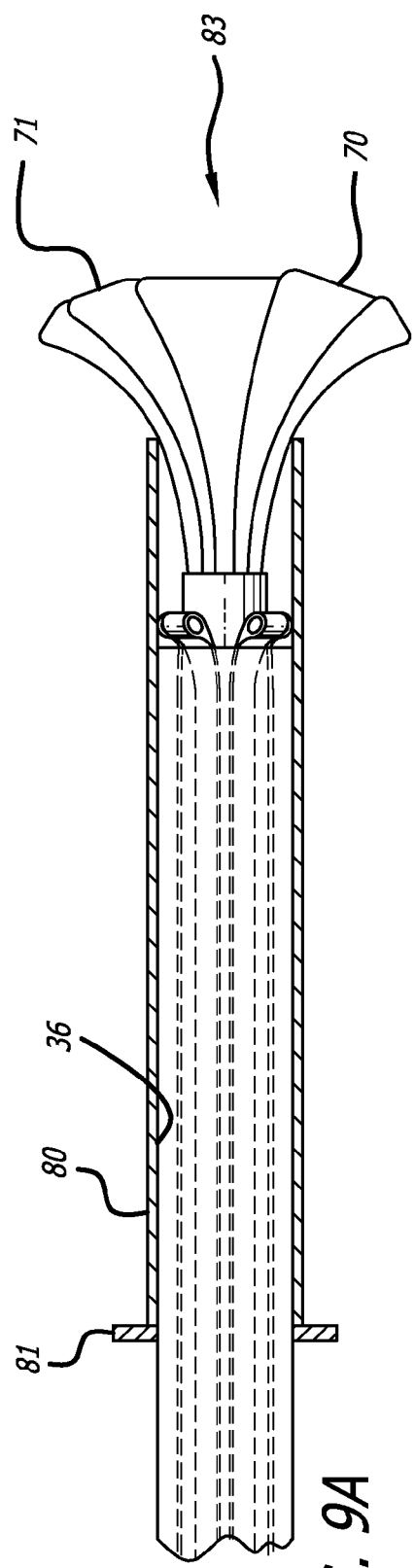
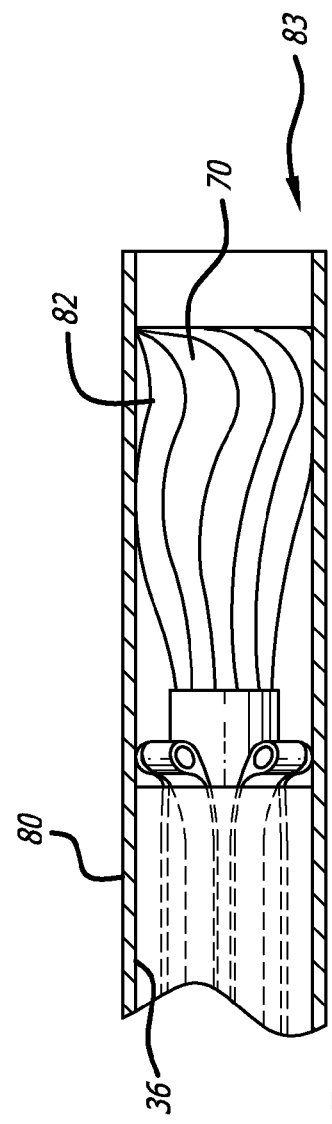
FIG. 9A
FIG. 9B

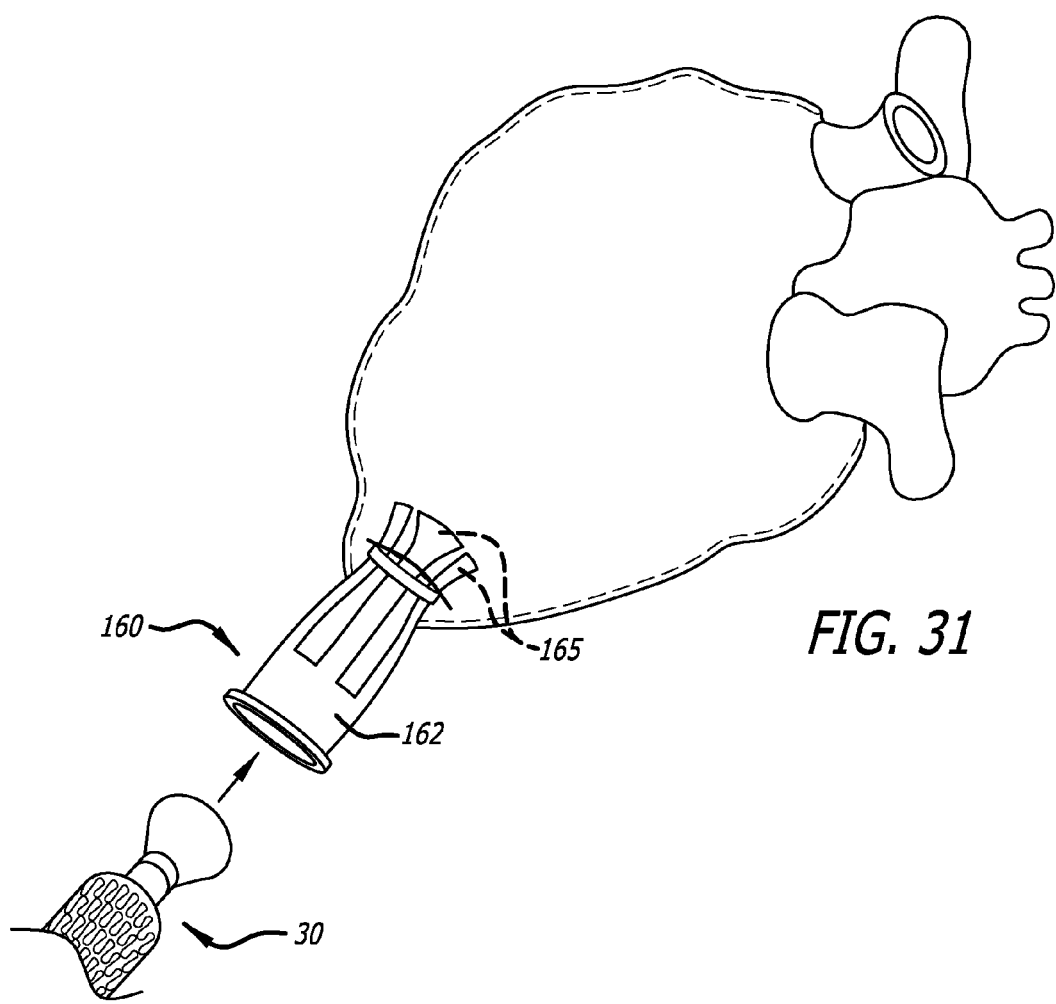

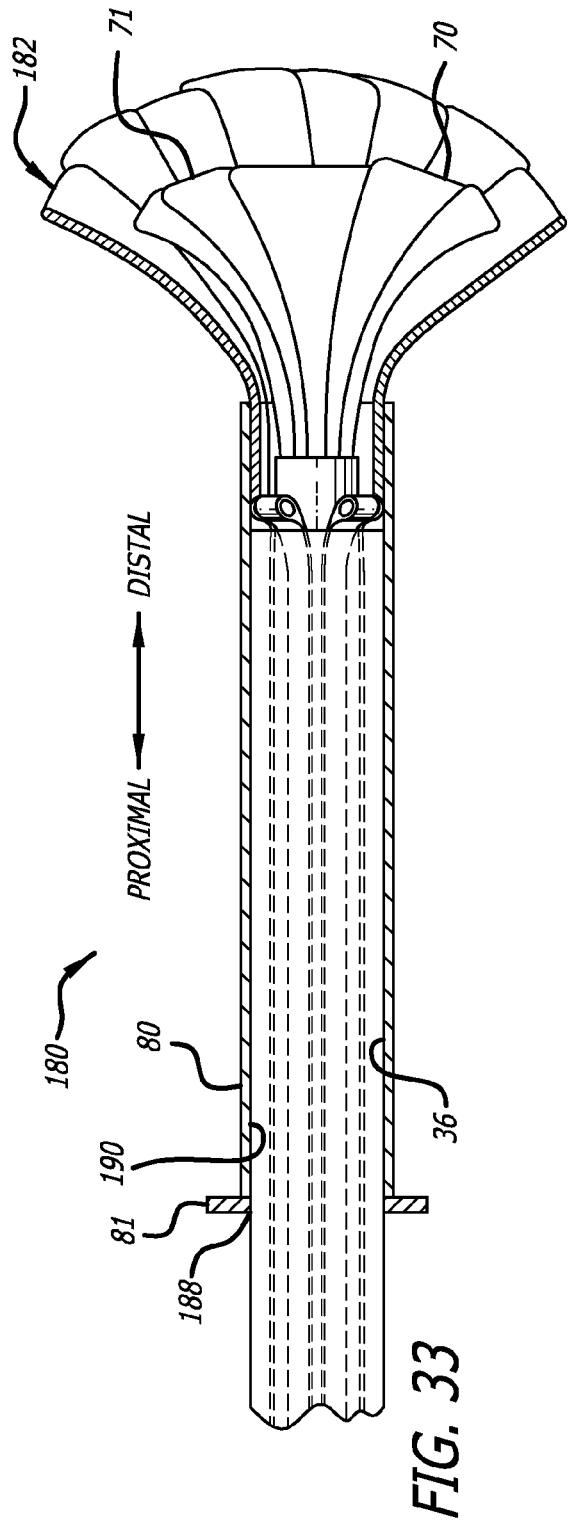
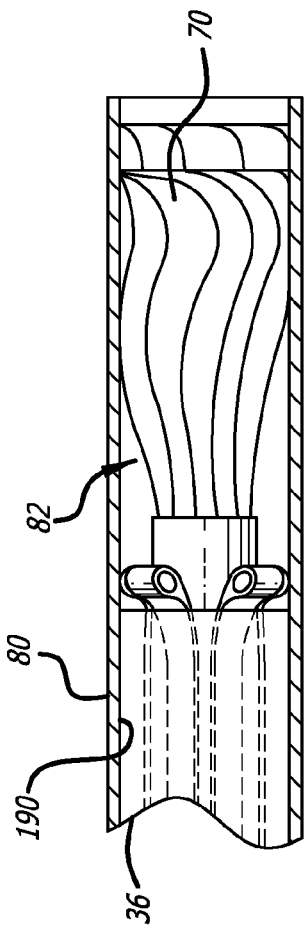
FIG. 33
FIG. 34

MEDICAL DEVICE DELIVERY SYSTEM HAVING INTEGRATED INTRODUCER

CROSS-REFERENCES TO RELATED APPLICATIONS

This application is a continuation-in-part of prior U.S. application Ser. No. 11/837,619, filed Aug. 13, 2007, which is pending, and which is incorporated herein by reference in its entirety.

FIELD OF THE INVENTION

The present invention relates generally to a system and associated method for delivering a medical device, and more particularly, to a medical delivery device having an integral introducer.

BACKGROUND OF THE INVENTION

Congestive heart failure ("CHF") is characterized by the failure of the heart to pump blood at sufficient flow rates to meet the metabolic demand of tissues, especially the demand for oxygen. It has been determined that a passive wrap, or cardiac harness, may increase the efficiency of a heart affected by congestive heart disease. While advances have been made in cardiac harness technology, a satisfactory device for delivering and positioning the cardiac harness onto a patient's heart has yet to be provided.

In one method, access to a patient's heart is achieved through an open chest procedure, wherein the sternum is split and separated to allow access to the heart. The cardiac harness is then positioned over the heart by manual manipulation. Such an open chest procedure is highly traumatic to the patient and, thus, remains a relatively undesirable option for cardiac harness delivery.

Present cardiac harness delivery devices are adapted for use in minimally invasive procedures in which the delivery devices are advanced through a relatively small incision through the body cavity of a patient. Because of the relatively rigid structure and size of such delivery devices, separate introducer devices are used to create an entry path sufficient in size to allow the delivery device to access the heart. In addition, access to the apex of the heart is typically required, in which case an entry path that passes between two ribs is convenient. Importantly, since CHF hearts are enlarged, they have an apex that is rounded which presents a very steep angle of approach when mounting a cardiac harness over the heart.

An example of an introducer assembly 160 usable to assist in creating an access opening in the pericardium of a patient's heart to permit deployment of a medical device, such as a cardiac harness, to the heart is provided in FIGS. 26, 27, and 28. In this embodiment, the introducer assembly includes an introducer sleeve 162 and a dilator sleeve 164. The introducer sleeve 162 has outwardly extending flanges 150 at the proximal end 152, the flanges being sufficiently sized to serve as a grip. With the flanges, the introducer sleeve may be easily held in place by the doctor while inserting the dilator sleeve 164.

With particular reference to FIG. 26, the introducer sleeve 162 is a thin-walled, tubular element having a substantially circular cross-sectional shape. A distal end 163 of the introducer sleeve 162 comprises a plurality of flared portions 165 that are biased outwardly from a longitudinal axis $A_s$ of the introducer sleeve 162. In the illustrated embodiment, a portion of the introducer sleeve 162 is divided into several elongate strips 166 that are spaced apart from each other. A resilient annular member, such as an elastic ring 168, is positioned toward the distal end 163 of the introducer sleeve 162 to bias the strips 166 into a reduced-diameter configuration, which is operable to ease insertion of the introducer sleeve 162 into an incision in the pericardium.

Referring now to FIG. 27, the dilator sleeve 164 is a thin-walled, tubular member, which is also substantially circular in cross-section. The dilator sleeve 164 is slidably inserted within the introducer sleeve 162, as illustrated in FIG. 28 to expand the strips 166 and flared portions 165. In particular, the dilator sleeve 164 presses against an inner surface of the reduced-diameter portion of the introducer sleeve 162 to force the reduced-diameter portion outward against the biasing force provided by the elastic ring 168. Thus, in the assembled configuration, the reduced diameter portion of the introducer sleeve 162 is enlarged and the introducer assembly 160 is configured to provide an access pathway for the delivery device 30. The dilator sleeve 164 also has an enlarged diameter portion 170 on its proximal most end to limit the insertion within the introducer sleeve 162.

FIG. 29 illustrates a human heart 172, which is enclosed within a pericardium 174. To permit introduction of the delivery device 30 to a location within the pericardium 174, preferably, a small incision 176 is made in the pericardium 174 adjacent the apex of the heart. With reference next to FIG. 30, the introducer sleeve 162, in its contracted, or collapsed, orientation is introduced into and through the incision 176. In practice, one side of the distal end of the introducer sleeve 162 may be inserted into the incision 176 first, followed by the remaining side.

With reference next to FIG. 31, once the flared portions 165 of the introducer sleeve 162 have been advanced through the slit 176, the dilator sleeve 164 is then introduced within the introducer sleeve 162 to urge the introducer sleeve 162 into its expanded configuration. In this configuration, the flared portions 165 are expanded to a diameter greater than the diameter of the rest of the introducer sleeve 162 and preferably greater than the size of the incision 176. As such, the flared portions 165 press upon and open the incision 176 and the surrounding portion of the pericardium so as to create a space between at least part of the pericardium and the heart. Further, the flared portions 165 function as a lock to resist pulling the introducer out of the incision 176. Accordingly, the introducer assembly 160 is effectively locked in place between the heart 172 and the pericardium 174.

Since the dilator sleeve 164 dilates the introducer sleeve 162, an access pathway is created to allow the delivery device 30 to be advanced through the dilator sleeve, the introducer sleeve, and through the pericardium to deliver the cardiac harness 42 onto the heart 172. When the procedure is completed, the delivery device 30 is retracted through the access pathway and the introducer arrangement 160 is removed in generally the reverse order of the insertion.

While the above discussed and illustrated introducer assembly has provided a significant advance in the art and has provided advantages in delivering cardiac harnesses recognized and appreciated by many in the art, it has also been recognized that providing even smaller delivery devices that may accomplish both the introducing and delivery functions simultaneously would be desirable. Provided that such smaller delivery devices are in fact less traumatic, include fewer parts or complexity, and provide equivalent functionality, such would be of interest.

SUMMARY OF THE INVENTION

Briefly and in general terms, the present invention is directed to a system and an associated method for delivery of a medical device. In a general aspect, there is provided a delivery system for deploying a medical device with the delivery system comprising a housing having a longitudinal axis, a proximal end, a distal end, and a medical device location adapted to releasably contain the medical device, an outer deflector that deploys to a first diameter at a distal end, the outer deflector also having a proximal end mounted at the distal end of the housing, an inner deflector disposed within the outer deflector, the inner deflector deploying to a second diameter, and having a proximal end and a distal end, and a compression device disposed over the housing, movable in relation to the housing, and adapted for moving over the outer and inner deflectors to a delivery position to thereby collapse both the outer and inner deflectors into a delivery configuration, and for sliding to a retracted position to permit the outer and inner deflectors to expand to a deployed configuration, wherein the medical device location in the housing is located so that the medical device is deployed between the outer and inner deflectors.

In more detailed aspects, the outer and inner deflectors are configured to be self expanding. The outer deflector comprises a plurality of petals, each petal having a proximal end and a distal end, the petals flaring outwardly in the deployed configuration at the distal end, and the inner deflector comprises a plurality of petals, each petal having a proximal end and a distal end, the petals flaring outwardly in the deployed configuration at the distal end. The petals of the inner deflector are formed such that they taper from a relatively narrower proximal end to a relatively wider distal end, wherein the petals of the outer deflector are formed such that they are not tapered from one end to the other. At least a portion of each petal of the inner deflector overlaps an adjacent petal. Adjacent petals of the inner deflector are configured in relation to one another so that they slide over each other when the inner deflector is collapsed to the delivery configuration and expanded to the deployed configuration.

Further more detailed aspects include the petals of the outer deflector being separate from one another such that they do not overlap one another in either the delivery or deployed configurations. The inner deflector comprises a first set of petals having a first set of gaps between them, and a second set of petals having a second set of gaps between them, wherein the first set of petals interleaves with the second set of petals by filling the second gaps and the second set of petals interleaves with the first set of petals by filling the first gaps. The outer deflector comprises a third set of petals having a third set of gaps between them, and a fourth set of petals having a fourth set of gaps between them, wherein the third set of petals interleaves with the fourth set of petals by filling the fourth gaps and the fourth set of petals interleaves with the third set of petals by filling the third gaps.

In other aspects, the housing comprises an outer tubular wall having a distal end and an outer surface with the outer deflector comprising a plurality of petals that are formed at the distal end of the tubular wall of the housing and extend distally therefrom, wherein the compression device comprises a compression sheath adapted to be slidable over the outer surface of the tubular wall of the housing to the delivery position to cover and collapse the outer deflector petals into the delivery configuration. The outer deflector petals are formed as part of an outer deflector ring that is aligned with and attached to the distal end of the tubular wall of the housing. In a more detailed aspect, the outer deflector ring and the distal end of the tubular wall of the housing comprise complementary threads wherein the outer deflector ring and the tubular wall of the housing are attached together by engagement of these threads. A plurality of the deflector petals comprise distal tips having varying radii at the distal tips. A plurality of the deflector petals comprise varying thicknesses between the proximal ends and the distal ends.

Additional more detailed aspects include the outer deflector being formed to the distal end of the tubular wall by a mechanical connection selected from the group consisting of: threaded fit, snap fit, overmolded, adhesively bonded, chemically bonded, and molded directly as part of the tubular wall. A radiopaque material is attached to at least some of the petals to enhance visualization of the system under fluoroscopy, wherein the radiopaque material comprises barium sulfate. A radiopaque material is embedded within at least some of the petals to enhance visualization of the system under fluoroscopy.

Yet further aspects in accordance with the invention include the housing comprising an outer tubular wall having a distal end and an outer surface with the outer deflector comprising a plurality of petals that are formed at the distal end of the tubular wall of the housing and extending distally therefrom, the outer and inner deflectors are self expanding, the outer deflector comprises a plurality of petals, each petal having a distal end at which the petal flares outwardly in the deployed configuration, the inner deflector comprises a plurality of petals, each petal having a distal end at which the petal flares outwardly in the deployed configuration, and the compression device comprises a compression sheath adapted to be slidable over the outer surface of the tubular wall of the housing to the delivery position to cover and collapse the outer deflector petals and the inner deflector petals into the delivery configuration. The housing has a substantially circular cross-sectional shape having a diameter, and wherein at least a portion of the housing is compressible to a substantially elliptical cross-sectional shape having a minor axis that is less than the diameter. The cross-sectional shape is adapted for advancing through a minimally invasive surgical entry path.

In accordance with general aspects of an associated method, the method of delivering a medical device comprises advancing an elongated delivery housing through an access site, deploying an outer deflector from the delivery housing, expanding the outer deflector to engage first tissue, deploying an inner deflector from the delivery housing, expanding the inner deflector to engage second tissue, advancing the medical device out of the delivery housing under the expanded outer deflector and over the expanded inner deflector into a desired position, collapsing the inner and outer deflectors, and withdrawing the delivery housing with the inner and outer deflectors from the access site. In detailed aspects, the outer deflector is self expanded and the inner deflector is self expanded.

In more detailed aspects, the step of expanding the inner deflector to engage the second tissue comprises guiding delivery of the medical device into the desired position with the second deflector. The step of expanding the inner deflector to engage the second tissue further comprises protecting the second tissue with the second deflector during delivery of the medical device. The step of expanding the outer deflector further comprises engaging the first tissue to move it away from the second tissue thereby opening a space between the first and second tissues for delivery of the medical device.

In general aspects of a delivery system with an integrated introducer for introducing and deploying a medical device, the delivery system comprises a tubular housing comprising an outer tubular wall, the wall having an outer surface, a longitudinal axis, and a distal end, the tubular housing also comprising a medical device location adapted to releasably contain the medical device within the tubular wall, an outer deflector that deploys outwardly to a first diameter at a distal end, the outer deflector having a proximal end mounted at the distal end of the tubular housing wall, and a compression sheath disposed over the outer surface of the tubular wall and longitudinally movable in relation thereto, the sheath adapted for moving over the outer deflector to an introducer position to thereby collapse the outer deflector into a delivery configuration, and for moving to a retracted position to permit the outer deflector to expand to a deployed configuration, wherein the medical device location in the housing is located so that the medical device is deployed through the outer deflector.

Turning now to further associated method aspects, there is provided a method of introducing and delivering a medical device with a single system, the system comprising a housing with outwardly expanding deflector fixedly mounted to a distal end of the housing, and a compression sheath movably mounted over the housing, the method comprising moving the compression sheath over the housing and the deflector to an introducer configuration thereby collapsing the deflector within the compression sheath, advancing the compression sheath and collapsed deflector that are in the introducer configuration through an access site, moving the compression sheath over the housing away from the deflector to a delivery position thereby deploying the deflector, expanding the deflector outwardly to engage first tissue to move it away from second tissue, advancing the medical device out of the delivery housing under the expanded deflector into a desired position, moving the compression sheath over the housing to the introducer position to collapse the deflector thereby attaining the introducer configuration; and withdrawing the delivery housing, the compression sheath, and the deflector from the access site.

In more detailed method steps, the step of expanding the outer deflector comprises self expanding the outer deflector, and the step of advancing the medical device comprises advancing the medical device into a desired position in relation to the second tissue.

In much more detailed aspects of a system in accordance with the invention, there is provided an apparatus for delivering a cardiac harness onto a heart, comprising an elongate body having a proximal portion and a distal portion, the distal portion having a tubular housing sized to contain the cardiac harness in a compacted configuration, the tubular housing having a proximal end, an open distal end, an inner surface, and an outer surface, a plurality of elongate push rods longitudinally movable with respect to the elongate body, the cardiac harness releasably connected to each of the push rods such that advancement of the push rods in a distal direction moves the cardiac harness from the compacted configuration in the housing to an expanded configuration outside the housing, an outer deflector having a distal end and a proximal end, the outer deflector being flexible and configured so that it can be collapsed into a delivery configuration, and can be flared radially outwardly to a deployed configuration at which it has a first diameter at its distal end, an inner deflector having a distal end and a proximal end, the inner deflector being flexible and configured so that it can be collapsed into a delivery configuration, and can be flared radially outwardly to a deployed configuration at which it has a second diameter at its distal end, a deflector sheath slidably mounted over the outer surface of the tubular housing and having a delivery position at which the sheath retains the outer and inner deflectors in a collapsed, delivery configuration, and the deflector sheath being further slidably mounted over the outer surface of the tubular housing to a deployment position at which the outer and inner deflectors flare radially outwardly in deployed configurations so that the outer deflector engages the pericardium and the push rods and cardiac harness slide under the outer deflector and over the inner deflector as the harness slides over the heart.

In more detailed aspects, the inner deflector comprises a plurality of petals, the plurality of petals being configured to be collapsed into the deflector sheath in a delivery configuration and flared radially outwardly in a deployed configuration at which the petals have a second diameter at a distal end, the second diameter being smaller than the first diameter of the outer deflector. In one aspect, the plurality of petals number in the range from four to twenty petals. The petals are formed from a polymer material which is taken from the group of polymers including polyamides, polyamide copolymers such as PEBAX, silicone rubber, polyurethanes, and nylons with the proximal ends of the petals are biased radially outwardly to form a flared configuration.

In yet further detailed aspects, the housing has a cross-sectional shape having a first perimeter, and wherein at least a portion of the housing is compressible to a reduced cross-sectional shape having a second perimeter that is less than the first perimeter. The cross-sectional shape is adapted for advancing through a minimally invasive surgical entry path, and the housing tapers from a first cross-sectional shape having a first perimeter at the proximal end of the housing to a second cross-sectional shape having a second perimeter at the distal end of the housing, the second perimeter being smaller in size than the first perimeter.

In an associated method, there is provided a method of delivering a cardiac harness onto a heart, comprising advancing an elongated delivery device through a minimally invasive access site, deploying an outer deflector from the delivery device to engage the pericardium and open a space between the pericardium and the heart, deploying an inner deflector from the delivery device to engage the heart, advancing a cardiac harness out of the delivery device under the outer deflector and over the inner deflector, flaring the cardiac harness outwardly over the inner deflector and onto the heart, and withdrawing the delivery device with the inner and outer deflectors through the access site.

More detailed aspects comprise extending a suction cup from a distal end of the delivery device, engaging the heart with the extended suction cup, and applying a vacuum to the suction cup to firmly attach the cup onto the heart. The inner deflector extends over the suction cup.

In yet further aspects, the delivery device includes paired deflectors enabling introducer-less deployment of a cardiac harness. An inner deflector contacts the heart and provides an atraumatic guide for the cardiac harness as the harness is mounted onto the heart. The inner deflector prevents row flipping (either over or under) associated with certain cardiac harness structures and it permits a smooth transition for the harness as it is advanced over the steep angle presented by the enlarged CHF heart. The need for an introducer is thus obviated by the delivery device having the outer deflector, as well as its other features. The outer deflector opens the pericardium away from the heart so that the cardiac harness may be deployed about the heart and retains the delivery device in position in the pericardium during delivery.

At least some of the petals can be loaded with a radiopaque material to enhance visualization of the petals under fluoroscopy, or the polymer material of the petals have a radiopaque material attached thereto in order to enhance visualization under fluoroscopy.

In a further aspect in accordance with the invention, the outer deflector is attached to the housing by mechanical means, such as a thread or snap feature, or a combination thereof. These mechanical attachments may also be strengthened by use of adhesives, or the attachment may rely solely on the adhesive bond. The attachment to the housing may furthermore be a chemical bond in the form of an overmold, where the outer deflector is molded directly onto the housing, and the materials chosen for both components ensure a robust, strong bond. Regardless of the attachment method, the outer deflector would be formed into a flared trumpet shape and packaged/stored in that stress-free state, ensuring that the shape is retained over time up until the point of use or if a memory shape material is used, packaged in a convenient way permitting access and use as needed.

In another detailed aspect of the invention, a medical device includes an inner deflector having a first ring with a plurality of first petals attached to the first ring, the first petals being spaced apart and forming first gaps between adjacent first petals. The inner deflector also includes a second ring with a plurality of second petals attached to the second ring, the second petals being spaced apart and forming second gaps between adjacent second petals. Further, the first ring and the second ring are configured to interlock so that the first petals and the second petals overlap when the first ring and the second ring are interlocked. The interlocking rings provide a smooth transition area as the harness is advanced over the inner deflector. In the case where the outer deflector comprises petals, a similar use of interlocking rings may be employed as in the inner deflector.

In another aspect, the housing has a substantially circular cross-sectional shape having a diameter. In this aspect, at least a portion of the housing is compressible to a substantially elliptical cross-sectional shape having a minor axis that is less than the diameter. In yet another aspect, the housing has a cross-sectional shape having a first perimeter. A deflector sheath for retaining the outer and inner deflectors has a second perimeter that is greater than the housing first perimeter so that the deflector sheath slidingly extends over at least a distal portion of the housing. At least a portion of the housing and deflector sheath are compressible to a reduced cross-sectional shape having a third perimeter that is less than the first and second perimeters. The outer and inner deflectors also are compressible to conform to the elliptical cross-sectional shape of the deflector sheath to facilitate delivery.

In yet another aspect, the housing has a cross-sectional shape having a first dimension. The first dimension is equivalent to the shortest possible linear distance between any two points on the perimeter of the cross-sectional shape and passing through the center of the cross-sectional shape. In this aspect, at least a portion of the housing is collapsible to a reduced cross-sectional shape having a second dimension that is less than the first dimension. The second dimension is equivalent to the shortest possible linear distance between any two points on the perimeter of the reduced cross-sectional shape and passing through the center of the reduced cross-sectional shape. A deflector sheath and deflector mounted on a distal portion of the housing also are compressible to conform to the housing second dimension reduced cross-sectional shape.

In another aspect, the housing tapers from a first cross-sectional shape at the proximal end of the housing to a second cross sectional shape at the distal end of the housing. In this aspect, the perimeter of the second cross-sectional shape is smaller than the perimeter of the first cross-sectional shape. A deflector sheath slidingly mounted over at least a distal portion of the housing also tapers from the deflector sheath proximal end having the perimeter with the first cross-sectional shape to the distal end having the perimeter with the second cross-sectional shape.

BRIEF DESCRIPTION OF THE DRAWINGS

These and other features, aspects and advantages of the present invention are described with reference to drawings of a preferred embodiment, which are intended to illustrate, but not to limit, the present invention.

FIG. 9A is an enlarged side elevational view of the delivery device depicting the deflector sheath withdrawn proximally so that the inner deflector expands into a deployed configuration.

FIG. 9B is an enlarged side elevational view depicting a portion of the delivery device and more specifically depicting the inner deflector in a delivery configuration compressed within the deflector sheath.

FIG. 31 is a view showing the introducer properly placed in position at the medical delivery site with the dilator tube of FIG. 27 in place so that the introducer has taken the configuration of FIG. 28, and showing the application of the medical device to the hollow dilator tube for engaging the medical device with the heart.

FIG. 33 is a view of the two deflector design of FIG. 32 showing the deflectors being partially collapsed through movement of the deflector sheath in the distal direction toward the delivery configuration.

FIG. 34 is a view of the two deflector design of FIG. 32 showing both deflectors fully collapsed within the deflector sheath in the delivery configuration.

DETAILED DESCRIPTION OF THE PREFERRED EMBODIMENTS

Delivery Device

Figure 1:
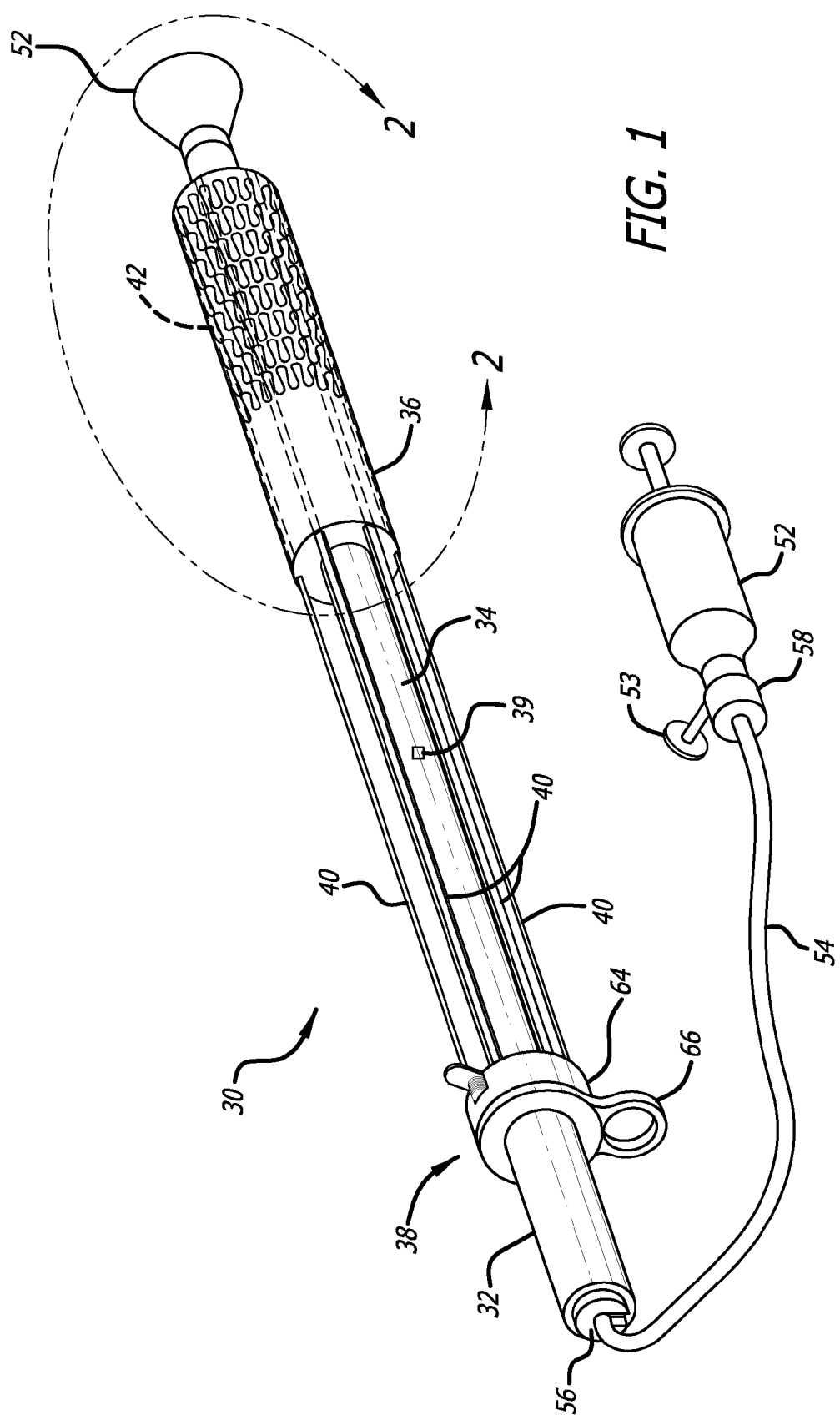
FIG. 1 is a perspective view of a cardiac harness delivery device constructed in accordance with certain features, aspects and advantages of the present invention. The illustrated delivery device comprises a body portion, including an elongate shaft and a housing, and a movable portion, including a control assembly and a plurality of elongate push rods. A cardiac harness is carried by distal end portions of the plurality of push rods.

The exemplary figures illustrate a preferred embodiment of a cardiac harness delivery device, which is generally referred to by the reference numeral 30. In a preferred embodiment, the delivery device 30 is configured to releasably support a cardiac reinforcement device (CRD), such as a cardiac harness, and assist in the advancement of the cardiac harness over the heart of a patient. Once the cardiac harness is positioned on the heart, the delivery device 30 preferably is configured to release the harness and be retractable without causing undesired shifting of the cardiac harness relative to the heart.

In the illustrated arrangement, the delivery device 30 permits delivery of a cardiac harness in a minimally invasive manner. That is, preferably the device 30 permits accurate delivery, positioning, and release of the cardiac harness through a relatively small incision in a patient. However, the preferred, or alternative, embodiments of the delivery device 30 may also be used to deliver a cardiac harness in an open chest, or other minimally invasive procedure. Further, an embodiment preferably is configured to enable indirect visualization of at least portions of the device 30 during surgery. For example, portions of the device may be radiopaque so as to be visualized and guided by fluoroscopy or other methods.

With specific reference to FIG. 1, the illustrated delivery device 30 generally includes a body portion comprised of a handle 32 affixed to the proximal end of a hollow, elongate shaft 34. Preferably, a housing 36 is affixed to a distal end of the elongate shaft 34. The illustrated delivery device 30 also includes a movable portion comprised of a control assembly 38 and a plurality of elongate push rods 40. The control assembly 38 and, thus, the push rods 40, are axially slidable along the shaft 34.

Figure 2:
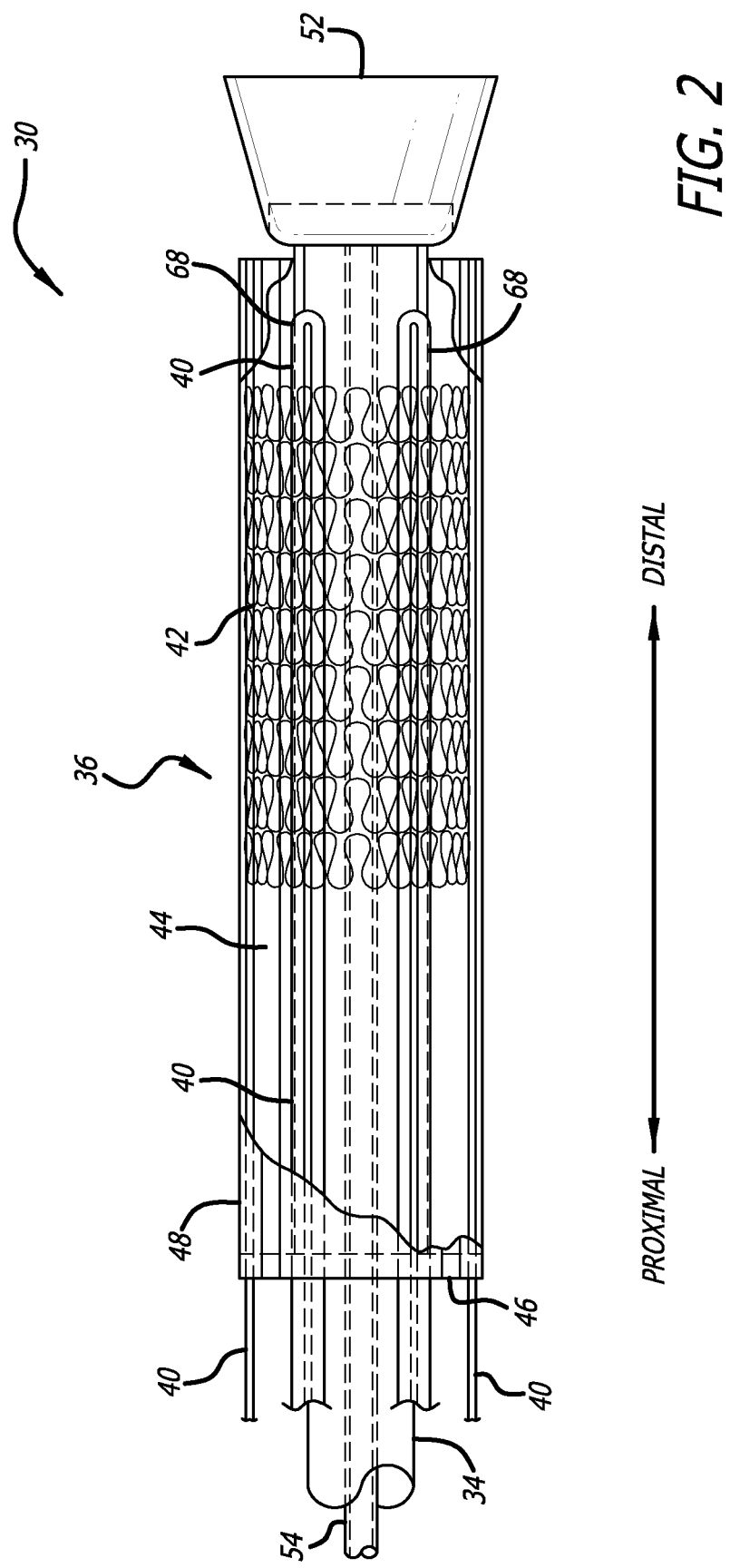
FIG. 2 is an enlarged, partial cutaway view of a distal portion of the delivery device of FIG. 1 showing the cardiac harness in a compacted configuration within a medical device location, in this case a cavity, defined by the housing.

Preferably, the plurality of push rods 40 extend in a distal direction from the control assembly 38 and pass through a housing 36. With reference also to FIG. 2, a cardiac harness 42 is releasably supported on the distal end portions of the elongate push rods 40 in a compacted configuration within the housing 36. Preferably, the cardiac harness 42 comprises an elastic sleeve configured to fit around the heart and to exert a compressive force on the heart. In the illustrated embodiment, the harness 42 comprises several interconnected rows of undulating elastic members. Preferred cardiac harnesses are described in greater detail U.S. Pat. No. 6,702,732; U.S. Pat. No. 6,723,041; U.S. Pat. No. 7,189,203; U.S. application Ser. No. 10/287,723, filed Oct. 31, 2002; and U.S. application Ser. No. 10/656,722, filed Sep. 5, 2003, the entirety of each of which are incorporated by reference herein. It is to be understood that aspects of the delivery device 30 discussed herein can be used in connection with several other types of cardiac harnesses.

The term "cardiac harness" as used herein is a broad term that refers to a device fit onto a patient's heart to apply a compressive force on the heart during at least a portion of the cardiac cycle.

Figure 3:
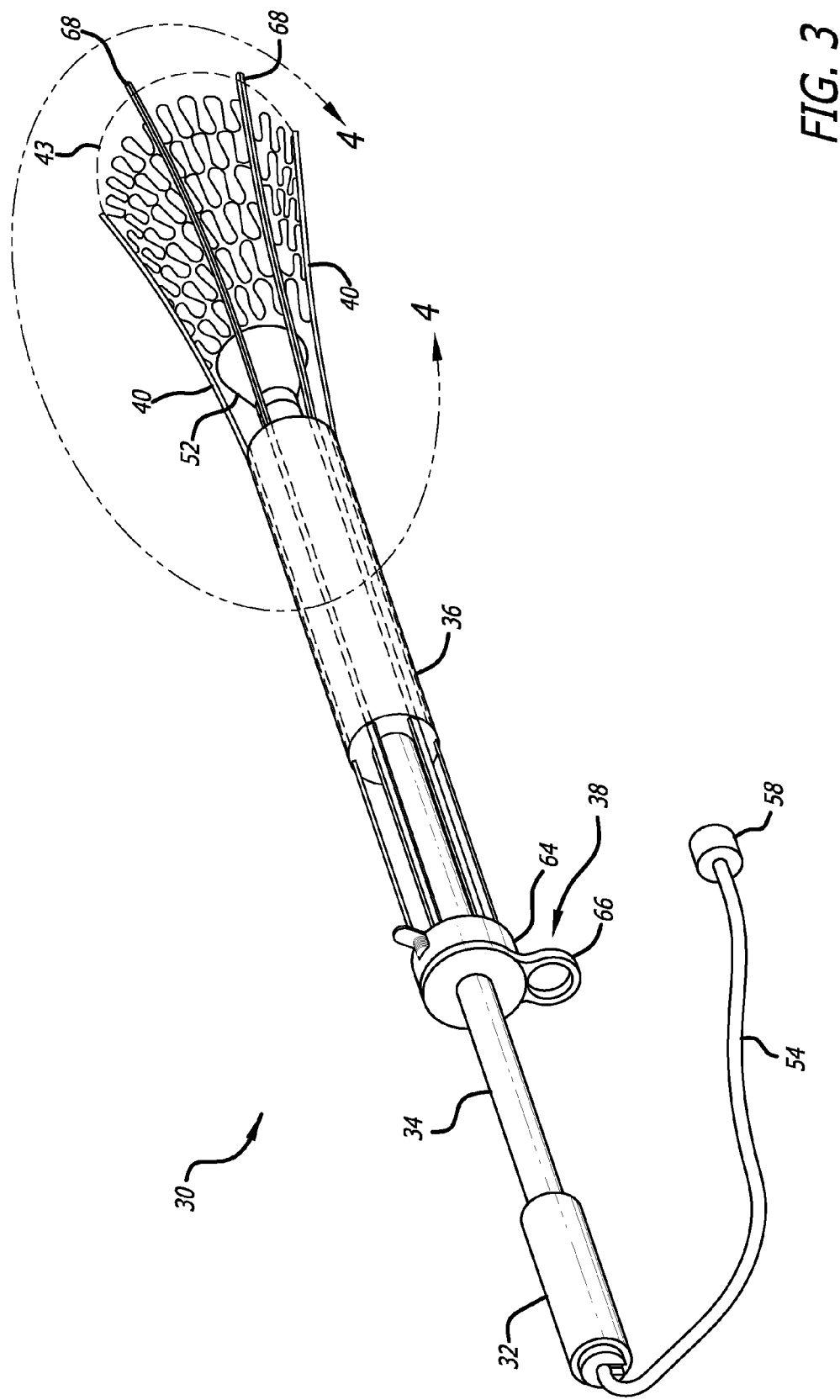
FIG. 3 is a perspective view of the delivery device of FIG. 1 with the movable portion in an advanced position relative to the body portion.
Figure 4:
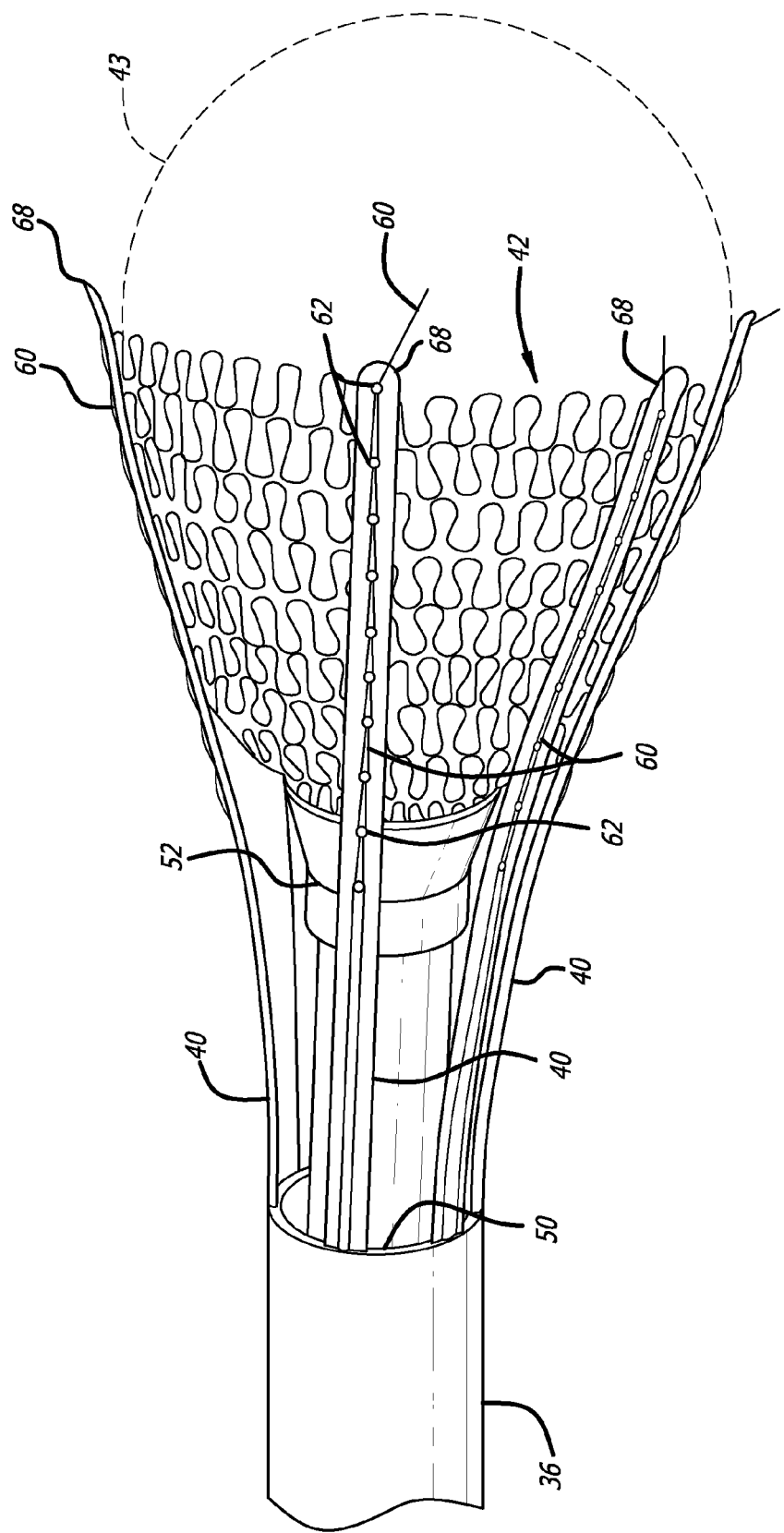
FIG. 4 is an enlarged view of a distal portion of the delivery device of FIG. 1 indicated by line 4-4 of FIG. 3.

The control assembly 38 and plurality of push rods 40 are movable axially with respect to the shaft 34 from the retracted position, as illustrated in FIGS. 1 and 2, to an advanced, or deployed position, as illustrated in FIGS. 3 and 4. Thus, the delivery device 30 is configured to deploy the cardiac harness 42 from a compacted configuration within the housing 36 to an expanded configuration outside of the housing 36 thereby delivering the cardiac harness 42 onto a heart 43 (illustrated schematically in FIGS. 3 and 4), as is described in greater detail below. Delivery of the cardiac harness to the heart and mounting it onto the heart is described in more detail in U.S. Pat. No. 7,189,203, which is incorporated by reference herein.

The handle 32 is fixed to the shaft 34 in the illustrated embodiment. However, it is to be understood that in other arrangements the handle 32 may be movable relative to the shaft 34 along with the control assembly 38. Additionally, another embodiment may not employ a handle 32. Further, with reference to FIG. 1, a stop 39 preferably is provided on the shaft 34. The stop 39 comprises a raised portion that engages the control assembly 38 so that the assembly 38 cannot move distally over the shaft 34 beyond the stop 39. As such, the harness 42 is not advanced too far over the heart 43.

With reference again to FIG. 2, the housing 36 preferably is a relatively thin-walled, tubular member. Desirably, the housing 36 is supported substantially concentric with the shaft 34 to define an interior cavity 44 between an inner surface of the housing 36 and an outer surface of the shaft 34. Preferably, the cavity 44 is sized and shaped to contain the cardiac harness 42 in a compacted configuration therein. The cavity is also referred to herein as a "medical device location."

As indicated above, preferably the device 30 is configured to deliver the cardiac harness 42 in a minimally invasive procedure. Accordingly, a preferred housing 36 has a nominal outer diameter of less than about 5.1 cm (2 inches), more preferably, less than about 3.2 cm (1.25 inches). Preferably, the housing 36 is flexible such that its transverse cross-sectional shape may be collapsed or compressed as needed to advance through a minimally invasive surgical entry path, as described in greater detail below. In the illustrated embodiments, the housing 36 is generally cylindrical in its relaxed or uncompressed condition. It is to be understood that, in another preferred embodiment, the housing is substantially elliptical in its relaxed condition such that the housing may have a cross-section with major axis and minor axis. This configuration may be especially beneficial for advancing the housing through body passages having relatively narrow clearance, such as advancing the housing between the ribs.

With continued reference to FIG. 2, a base portion 46 of the housing 36 preferably defines a closed end of the cavity 44 and supports the housing 36 relative to the shaft 34. The base end 46 may be secured to the shaft 34 by mechanical fasteners, adhesives or other suitable methods apparent to one of skill in the art. In one embodiment, the base end 46 is rotatable relative to the shaft 34. Preferably, the distal end of the housing is open to define an open, distal end of the cavity 44 to permit the cardiac harness 42 to be advanced from the cavity 44.

Preferably, an inner surface of the housing 36 defines a plurality of channels 50 (FIG. 4) extending axially throughout the length of the housing 36. Each of the channels 50 preferably is sized and shaped to slidably receive one of the plurality of push rods 40. Thus, preferably, the number of channels 50 is equal to the number of push rods 40. Further, each channel 50 preferably opens into a cavity 44 along at least a portion of the length of the channel 50.

In the embodiments illustrated, eight push rods 40 and eight channels 50 are provided and are substantially equally spaced around the circumference of the housing 36. A greater or lesser number of push rods 40 and channels 50 may be provided as appropriate to support and deploy a cardiac harness. In an additional arrangement, the channels 50 may be omitted and the push rods 40 may simply be restrained from moving radially outwardly by an outer wall 48 of the housing 36. Other suitable arrangements to guide the push rods 40 and house the cardiac harness 42 may also be used.

With continued reference to FIGS. 1-4, the delivery device 30 preferably includes a positioning arrangement configured to hold the delivery device 30 in a desired position relative to the heart 43. In the illustrated arrangement, the positioning arrangement comprises a suction cup member 52 supported on a distal end of the shaft 34. A tube 54 extends through the shaft 34 and is connected to the suction cup member 52. A distal end of the tube 54 opens into an interior space defined by the suction cup member 52. The proximal end of the tube 54 includes a connector 58 that allows connection of the tube 54 to a pump member such as a syringe or other source of vacuum. Accordingly, once the delivery device is properly positioned, air may be withdrawn from within the tube 54 to create a vacuum condition within the interior space of the suction cup member 52, thereby permitting the suction cup member 52 to securely hold the heart of a patient.

In one embodiment, the tube 54 and suction cup member 52 are not rigidly affixed to the shaft 34 so that the shaft 34 may be moved relative to the tube 54 and suction cup 52. In another embodiment, the shaft 34 and a proximal end of the suction cup 52 are threaded so that the suction cup may be threaded onto the shaft. In still other embodiments, other structure may be used to releasably connect the suction cup to the shaft.

Preferably, the cardiac harness 42 is secured to a distal portion of each of the plurality of push rods 40 by a flexible line that is configured into a releasable stitch, such as described in U.S. Pat. No. 7,189,203, the entirety of which is incorporated by reference herein. Desirably, as shown in FIG. 4, the flexible line 60 passes through a plurality of openings 62 in the distal portion of the push rod 40 and is arranged into a series of interconnected loops that are releasable by actuation of the control assembly 38 in a manner described in greater detail below. Release of the interconnected loops, in turn, releases the cardiac harness 42 from the push rods 40.

With particular reference to FIGS. 1 and 3, the control assembly 38 preferably includes a substantially cylindrical body portion 64 and a release member 66. A portion of the release member 66 preferably is received within a cavity of the body portion 64. An exposed pull portion of the release member 66 extending outwardly from the body portion 64 is generally annular in shape, such that a user of the delivery device 30 can grasp the release member 66 with one or more fingers extending through the a hole defined by the annular shape. As the release member 66 is pulled away from the body portion 64 of the control assembly 38, the release member 66 pulls on the flexible lines 60 such that the interconnected loops of the releasable stitch are unraveled.

Deflector

Figure 6:
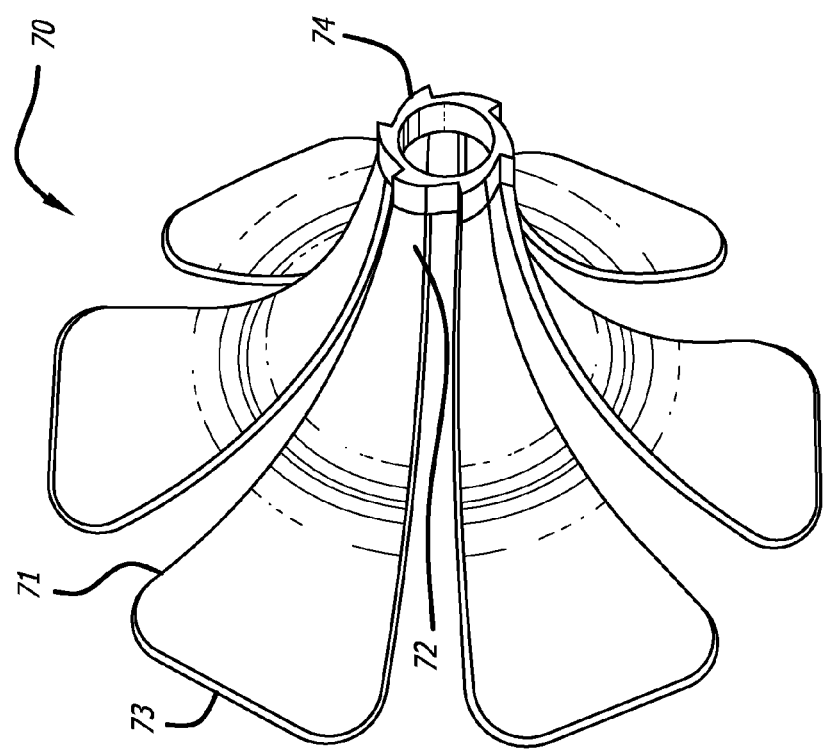
FIG. 6 is a perspective view of a deflector including a plurality of second petals attached to a second ring.
Figure 5:
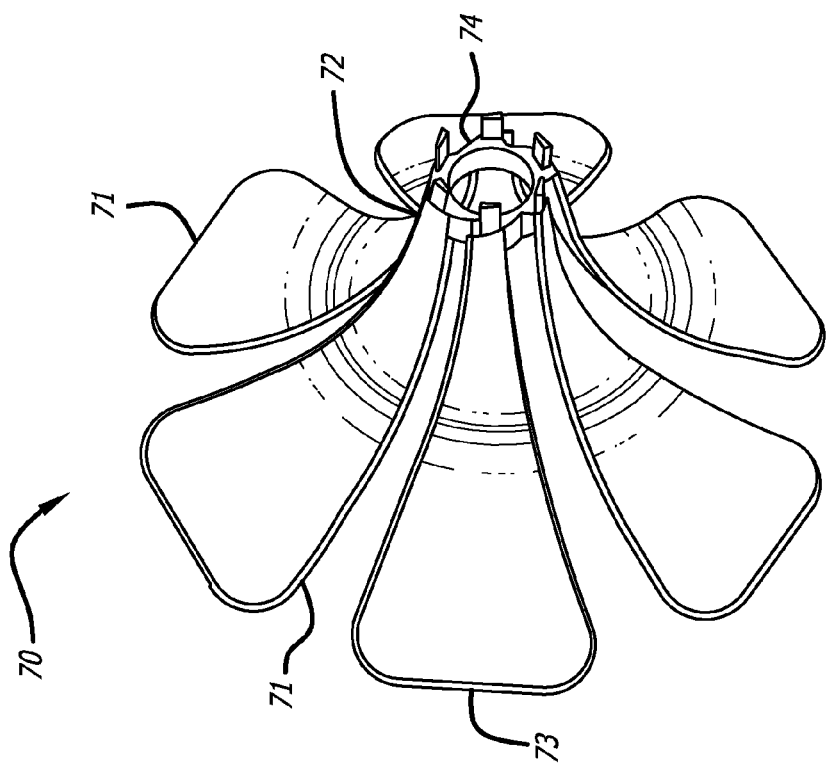
FIG. 5 is a perspective view of a deflector including first petals attached to a first ring.
Figure 7:
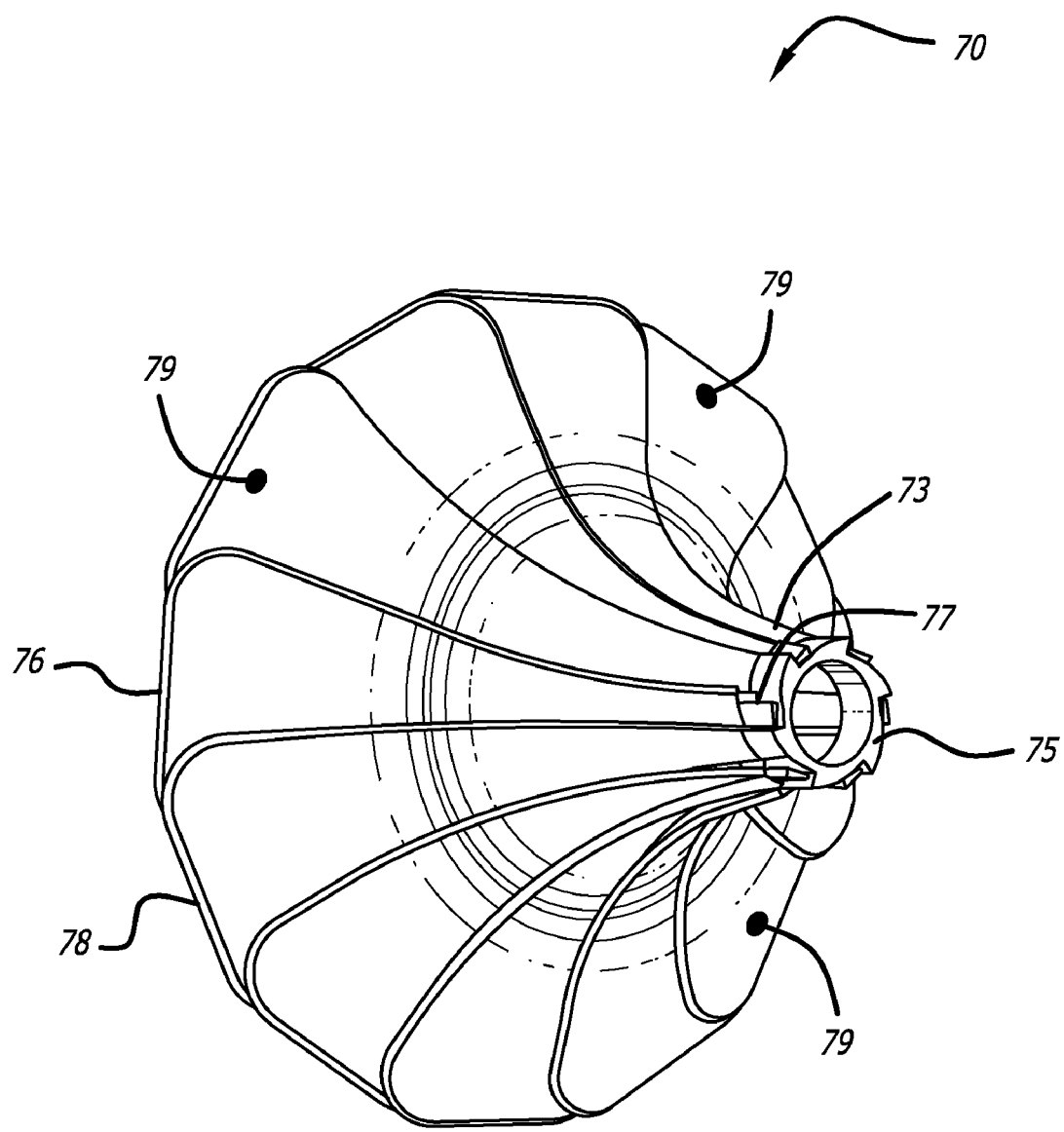
FIG. 7 is a perspective view of a deflector including the first and second petals being interlocked or overlapped with the first ring and second ring interlocked.

In one aspect of the invention, as shown in FIGS. 5-7, a medical device includes a medical apparatus for delivering a cardiac harness onto the heart. The medical device includes a deflector 70 having a number of petals 71 with a proximal end 72 and a distal end 73 and a ring 74, whereby the proximal end of the petals are attached to the ring. Typically the petals 71 will taper from a relatively narrower proximal end to a relatively wider distal end. The petals are flexible so that they can be collapsed into a delivery configuration and are adapted to flare radially outwardly into a deployed configuration. In one embodiment, the cardiac harness is compressed into a tubular housing and releasably attached to push rods that are longitudinally movable relative to the housing. The cardiac harness is advanced out of the housing by the push rods, which engage the deflector so that the distal ends of the push rods are deflected radially outwardly in order to more easily conform to the surface of the heart and to protect the heart from any trauma associated with the advancing push rods.

In another embodiment, as shown in FIGS. 5-7, a medical device includes a deflector 70 having a first ring 75 having first petals 76 attached to the first ring, and a second ring 77 having second petals 78 attached to the second ring 77. The first ring 75 and the second 77 ring are adapted to interlock so that the first petals 76 and the second petals 78 overlap as shown in FIG. 7. Since the first petals 76 and the second petals 78 overlap, and due to the flexibility of the petals, the petals can slidingly engage each other so that they can be compressed into a delivery configuration and will flare radially outwardly into a deployed configuration, as described below. In one embodiment, the deflector 70 is firmly attached to the delivery device 30 by inserting the proximal end of the suction cup 52 through the assembled rings 75, 77 and threading the proximal end of the suction cup 52 onto corresponding threads in shaft 34. Thus, deflector 70 and suction cup 52 are firmly attached to the shaft 34.

In one embodiment, the deflector 70 includes a plurality of petals 71 that number in the range of from four to twenty petals. The petals can be formed of a polymer material, polyamides, polyamide copolymers such as PEBAX (a polyether block amide), silicone rubber, polyurethanes, and nylons. The petals and ring can be injection molded by known techniques. The petals also can be formed from a metallic material, such as nitinol or a combination of a nitinol and polymer webbing. At least some of the petals may be loaded with a radiopaque material to enhance visualization of the device under fluoroscopy, or have a radiopaque material embedded in the petal. For example, radiopaque plugs, beads or wires 79 made from high density metals can be embedded in the petals 71 to enhance the visibility of the petals under fluoroscopy or by other imaging means.

Figure 8:
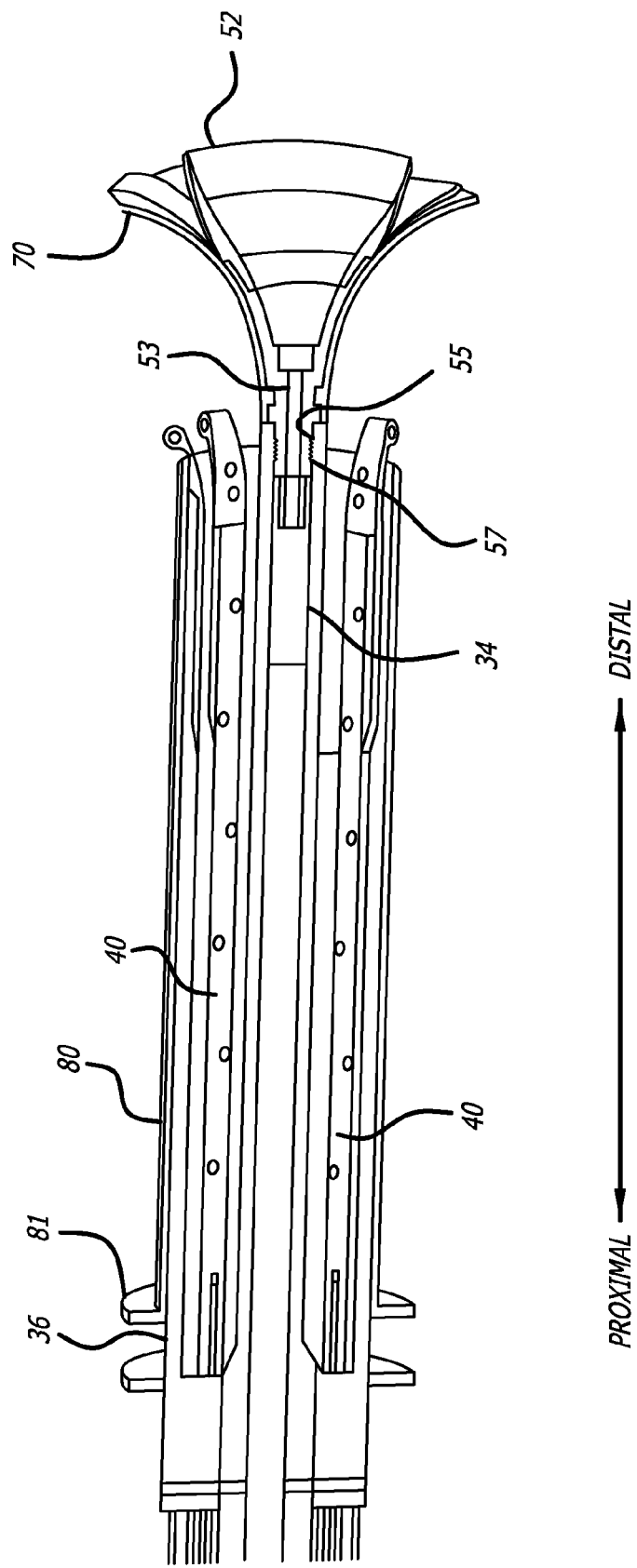
FIG. 8 is a partial, enlarged, longitudinal cross-sectional view of the distal portion of the housing depicting the deflector sheath and an inner deflector.

In further keeping with the invention, as shown in FIGS. 8, 9A, and 9B, the deflector 70 is housed in a deflector sheath 80, which is preferably a clear plastic tube having a flange 81 at its proximal end. Preferably, the deflector 70 is attached to the delivery assembly so that it remains axially stationary during use. In this embodiment, the suction cup 52 has a shaft 53 that extends through the rings 75, 77 of the deflector 70 (FIG. 7). Screw threads 55 on shaft 53 matingly engage screw threads 57 on housing shaft 34 so that the suction cup 52 is screwed onto housing shaft 34 and in the process attaches the deflector 70 over the suction cup 52. The deflector sheath 80 is sized so that it fits over a distal portion of the delivery device 30 and can move axially relative to the delivery device 30 and the deflector 70. In this manner, the doctor can push on the flange 81 in a distal direction so that the deflector sheath 80 can be extended over the deflector 70 thereby compressing the petals 71, 76, 78 into a delivery configuration 82, as shown in FIG. 9B. As the deflector sheath 80 is extended distally over the deflector, the petals 71, 76, 78 slidingly overlap to a smaller diameter until they reach the delivery configuration 82. By pulling back on flange 81 in a proximal direction, the deflector sheath 80 retracts axially over the delivery device 30 so that the deflector 70 emerges from the deflector sheath and the petals 71, 76, 78 slidingly open over each other to flare radially outwardly into a deployed configuration 83 (FIG. 9A). The petals are biased radially outwardly so that they automatically expand radially outwardly as the deflector sheath 80 is moved, or retracted, axially in a proximal direction.

Figure 10:
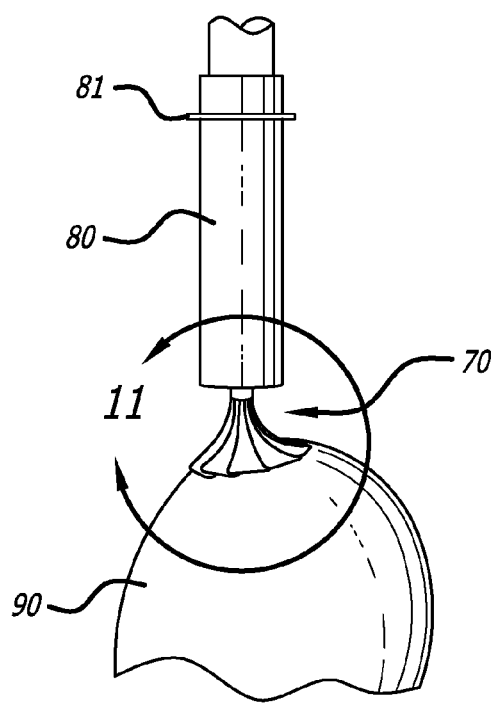
FIG. 10 is an elevational view of a portion of the delivery device depicting the inner deflector in its deployed configuration on the surface of a heart.
Figure 11:
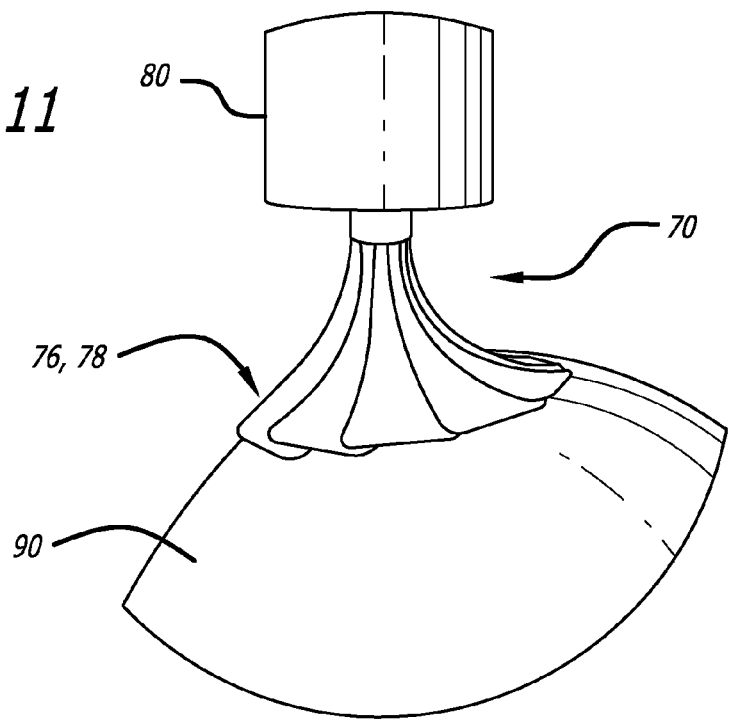
FIG. 11 is an enlarged partial elevational view of the delivery device depicting the inner deflector in its deployed configuration on the heart.

FIGS. 10-18 illustrate the use of a delivery device 30, preferably configured substantially as described above, to deliver a cardiac harness 42 onto a heart 90. Preferably, the delivery device 30 is configured to locate and grasp the heart 90, accurately position the cardiac harness 42 onto the heart 90, and permit withdrawal of the delivery device 30 without disturbing the positioning of the cardiac harness 42. As shown more specifically in FIGS. 10 and 11, the deflector sheath 80 has been withdrawn proximally thereby exposing the deflector 70, which has flared radially outwardly and is in contact with the heart 90 (in this case a schematic representation of the heart). Not visible in FIGS. 10 and 11 is suction cup 52 which is used to securely fasten, via a vacuum, the delivery device 30 to the apex portion 92 of the heart 90. The deflector 70 extends over the suction cup 52.

With reference to FIG. 4, preferably, the suction cup 52 of the delivery device 30 engages an apex portion 92 of the heart 90, which is illustrated schematically in FIG. 4. The distal end of the delivery device 30 may access the heart 90 through any suitable method, but preferably through a minimally invasive procedure. In FIGS. 4 and 10-18, the pericardial sac or pericardium surrounding the heart is omitted for ease of illustration.

A pump device, such as a syringe, is connected to the tube 54 through the connector 58 (FIG. 1). Desirably, the syringe is connected to the tube 54 with the plunger in a compressed position. Once connected, the plunger is retracted to create a vacuum condition within the tube 54 and, thus, within the space defined by the interior of the suction cup member 52. Due to the vacuum condition, the suction cup member 52 grasps the apex 92 such that the heart 90 is held in a desired position relative to the delivery device 30.

With reference next to FIGS. 12-16, once the delivery device 30 has been properly secured to the apex portion 92 of the heart 90, the control assembly may be advanced, relative to the shaft, toward the heart 90. The plurality of push rods 40 are advanced toward the heart 90 with the control assembly thereby advancing the cardiac harness 42 from its compacted configuration within the housing onto the heart 90 in a direction from the apex portion 92 to the base portion 94. As shown, the harness 42 preferably stretches elastically to fit over the heart. However, it is to be understood that a substantially non-elastic harness embodiment can also be delivered by this device.

Figure 12:
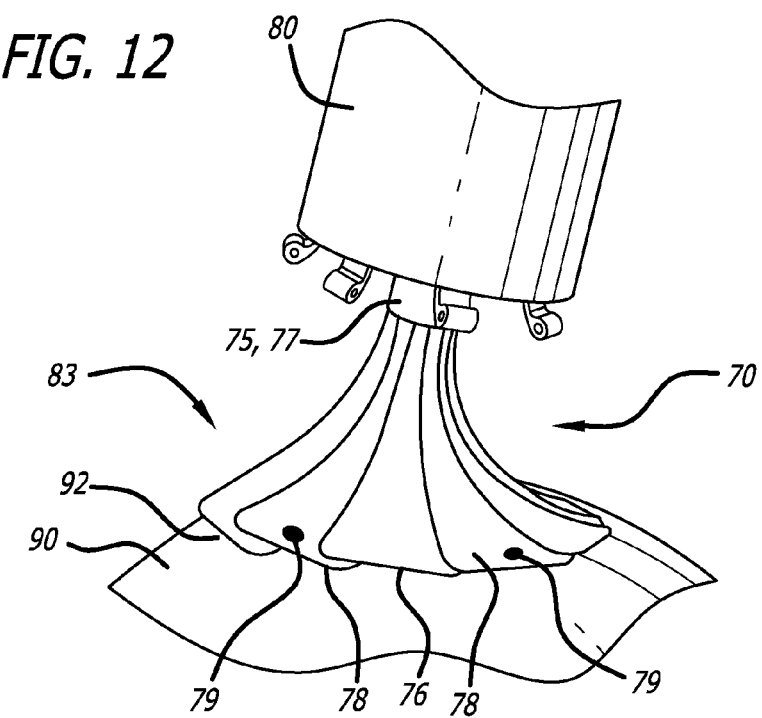
FIG. 12 is an enlarged partial elevational view of the delivery device depicting the inner deflector in its deployed configuration on the heart and the push rods, with the cardiac harness attached thereto, being advanced distally out of the housing.
Figure 13:
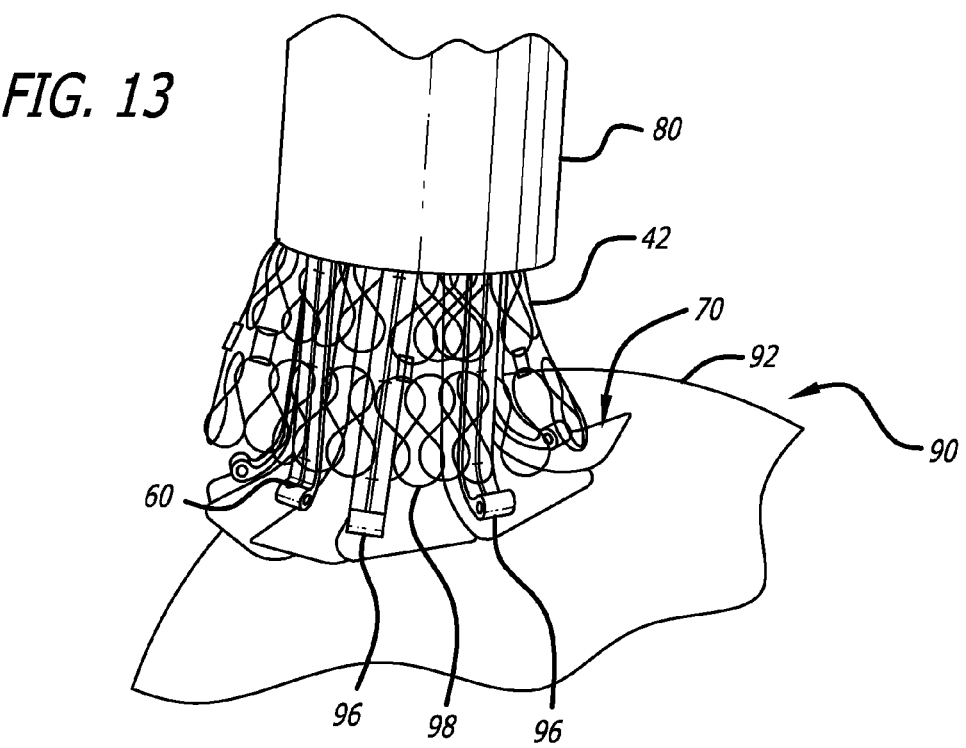
FIG. 13 is an enlarged partial elevational view of the delivery device depicting the push rods advancing distally out of the housing and being deflected radially outwardly by the inner deflector.
Figure 14:
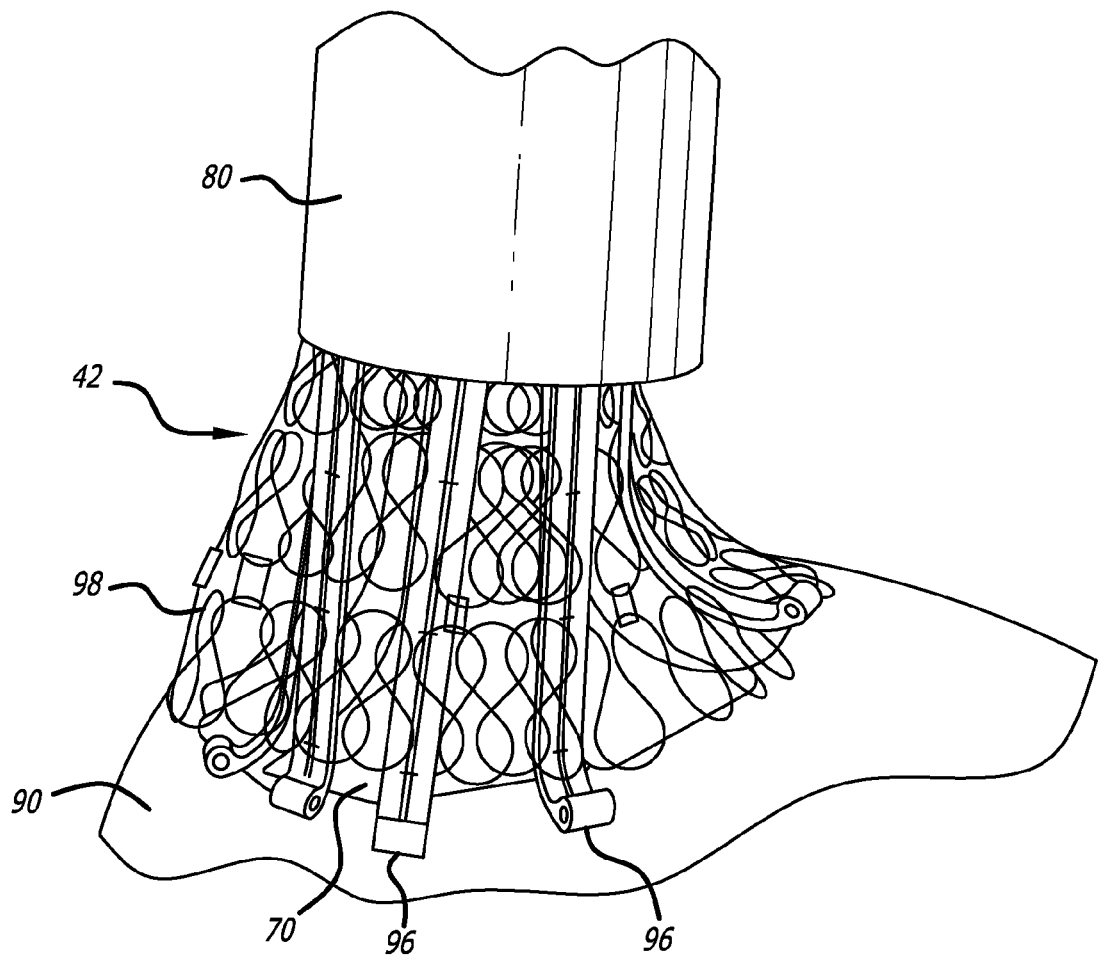
FIG. 14 is an enlarged partial elevational view of the delivery device depicting the push rods further advancing out of the housing and being deflected and guided by the inner deflector as the push rods advance over the heart.

The plurality of push rods 40 splay outwardly to conform to the shape of the heart 90 as they are advanced over the deflector 70. Preferably the tips 96 of the push rods 40 are canted at an outward angle relative to the remainder of the push rod 40 such that contact of the tip 96 with the deflector 70 allows a smooth and atraumatic transition of the push rods 40 onto the heart 90. As shown in FIG. 12, even if the delivery device 30 is off center relative to the apex 92, the deflector 70 will re-direct the push rods 40 to protect the heart tissue and advance the harness onto the heart.

An important feature of the deflector 70 is that as the cardiac harness is advanced from the housing onto the heart, the deflector 70 prevents the first rows 98 of the cardiac harness 42 from catching on the heart and either flipping under or flipping over thereby causing an undesirable configuration for advancing the harness. Further, the deflector 70 also prevents the push rods 40 from prolapsing or collapsing due to the severe delivery angle as the push rods are advanced distally over the apex 92 of the heart.

Figure 15:
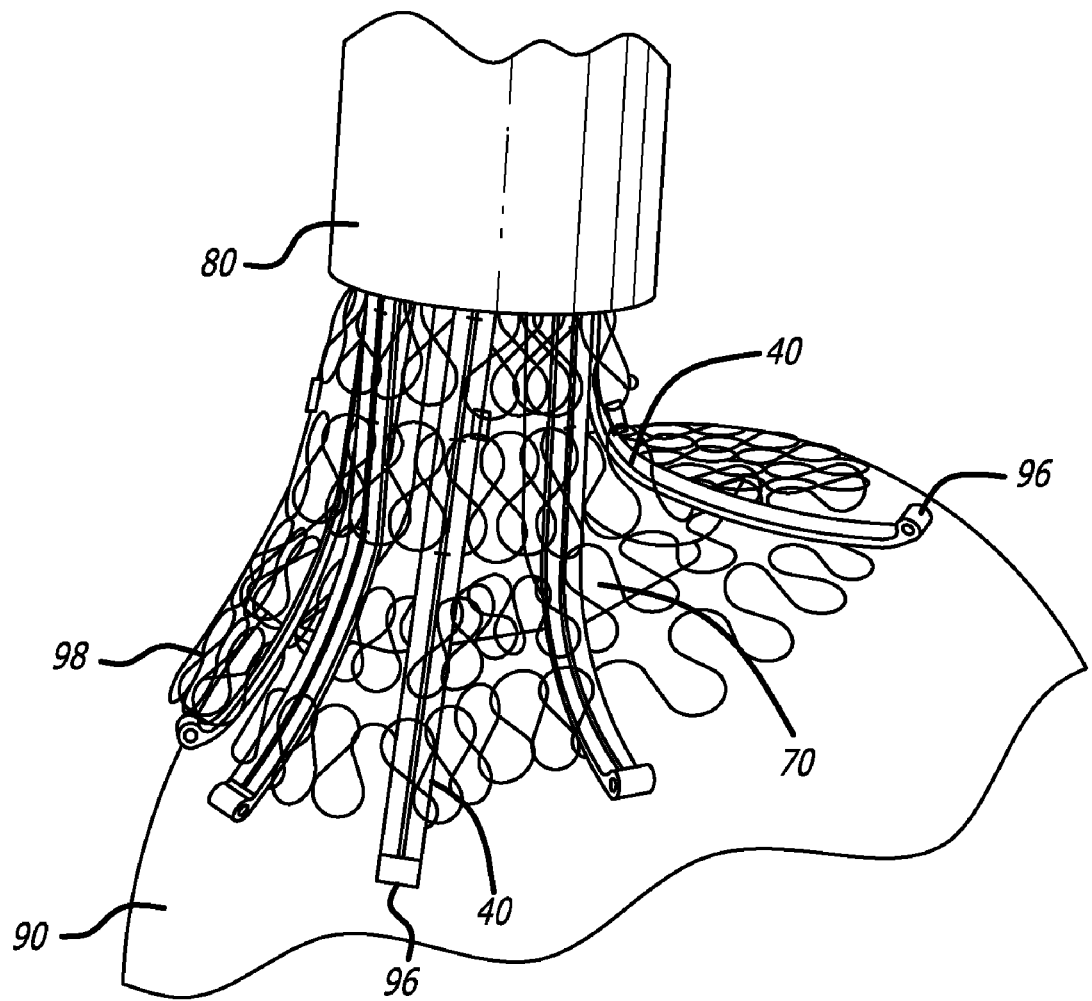
FIG. 15 is an enlarged partial elevational view of the delivery device depicting the push rods further advancing over the inner deflector and over the surface of the heart, and thereby advancing the cardiac harness over the heart.
Figure 16:
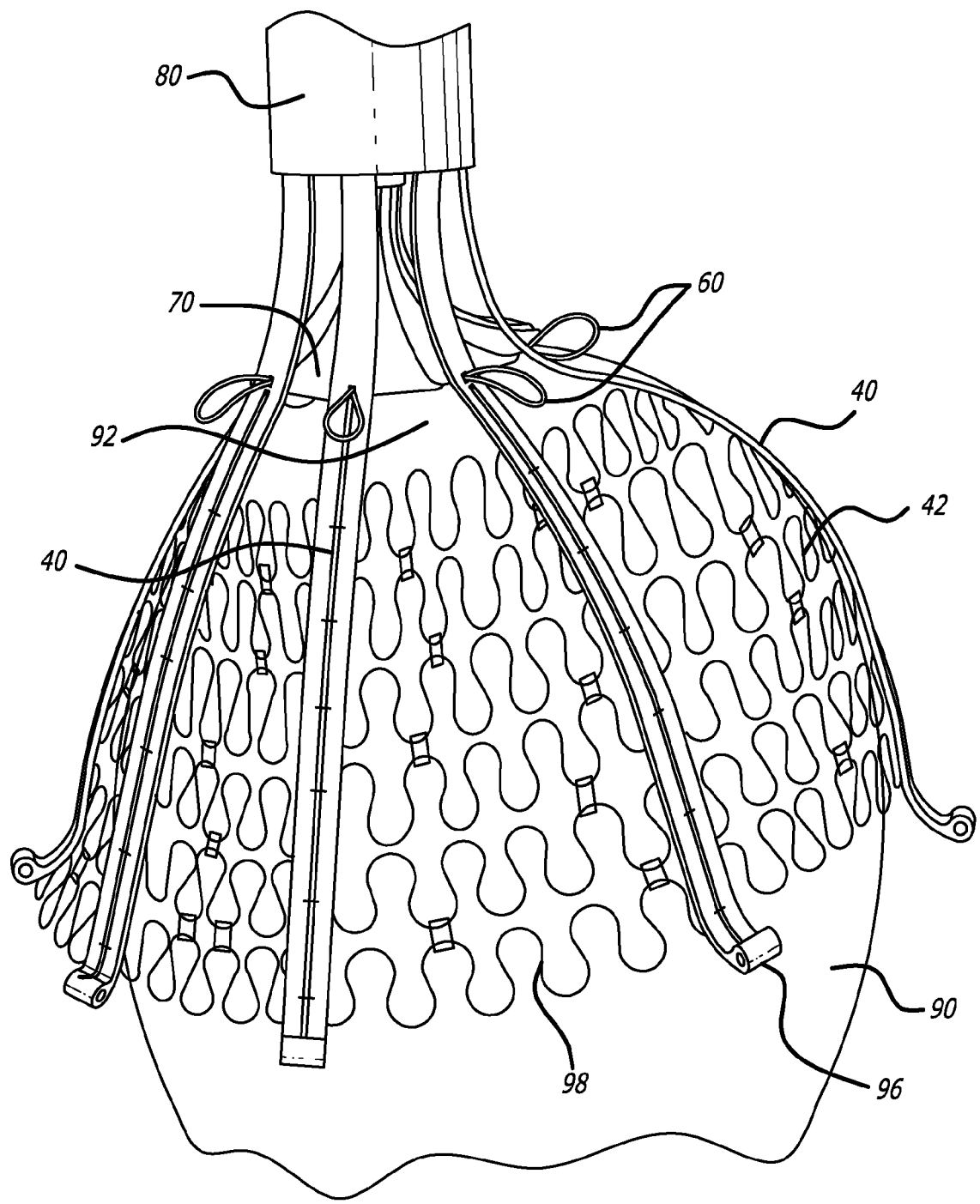
FIG. 16 is an enlarged partial elevational view of the delivery device depicting the push rods further advancing over the inner deflector and over the heart to advance the cardiac harness over the heart.

With reference to FIGS. 15 and 16, the control assembly continues to be advanced until the cardiac harness 42 is properly positioned on the heart 90. Once the cardiac harness 42 is properly positioned, the release member is pulled away from the body portion of the control assembly so that the cardiac harness 42 is released from the push rods 40.

Figure 17:
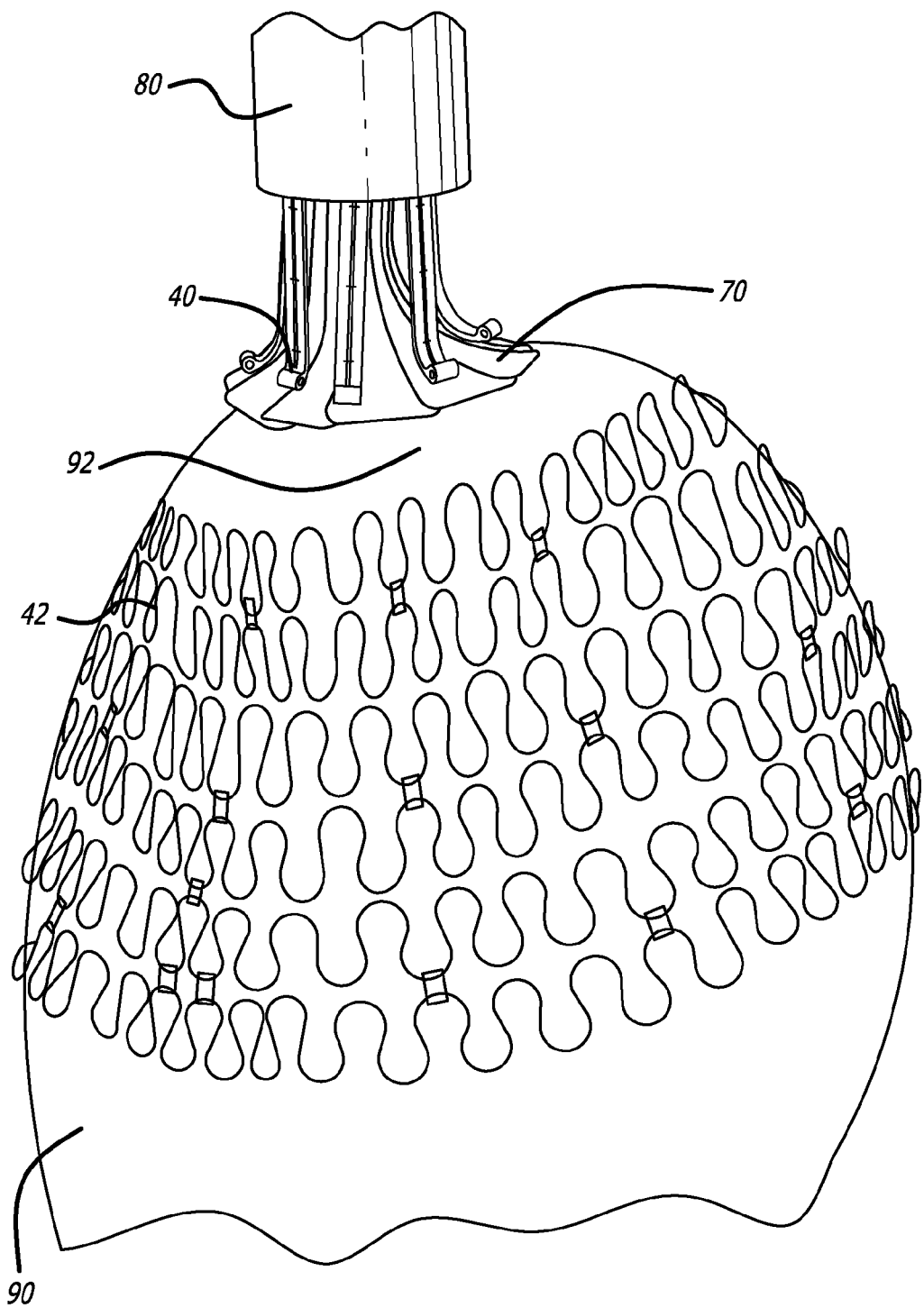
FIG. 17 is an enlarged partial elevational view of the delivery device depicting the push rods being withdrawn proximally into the housing over the inner deflector.
Figure 18:
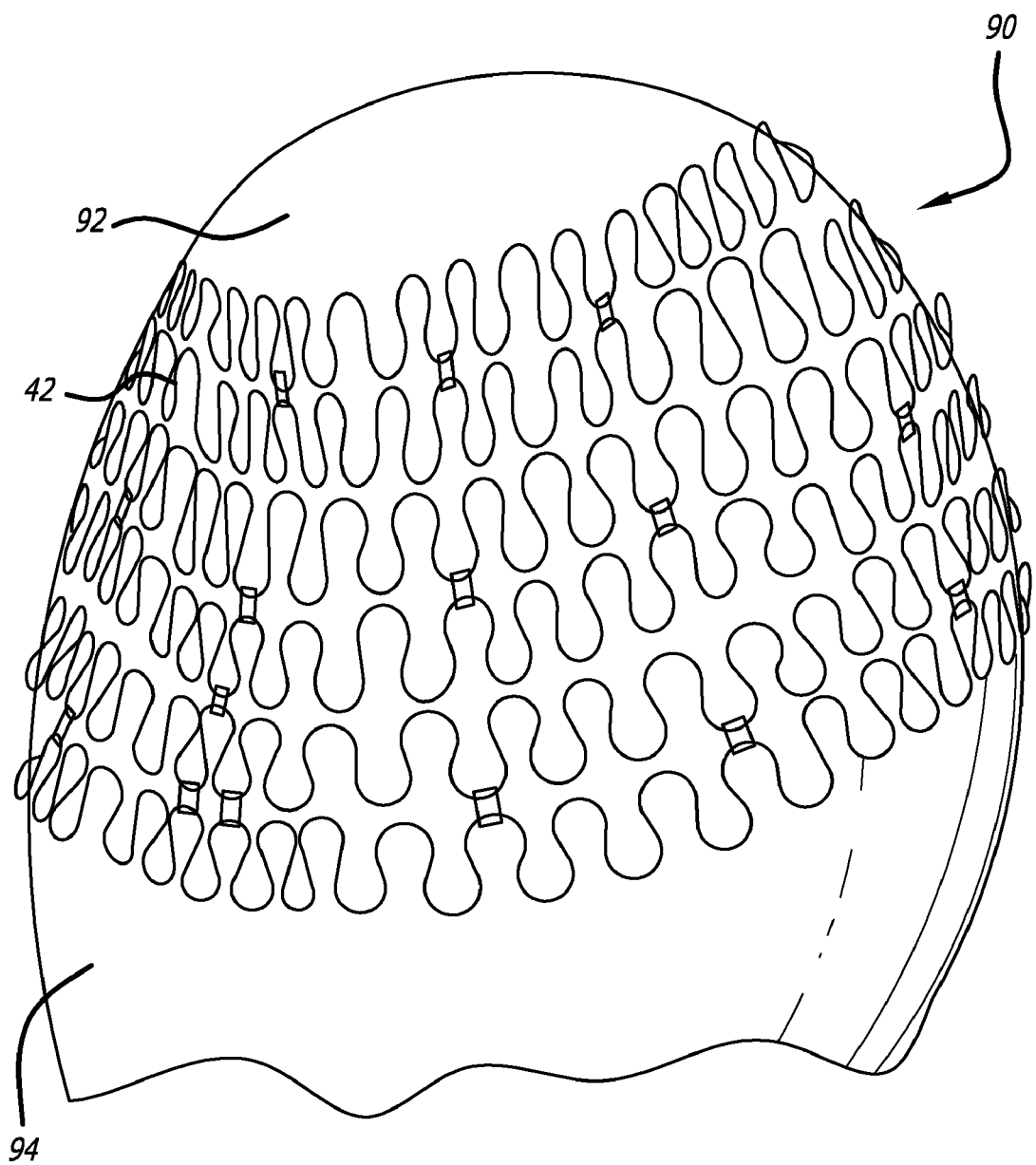
FIG. 18 is an elevational view of the heart depicting the cardiac harness mounted onto the heart and the delivery device being withdrawn.

With reference to FIGS. 17 and 18, once the cardiac harness 42 has been released from the plurality of push rods 40, the generally-elastic harness preferably contracts onto the heart. The control assembly is then retracted relative to the shaft to retract the plurality of push rods 40 from the cardiac harness 42, which remains on the heart 90. As noted above, preferably, the push rods 40 are configured such that retraction of the push rods 40 does not tend to pull the cardiac harness 42 from its desired position on the heart 90. Specifically, in the illustrated embodiment, the outwardly canted tips 96 of the push rods 40 help prevent the push rods 40 from exerting a pulling force on the cardiac harness 42. Once the plurality of push rods have been fully retracted from the cardiac harness 42 and the heart 90, the one-way valve 53 within the connector 58 may be opened to release the vacuum condition within the suction cup member 52. As a result, the delivery device 30 may be removed from the heart 90, as the suction cup member 52 is no longer grasping the heart 90. Thus, the delivery device 30 is retracted from the heart, leaving the cardiac harness 42 in place.

Figure 19:
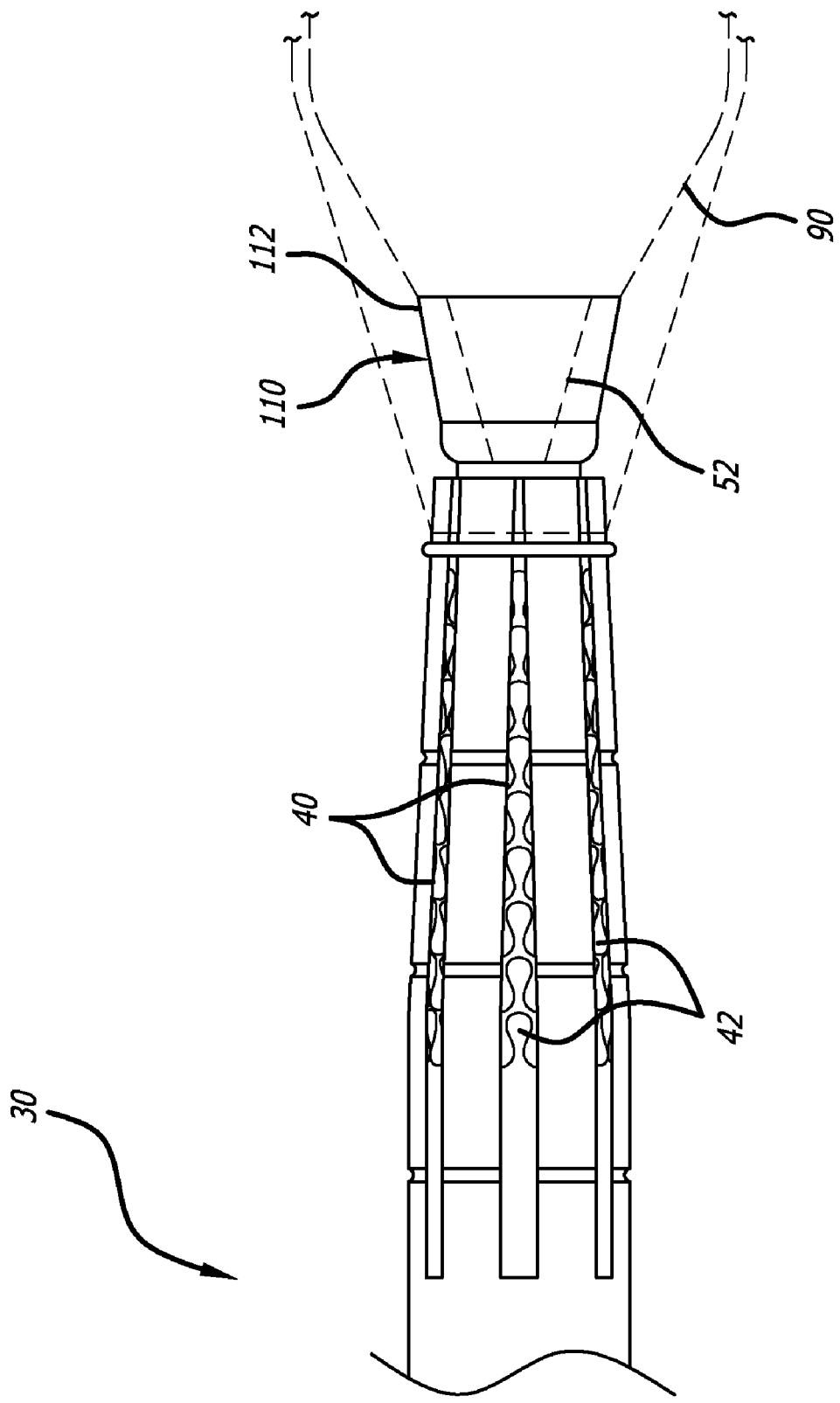
FIG. 19 is an enlarged partial view of the distal portion of the delivery device depicting the inner deflector having a flexible cone.
Figure 20:
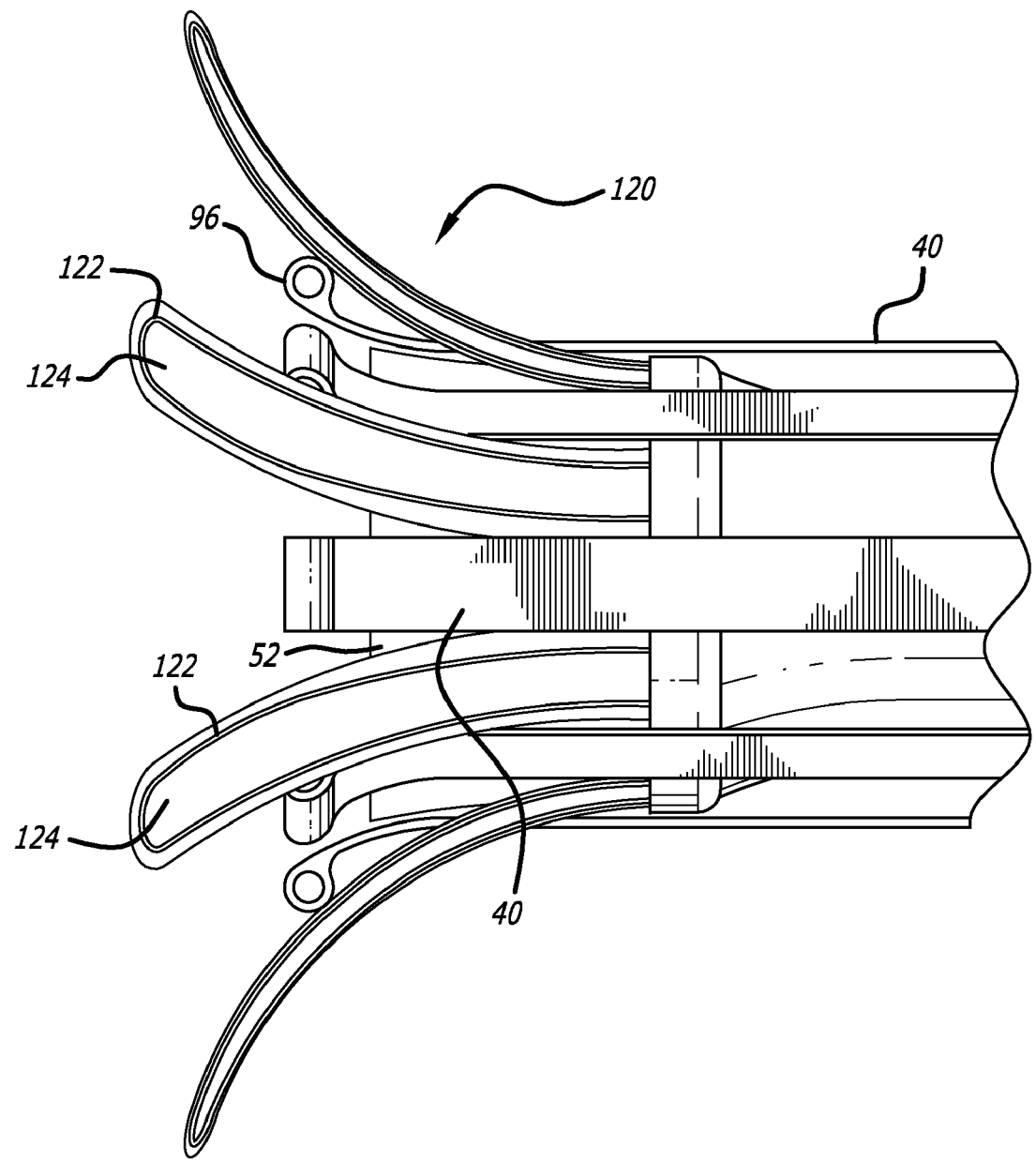
FIG. 20 is an enlarged partial view of the distal portion of the delivery device depicting a deflector having wire form petals bridged by a flexible webbing.
Figure 21:
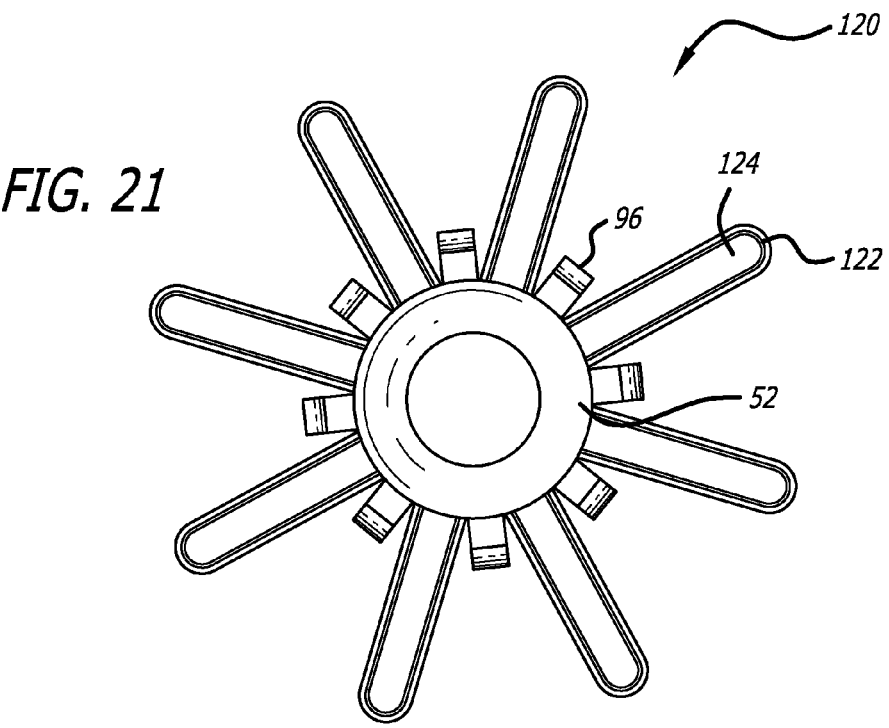
FIG. 21 is an enlarged end view of a distal portion of the delivery device depicting a deflector having wire form petals bridged by a flexible webbing and showing the push rods clocked in relation to the wire form petals.
Figure 22:
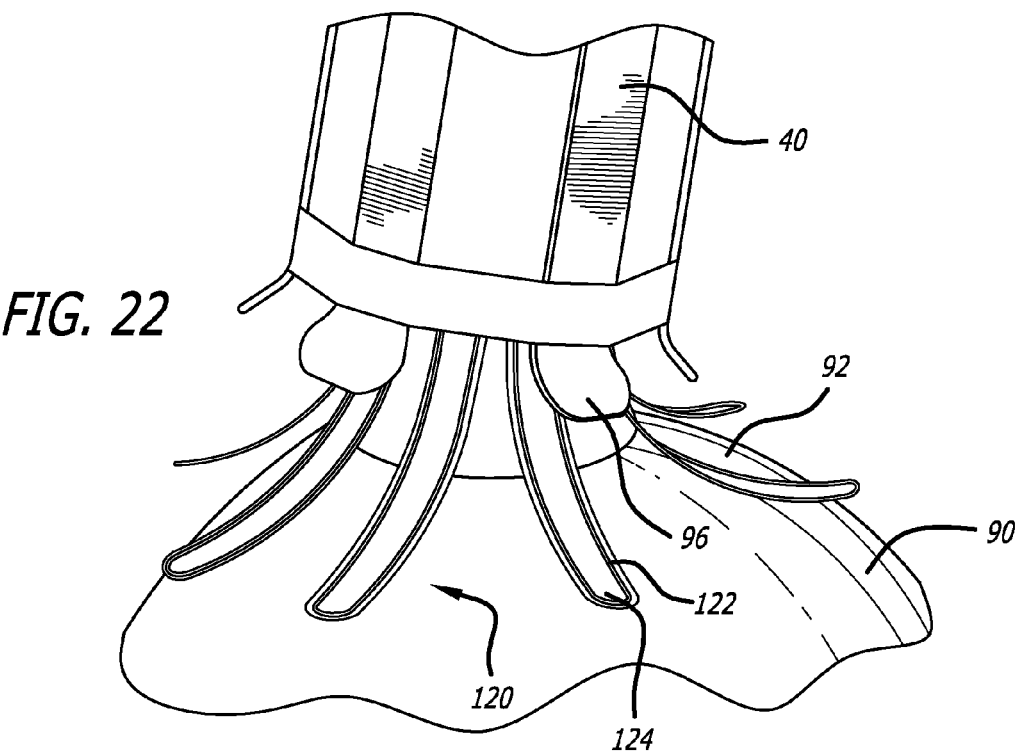
FIG. 22 is an enlarged partial view of the distal portion of the delivery device depicting an inner deflector engaging the apex of the heart.

An alternative embodiment of the deflector is shown in FIGS. 19 and 20-25. With reference to FIG. 19, deflector 110 is substantially similar to the deflector previously described with reference to FIGS. 5-18. Deflector 110 includes a flexible cone 112 that flares radially outwardly, but does not have petals like the previously described deflector. In this embodiment, the flexible cone 112 fits over the suction cup 52 and is a substantially solid material formed from any of the polymers previously described such as PEBAX, silicone rubber, polyurethane, or nylons. As previously described, a deflector sheath 80 (not shown) is extended over the deflector 110 to compress it into a delivery configuration. Because the flexible cone 112 is somewhat compliant, it will collapse and wrinkle up to compress into a delivery configuration. When the deflector sheath 80 is retracted proximally, the deflector 110 will expand radially outwardly and return to its flexible cone 112 configuration in order to assist in the delivery of the cardiac harness as previously described.

Figure 23:
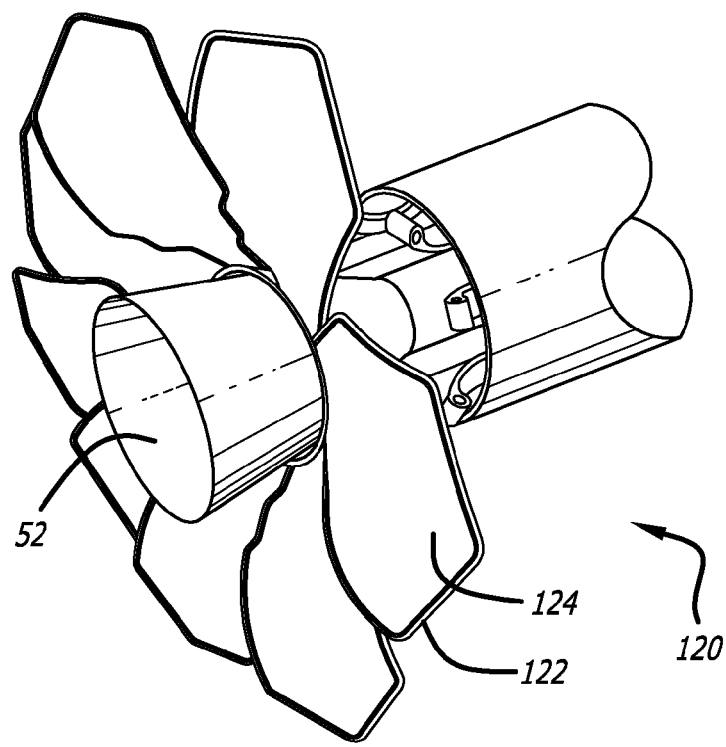
FIG. 23 is an enlarged partial view of the distal portion of the delivery device depicting an inner deflector having large, overlapping wire form petals bridged by a flexible webbing.
Figure 24:
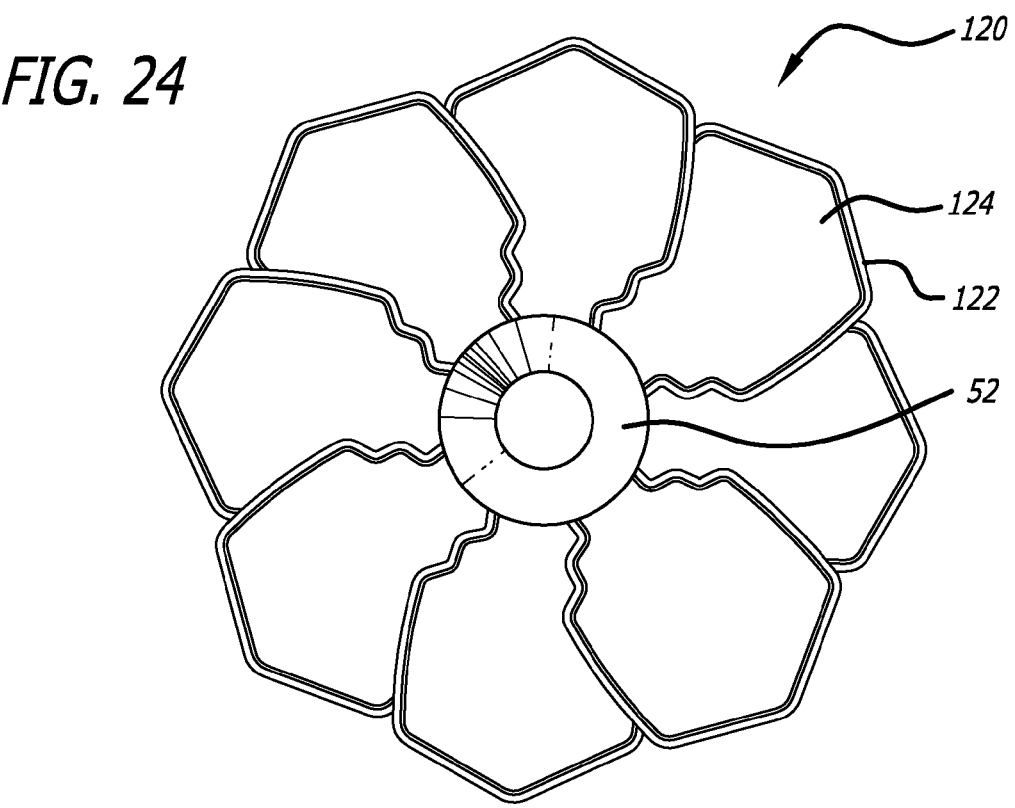
FIG. 24 is an enlarged end view of the distal portion of the delivery device depicting an inner deflector having large, overlapping wire form petals bridged by a flexible webbing.
Figure 25:
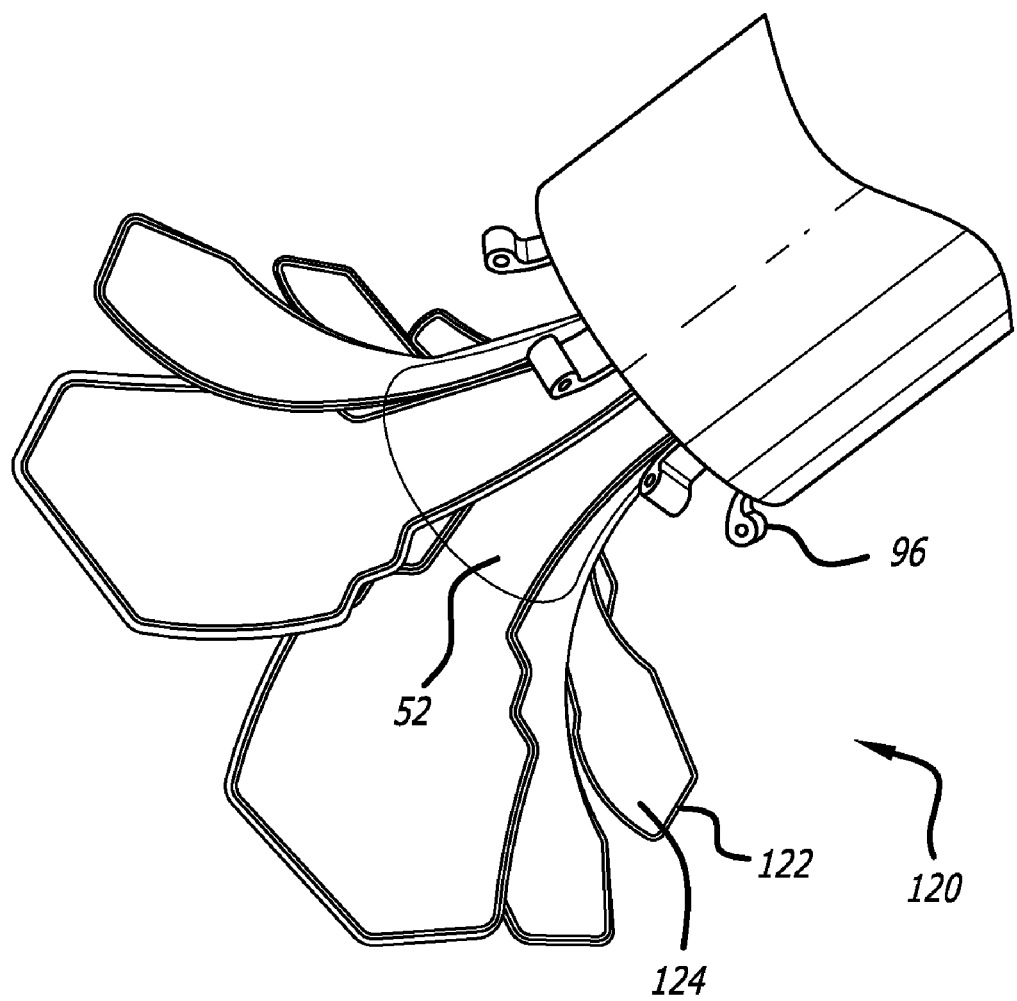
FIG. 25 is an enlarged view of the distal portion of the delivery device depicting an inner deflector having large, overlapping wire form petals bridged by a flexible webbing.
Figure 26:
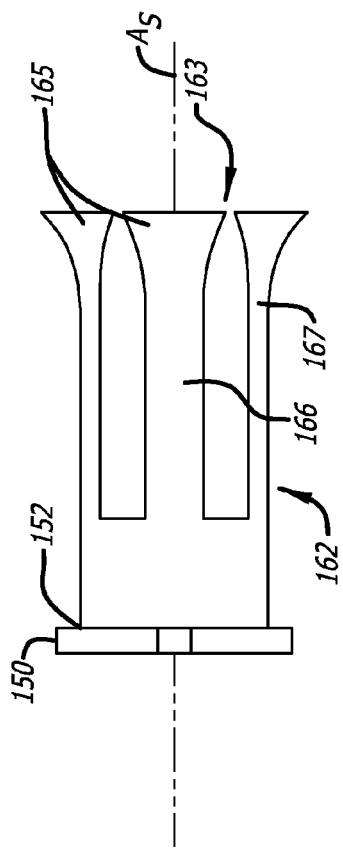
FIG. 26 is a diagram of an introducer usable to establish a pathway to a medical site and to hold tissue away from the site for delivery of a medical device with its strips having flared portions at distal ends.
Figure 27:
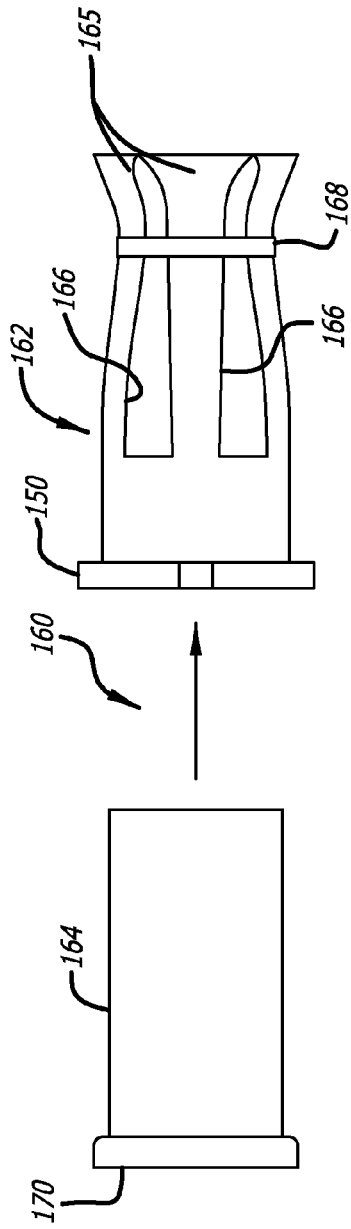
FIG. 27 is a view of the introducer of FIG. 26 having a biasing device, in this case an elastic band, disposed to collapse the strips with flared ends to a smaller diameter so that the introducer may be delivered to the site through an incision, the figure also showing a dilator tube to the left side which has a slightly smaller outer diameter so that it may be slid inside the introducer.
Figure 28:
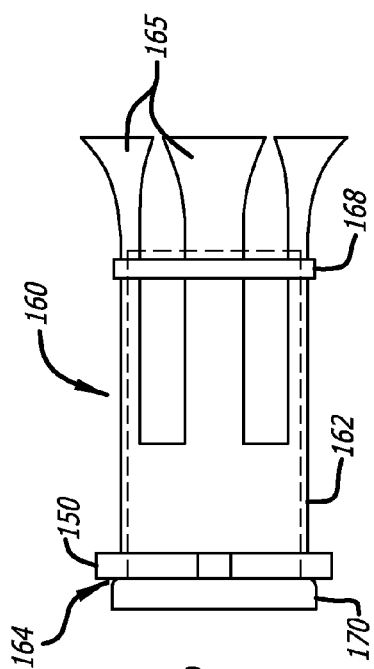
FIG. 28 is a diagram showing the dilator tube inserted fully into the introducer for use in expanding the flared portions of the introducer to a deployed configuration into engagement with tissue once the introducer is in position at the medical site.

In another embodiment of the deflector, as shown in FIGS. 20-25, a deflector 120 is comprised of a number of wire form petals 122 shaped in a hairpin shape or similar shape and flared radially outwardly. The wire petals have a flexible webbing 124 that includes any type of polymer material previously described. In this embodiment, a 0.015 inch (0.381 mm) diameter, nitinol, shape set wire can be used to form wire petals 122 to support webbing 124. The webbing 124 can be coated or molded onto the wire petals 122 in any known manner. Deflector 120 operates similar to that discussed above for the embodiments in FIGS. 5-18. In this embodiment, the push rods 40 are clocked to correspond to the spaces between wire form petals 122. As the cardiac harness is advanced out of the delivery device as previously described, the tips 96 of the push rods will extend into the spaces between the wire form petals 122 so that the cardiac harness will engage and slide along wire form petals 122 and webbing 124 thereby deflecting radially outwardly to provide a smooth transition onto the surface of the heart. As shown in FIGS. 23-25, the wire form petals 122 overlap, similar to that shown in FIGS. 5-18.

As discussed above, the housing 36 may have a collapsible cross-sectional shape. To facilitate insertion of the delivery device 30 through a minimally invasive surgical entry path, the distal end of the housing may be compressed or collapsed. To facilitate advancement through a narrow passage in a minimally invasive surgical entry path, such as between two ribs of a patient, the housing may be flattened to an oval or substantially elliptical cross-section with a minor axis and major axis. Likewise, the deflector sheath 80 and the deflector 70 also can be formed of a compressible material and be collapsed along with the distal end of the housing to facilitate advancement through a narrow passage in a minimally invasive surgical entry path, such as between two ribs of a patient. As the housing 36 and deflector sheath 80 and deflector 70 are advanced past a narrow passage, they can return to a circular cross-sectional shape and portions of the housing adjacent to the narrow passage flatten to allow further advancement of the housing. It will be appreciated that, compared to a rigid housing, a housing with a collapsible cross-section shape places less stress on tissues and bones along the minimally invasive surgical path and, thus, is likely to result in lower incidence of injury or trauma.

It is to be understood that other cross-sectional shapes may be achieved by compressing a collapsible housing. With any cross-sectional shape, when it is desired to advance the housing between two ribs or other narrow passage of a minimally invasive surgical entry path, the minimum cross-sectional dimension is preferably less than a distance across the narrow passage.

While the illustrated embodiments shown in FIGS. 10-25 have a housing with flexible push rods separated by gaps, it will be appreciated by persons of skill in the art that other housing structures may be used resulting in a collapsible cross-sectional shape. For example, it is contemplated that a housing may comprise a thin-walled sleeve configured to fold or stretch along a length of the sleeve.

Although the delivery device 30 is especially well suited for use in a minimally invasive delivery procedure, the device 30 may also be used for open chest procedures, wherein the sternum of the patient is split to provide access to the heart 90. In addition, although the device 30 described herein utilizes a plurality of push rods 40, other suitable structures may also be used to support the cardiac harness 42 when being advanced over the heart. For example, an expandable sleeve can serve as a support structure. Furthermore, it is to be understood that a cardiac harness 42 may be releasably supported in an expanded, or substantially expanded, configuration to a variety of support structures by the releasable stitch referred to herein, or by a similar releasable stitch arrangement.

In the embodiments disclosed herein, the illustrated cardiac harness 42 is formed of several rows of elastic elements. The illustrated harness comprises undulating wire arranged in several adjacent rings, each of which comprises an elastic row. As illustrated, the harness 42 is releasably attached to the push rods by a stitch being wound around some or all of the rows. Of course, it is to be understood that aspects of the present invention can be employed with harnesses having different structure than the illustrated harness, which is included for example only. For example, any harness having one or more openings that could accommodate the releasable stitch could be used such as, for example, a harness formed of a woven or non-woven fibrous material and/or a harness formed of a mesh, honeycomb or other type of material.

Paired Inner and Outer Deflectors

Figure 32:
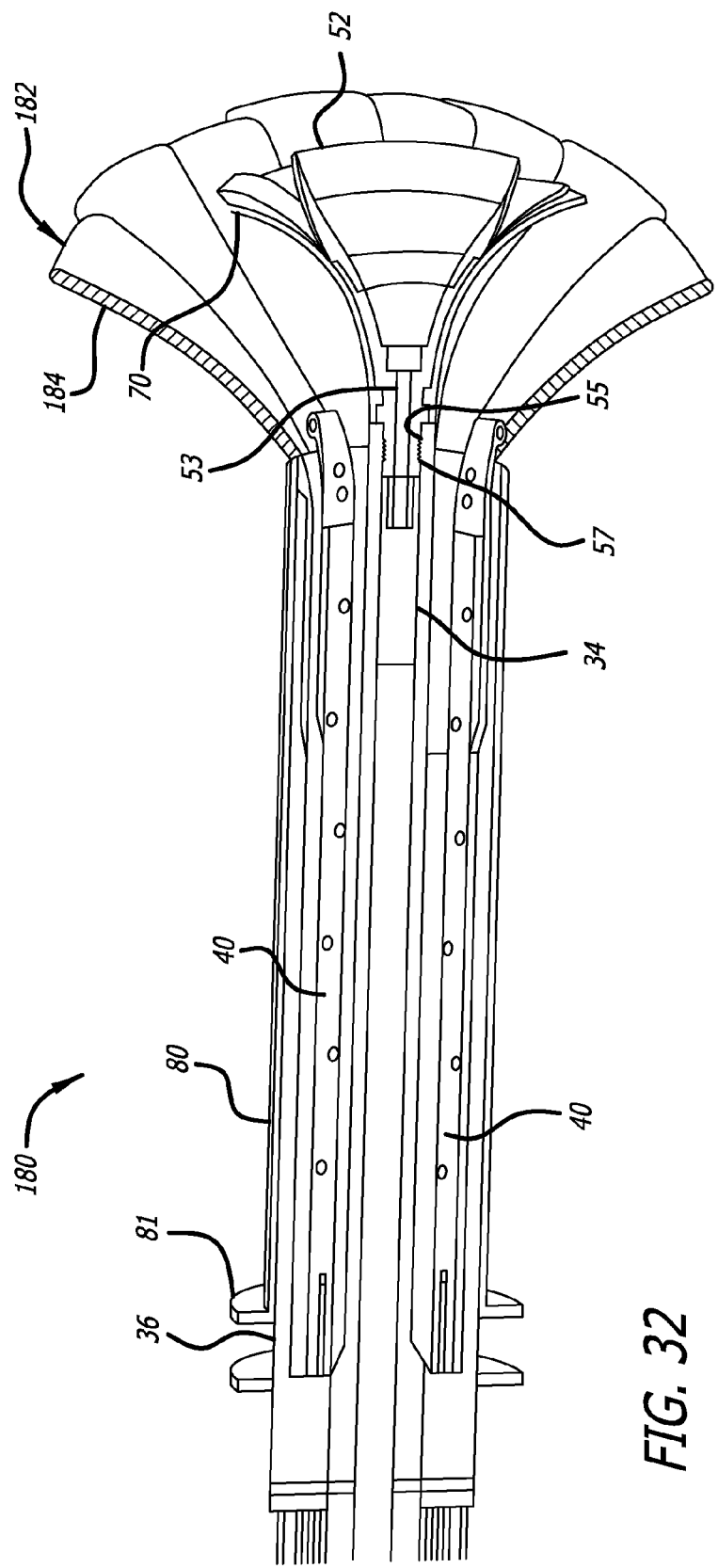
FIG. 32 is a view of a delivery device having two deflectors, an outer deflector for engaging first tissue, such as the pericardium, for providing access to the heart, and an inner deflector for protecting second tissue, in this case the heart, and guiding a cardiac harness into place over the heart, the figure showing both deflectors in the deployed configurations.

Turning now to FIG. 32, there is shown a delivery device 180 having paired deflectors that enables introducer-less implant deployment. The paired deflectors comprise an outer deflector 182 and an inner deflector 70. The inner deflector is as described in detail in conjunction with other figures above. The outer deflector permits the delivery device 180 to take the place of the introducer 160 shown in FIGS. 26 through 31 in that it flares outwardly in a trumpet shape to engage the pericardium. In use, the outer deflector 182 will press upon and open the incision and the surrounding portion of the pericardium so as to create a space between the pericardium and the heart for deployment of the cardiac harness. Further, the flared portions 184 of the outer deflector will function as a lock to resist pulling the delivery device 180 out of the incision. Accordingly, the delivery device 180 is effectively locked in place between the heart and the pericardium surrounding the heart.

In one embodiment, the outer deflector 182 also comprises a plurality of petals flared outwardly into a trumpet shape. These petals may be overlapped or "shingled," as with the inner deflector (see FIGS. 7, 10, and 11), or have a single layer. The material chosen would need to be stiff enough to retain the trumpet shape while under the pericardium, but soft enough to be collapsed and introduced into the pericardial space without causing trauma to the underlying heart tissue. The tips of the petals could have varying radii to tailor the amount of grip on the pericardium. In one embodiment, the tips have a tighter "ski-tip" radius than the trumpet shape for greater pericardial purchase (FIG. 38). Also, the petals could have varying thicknesses from the root (proximal end) to the tip (distal end) of the petal, again to optimize the flexibility/stiffness of the outer deflector. In order to ensure a reasonable collapse force, the width of the petals could also be optimized. Finally, the number of petals can be varied, again to balance collapse force with pericardial retention. Such features are shown in FIGS. 32 through 41.

FIG. 33 presents a view of the distal end of the delivery device 180 similar to that of FIG. 9A except that both inner and outer deflectors are shown. In this case, the cylindrical deflector compression sheath 80 is movably mounted over the housing 36 and has an inner diameter just larger than the outer diameter of the housing to support sliding movement of the compression sheath along the housing in the longitudinal or axial directions. As is also shown in FIG. 32, the deflector sheath 80 has been slid in the proximal direction to the deployment position so that the outer 182 and inner 70 deflectors deploy. In FIG. 33, the deflector compression sheath has been slid in the distal direction somewhat and has partially collapsed the outer deflector 182 and inner deflector 70. As in the previous embodiment of a single deflector, the outer sheath when slid to its limit in the distal direction, will completely collapse the inner and outer deflectors, as shown in FIG. 34. Although not shown, a suction cup is also disposed at the distal end of the delivery device 180, which can be seen in FIGS. 1 through 4.

Figure 35:
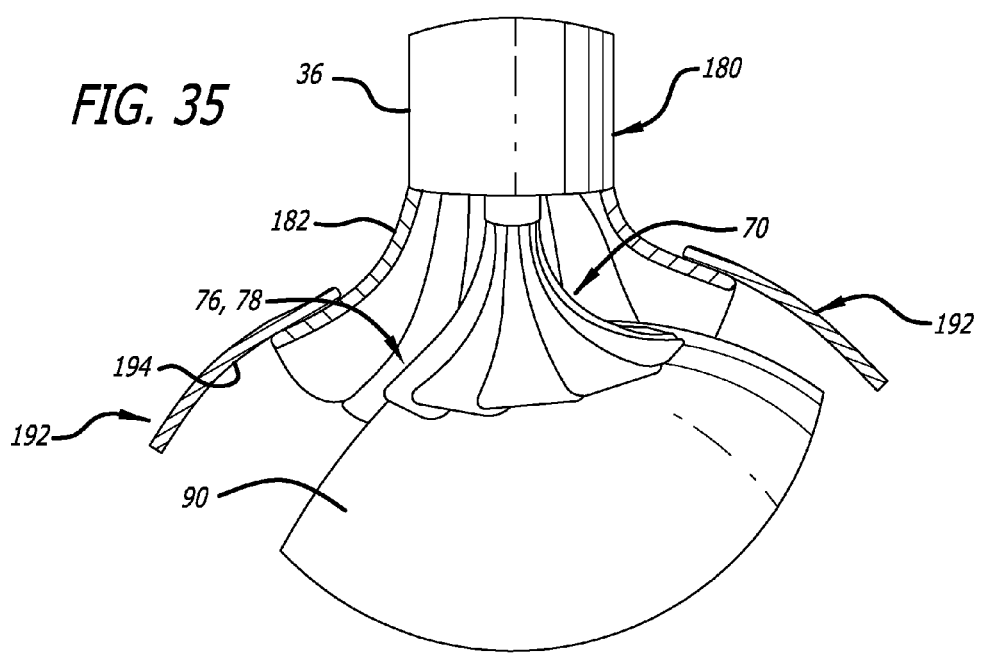
FIG. 35 is a view of the inner and outer deflectors deployed such that the outer deflector has engaged the pericardium and is holding it away from the heart while the inner deflector has engaged the apex of the heart.
Figure 36:
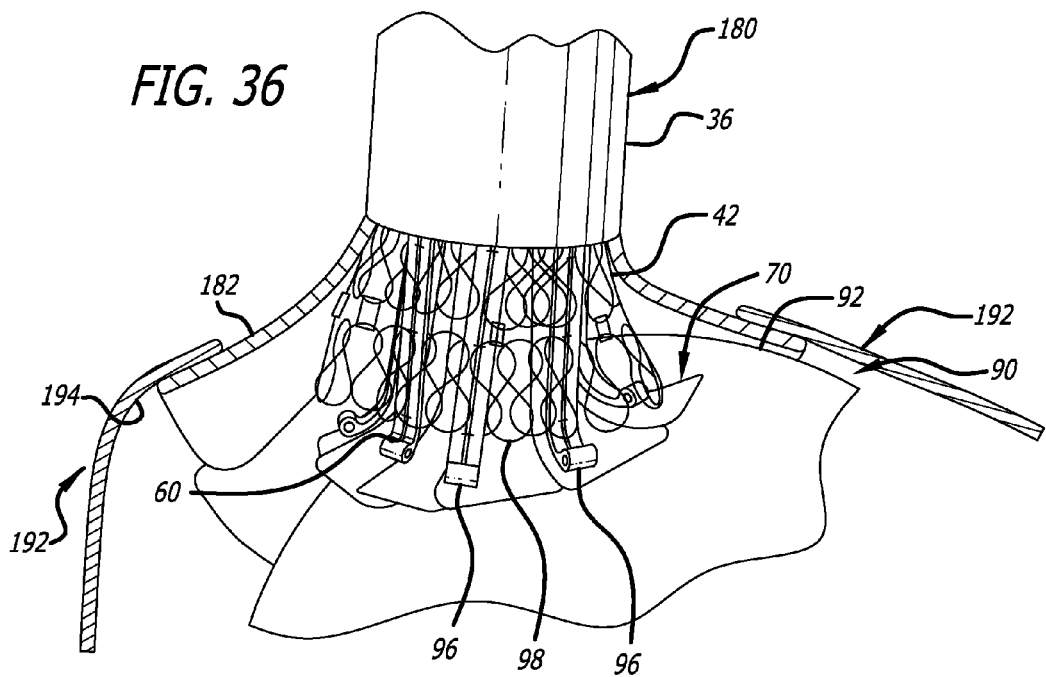
FIG. 36 is a view of deployment of the cardiac harness that was contained by the delivery apparatus housing, showing the harness being deployed under the outer deflector and over the inner deflector, the inner deflector guiding the harness over the heart and protecting the heart at the same time.

Referring now to FIGS. 35 and 36, the outer 182 and inner 70 deflectors have been deployed. The outer deflector has been deployed into contact with a first tissue, which in this case is the inner surface 194 of the pericardium 192 while the inner deflector has been deployed into contact with a second tissue, which in this case is the heart 90. The outer deflector is moving and holding the pericardium away from the heart to provide space between the two tissues for delivery and deployment of a medical device between the two tissues. As shown in FIG. 36, the medical device comprises a cardiac harness, as described in greater detail above. In the embodiment where a suction cup is used (see FIGS. 1 through 4), it may first be securely attached to the apex of the heart 90 by a partial vacuum as is described in detail above. The cardiac harness is then passed between the inner and outer deflectors as it is directed under the pericardium and onto the ventricular epicardium, as shown in FIG. 36.

After deployment of the cardiac harness, suction is released from the suction cup, and the delivery system 180 is slowly removed from the pericardial incision. The deflector compression sheath 182 is re-advanced distally during system removal in order to collapse both the inner 70 and outer 182 deflectors as shown in FIG. 34 and facilitate system removal.

Outer Deflector

Figure 37:
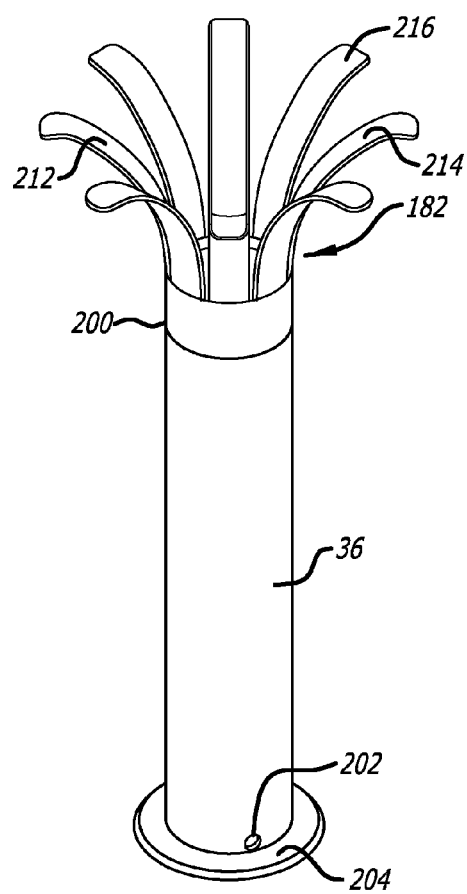
FIG. 37 is a perspective view of a housing with an outer deflector formed at its distal end and a flange formed at its proximal end, the outer deflector having a plurality of petals expanded outwardly in a deployed configuration, the petals being not tapered and not overlapping in this configuration.
Figure 38:
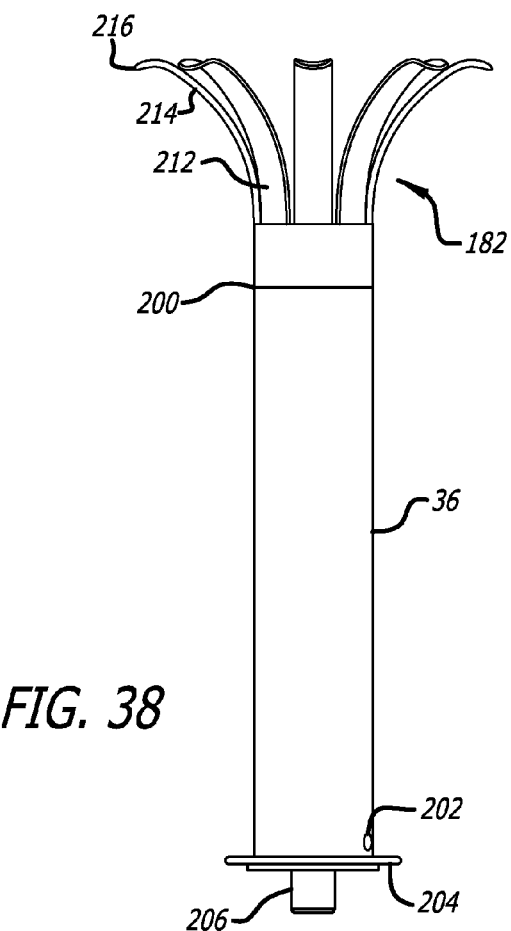
FIG. 38 is a side view of the housing and outer deflector of FIG. 37 showing at the proximal end of the housing a mounting sleeve through which a medical device or other devices forming a part of the delivery apparatus may be mounted into the housing.

Referring now to FIGS. 37 through 41, details of an embodiment of an outer deflector 182 are shown. In particular, FIGS. 37 and 38 present perspective and side views respectively of an outer deflector 182 formed to the distal end 200 of a housing 36. The housing also includes a proximal end 202 at which a flange 204 is formed. As is shown and discussed below, this flange 204 functions as a stop flange to limit the amount of movement of a deflector compression sheath in the proximal direction.

As also seen in all of FIGS. 37 through 41, the outer deflector 182 comprises a plurality of petals 212 or arms. The petals in this embodiment are not overlapping and are not tapered. However, they bend outwardly in their "at rest" position with the outward bend being generally trumpet shaped in this embodiment and including varying radii 214 near their distal ends 216. Although the drawing reference numerals point to only one arm, this is done for the purpose of clarity in the drawings. The numerals in this case are meant to refer to all petals.

Figure 39:
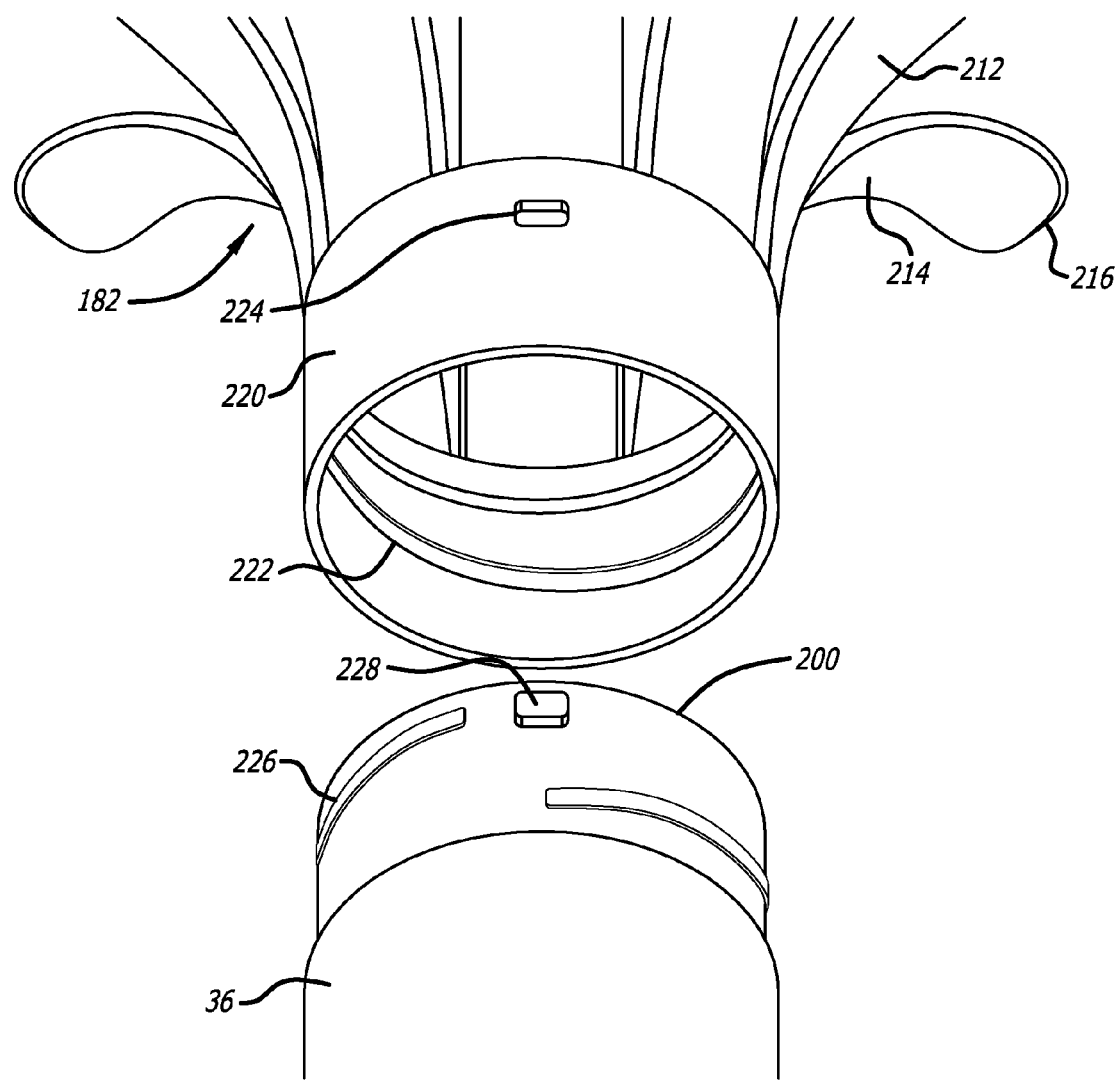
FIG. 39 presents a perspective view of the distal end of the housing on which a thread has been formed as well as a locking tab, and the proximal end of the outer deflector which comprises a ring having a thread complementary to that of the housing, and a locking tab aperture for receiving the locking tab of the housing during assembly of the two together.
Figure 40:
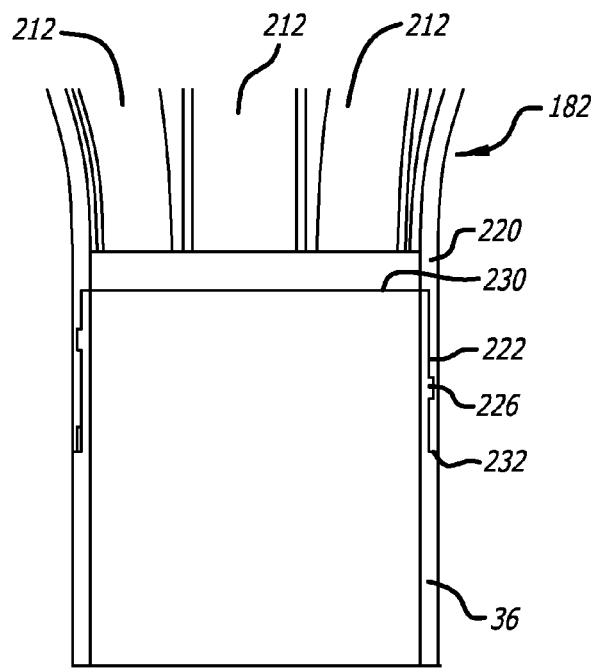
FIG. 40 is a cross section view of the ring and housing shown in FIG. 40 in the assembled configuration showing the threaded interconnection of the two.

Referring now to FIGS. 39 and 40, there is shown an outer deflector ring 220 to which all petals 212 are mounted. In this embodiment, the outer deflector ring 220 includes an internal thread 222 and a keyhole 224. The distal end of the housing 200 includes an outer thread 226 that is complementary to the internal thread 222 formed in the deflector ring 220. The distal end of the housing also includes an outer clocking tab 228 having a size such that it may be received by the keyhole 224 in the deflector ring 220 when the outer deflector 182 is assembled with the housing 36.

In this preferred configuration, the axial strength of the assembled components is derived primarily from the mechanical locking of their respective threads 222 and 226. In order to keep the assembled components from unscrewing during use, the keyhole 224 and tab 228 are designed into the thread, which snap together during the final degrees of rotation during assembly. In addition to the thread, adhesive could be used to further strengthen the bond between the components. One advantage of the threaded connection is that the outer deflector 182 petals 212 can be clocked relative to the housing 36. Since the housing contains the push rods 40 (see FIGS. 2-3), a rotational alignment between the outer deflector petals 212 and the push rods 40 can be achieved, if needed. This may be important in either shielding the implant sections (such as rows 98 of the harness 42) between the push rods from contacting the pericardium during implant advancement (such as avoiding the push rods moving between the petals) or keeping the push rod tips from catching on a retractor blade (push rods are in-line with the petals). In either case, it may be desirable to match the number of push rods to the number of outer deflector petals, thereby ensuring a homogenous angular distribution of push rods and petals.

FIG. 40 presents an assembled outer deflector 182 and housing 36 showing the mating of the respective threads of the two. Additionally, the location of the thread in each component and the thickness of the walls of each of the tubular wall of the housing and the ring 220 of the deflector are selected such that the inner and outer connection points 230 and 232 of the deflector 182 and housing 36 appear seamless. Although shown in FIG. 39 that the petals 212 are part of the single ring 220 and that the petals are spaced apart from each other, the ring and petal mounting approach may also take other forms. It may be similar or identical to that used with the inner deflector as described and shown in detail herein (see FIGS. 5, 6, and 7) where more petals in a separate interlocking ring or overlapping petals are selected for the outer deflector, or it may also take other forms.

Figure 41:
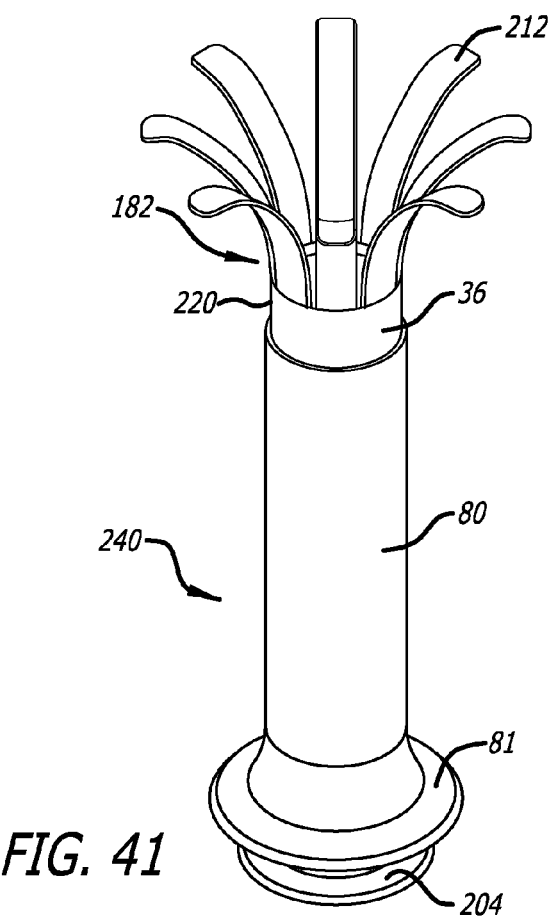
FIG. 41 shows a delivery system in accordance with aspects of the invention usable as both an introducer and delivery system, comprising a housing having a tubular wall with an outer deflector formed at the distal end of the tubular wall by means of a threaded mechanical connection, the outer deflector having a plurality of non-tapered petals having varying radii towards their distal ends and having varying thicknesses to control the outward flare, and additionally showing a deflector compression sheath slidably located on the housing in the deployed position so that the outer deflector is in the deployed configuration, the deflector compression sheath having a stop flange at its proximal end to engage the proximal end flange of the housing to control the range of sliding motion of the deflector compression sheath.

FIG. 41 shows the combination of the housing 36 and outer deflector 182 that is shown partially in FIG. 40 but with a deflector compression sheath 80 in place over the housing and located at the deployment position. The outer deflector 182 therefore is in the deployed configuration with the petals 212 bent outwardly in their at-rest configuration. The position of the sheath 80 may be controlled by the manipulation flange 81 located at its proximal end. The proximal housing flange 204 limits the proximal movement of the compression sheath in that the proximal housing flange is larger than the internal diameter of the deflector compression sheath and therefore, movement of the compression sheath in the proximal direction will eventually cause its contact with the proximal housing flange which will then stop its further proximal sliding movement. By grasping the manipulation flange 81 of the deflector sheath and moving it in the distal direction, the sheath may be moved to cover the outer deflector 182 and collapse the petals 212 into the delivery configuration for either moving the delivery system 30 through an incision and into position for delivery of a medical device, or for withdrawing the delivery system 30 from an incision. As discussed below in detail, when in this "delivery" configuration, the system is able to function as an introducer also.

Integrated Introducer

Figure 42:
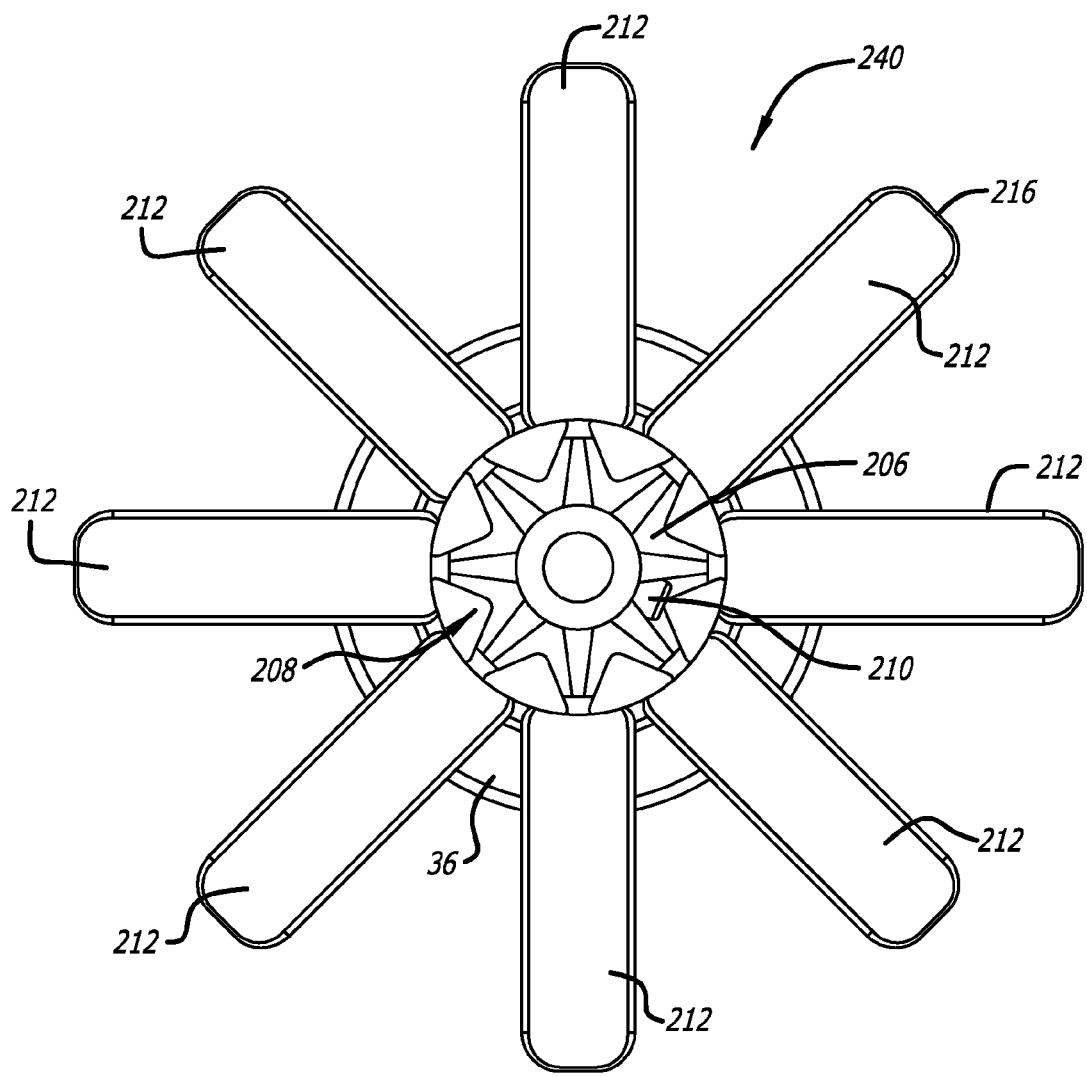
FIG. 42 is a top view of the configuration of FIGS. 37 and 38 showing the non-tapered form of the outer deflector petals and further showing the mounting sleeve and supporting web shown in FIG. 38.

The devices shown in FIGS. 37 through 41 may also function as an introducer in addition to functioning as a delivery system for delivering medical devices. In that regard, the device shown in FIG. 41 may be referred to as a medical device delivery system having an integrated introducer 240. In this embodiment, there is no inner deflector. Returning to FIG. 38, a mount flange 206 is located at the housing proximal end 202 through which a medical device may be mounted or guided for delivery to a patient. Such a medical device may comprise a suction tube 54 (see FIG. 1) for use with a distal suction device 52 (see FIG. 1). Another example may include delivery of a scope-type device. Referring also to FIG. 42, an end view is presented from the distal end of the integrated introducer 240 of FIG. 41 in which the mount flange 206 and its mounting webbing 208 can be seen. A set screw 210 is provided for securing a medical device in a fixed position in relation to the mounting flange 206 and the housing 36. More webbings or other internal structures may be formed or mounted within the housing 36 for assisting in delivering medical devices to a patient.

Figure 43:
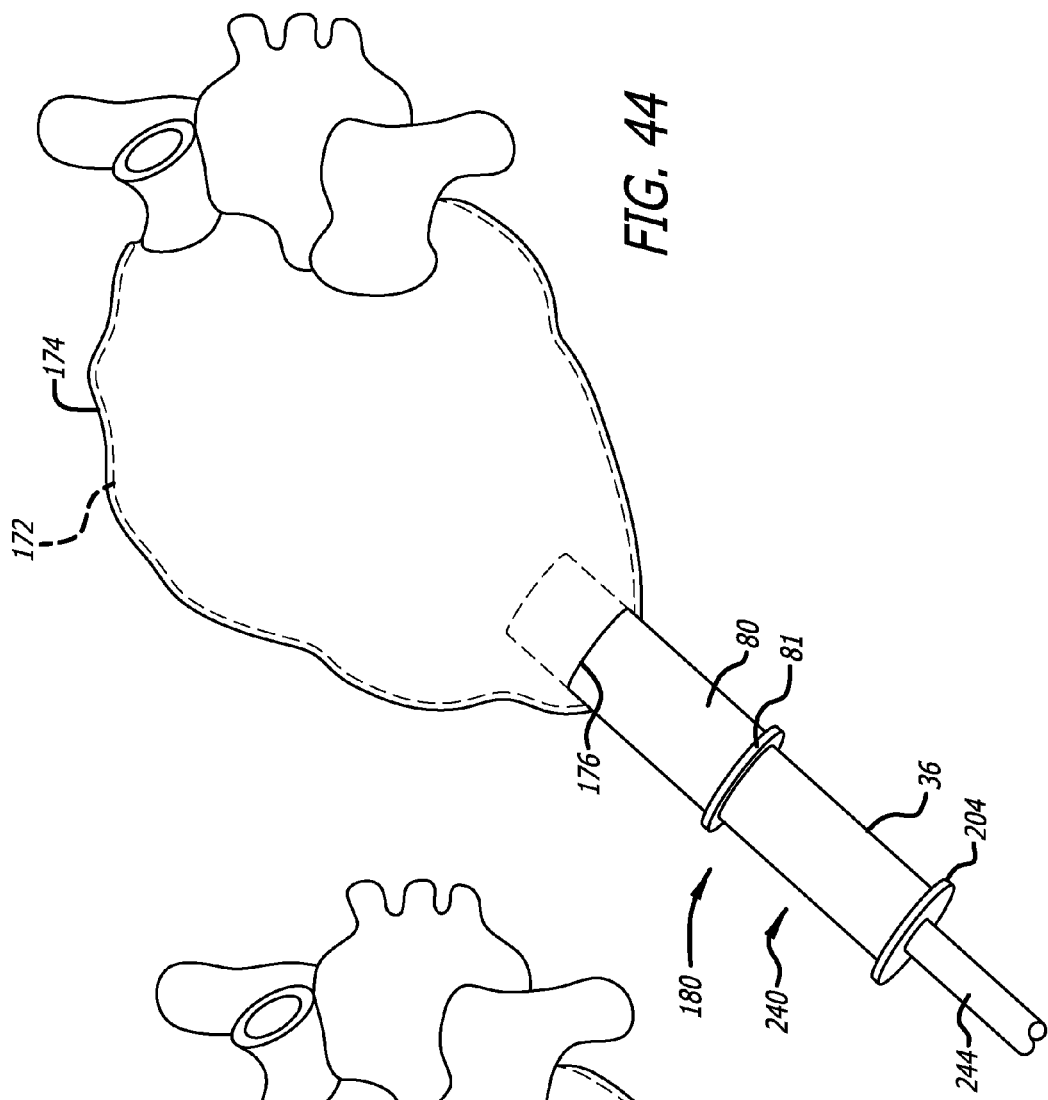
FIG. 43 is a view of the pericardium with an incision formed adjacent the apex of the heart, similar to FIG. 29, for receiving the integrated introducer/delivery system of FIG. 41.
Figure 44:
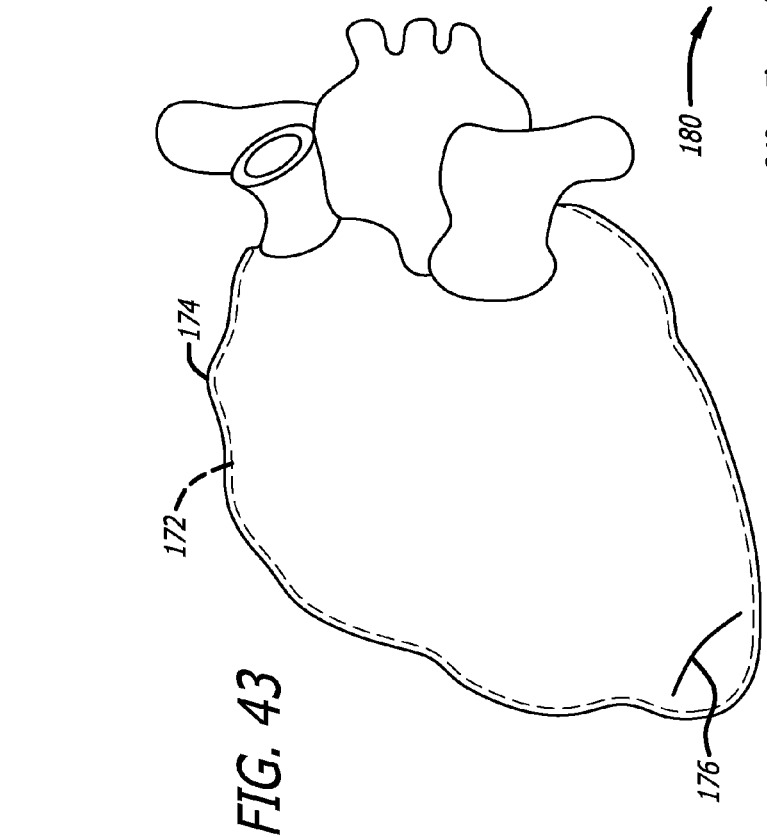
FIG. 44 shows the delivery system of FIG. 41 also functioning as an introducer that has been advanced through an incision in the pericardium surrounding a patient's heart, with the deflector sheath extended into the introducer configuration in which it has been extended over the entirety of the deflector to fully collapse the deflector within the sheath, the delivery system now being in position to fully release the deflector.

FIGS. 43 through 46 provide illustrations of the use of the medical device delivery system 180 with integrated introducer 240. FIG. 43 is similar to FIG. 29 in that it illustrates a human heart 172 that is enclosed within a pericardium 174. To permit introduction of a delivery device to a location within the pericardium 174, a small incision 176 is made in the pericardium adjacent the apex of the heart. With reference next to FIG. 44, the integrated introducer with medical delivery system 240 is shown being inserted through the incision. The figure is not drawn to scale so that clarity of illustration can be enhanced. In particular, the pericardium is shown at the incision but the heart is not shown. When the pericardium is tented with stay sutures, the introducer may be moved inwardly through the pericardium as much as is shown in FIG. 44. The deflector sheath 80 is shown in one embodiment of an introducer position in this figure having been moved distally to extend fully over and collapse the outer deflector resulting in an introducer configuration. The distal end of the medical device delivery system 180 with integrated introducer 240 is now in the configuration of an introducer and may be advanced through the incision 176 just as other introducers would have been, such as the introducer sleeve 162 shown in FIG. 30. In practice, one side of the distal end of the introducer 240 is inserted into the incision 176 first, followed by the remaining side. Once in the approximate position as shown in FIG. 44, the delivery system 180 is now in position to fully release the deflector. Once the deflector is deployed, the suction cup (not shown) would be attached to the apex of the heart as described above, the delivery system alignment checked, and then the delivery system could be used to deploy the medical device.

Figure 45:
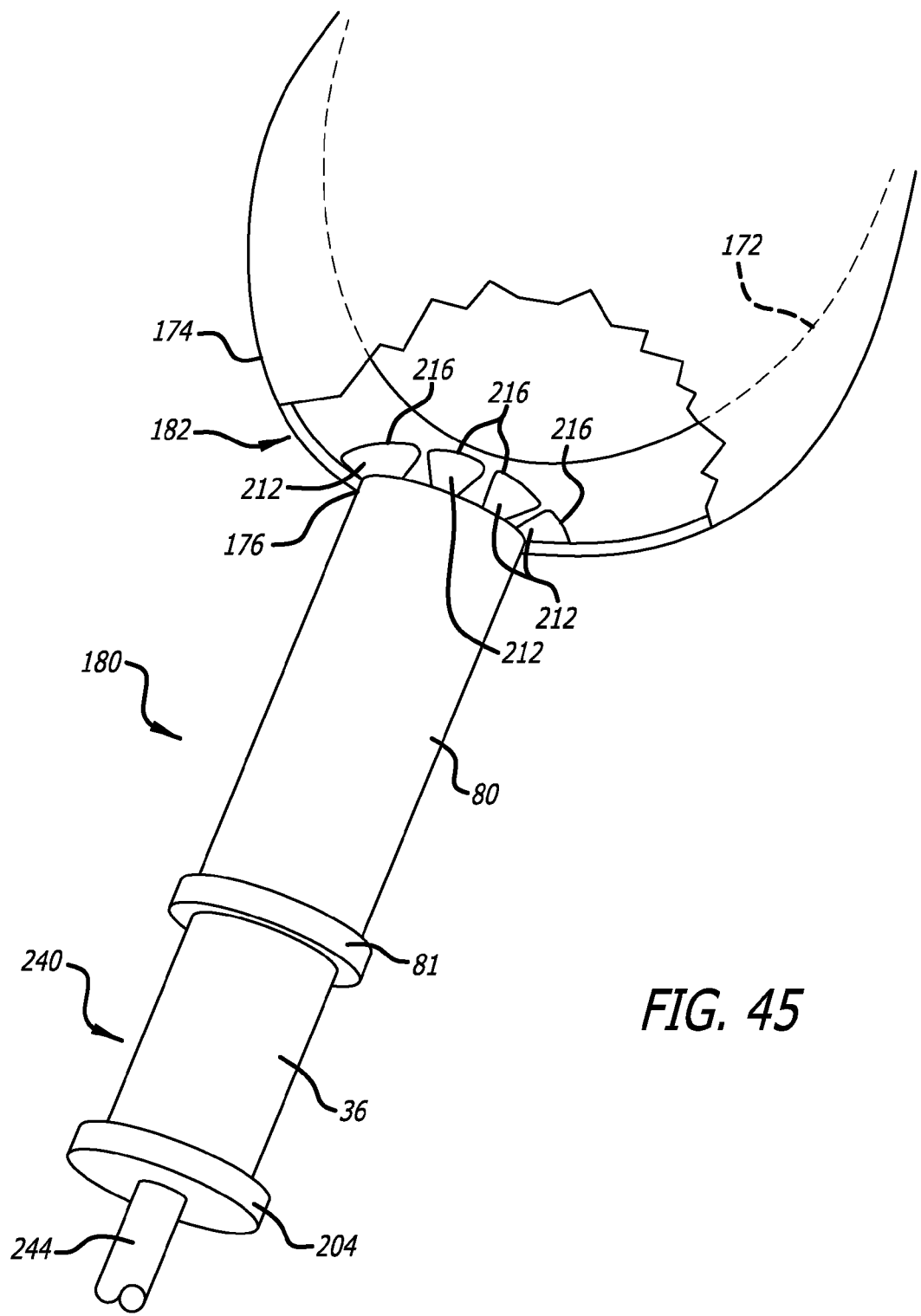
FIG. 45 presents a partially cutaway view of a second embodiment in which the deflector sheath has been extended over the deflector but does not cover the entirety of the deflector and instead, leaves the distal ends of the deflector uncollapsed, those distal ends deploying and flaring outwardly, in accordance with their relaxed shape, with those uncollapsed distal ends having been pushed through an incision in the pericardium and engaging the inner surface of the pericardium to secure the integrated introducer and delivery system within the pericardium to resist any pulling motion on the delivery system and retain it in the pericardium during retraction of the deflector sheath to fully release the deflector and prepare for delivery of a medical device disposed within the delivery system shown.
Figure 46:
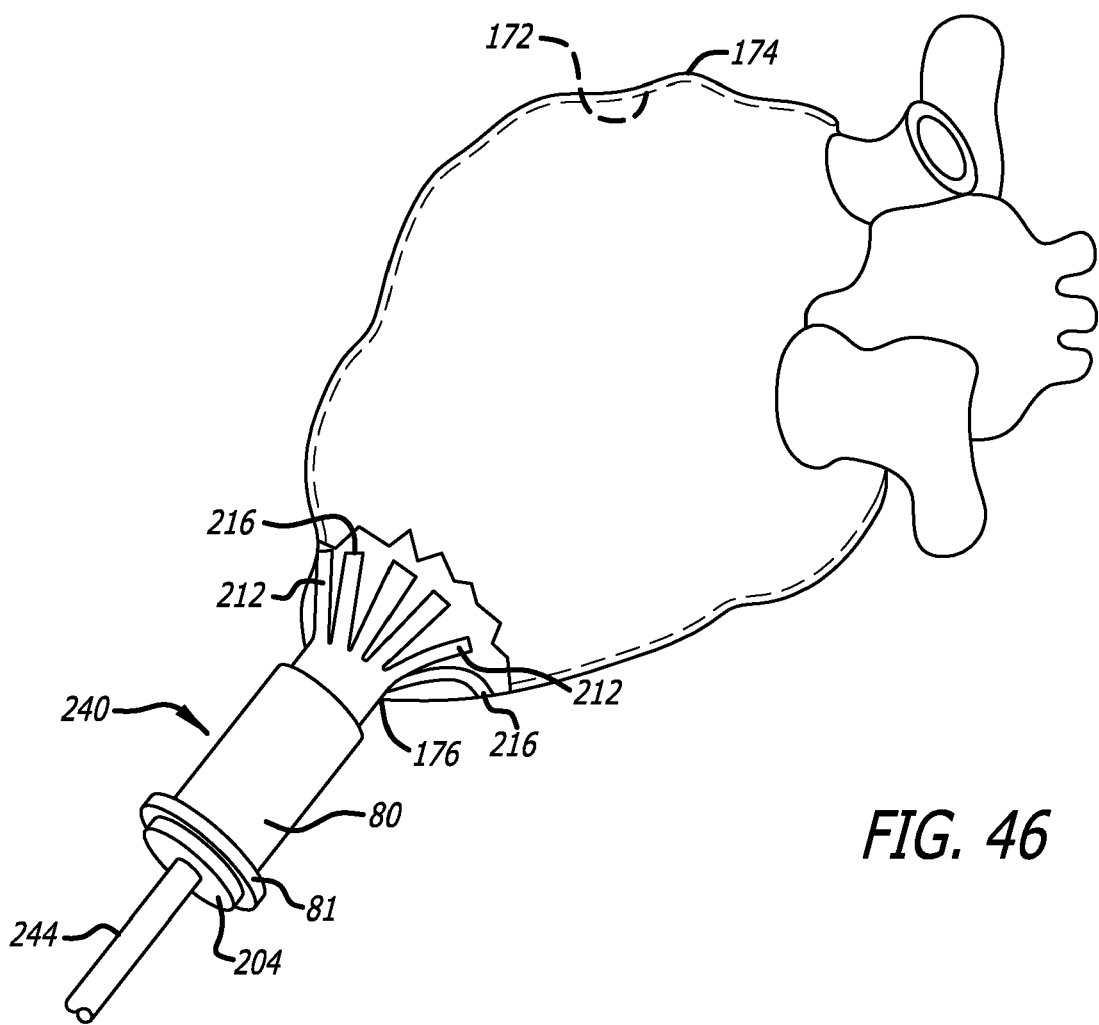
FIG. 46 is similar to FIG. 44 except that the integrated introducer and delivery device has now been placed into the deployed configuration in which the deflector sheath has been retracted by sliding it proximally to the deployed position and the deflectors have fully outwardly deployed into contact with the inner surface of the pericardium to hold it away from the heart so that the medical device can be delivered to the heart.

FIG. 45 presents a variation of FIG. 44 which has been found to be useful in securing the delivery system 180 within the pericardium 174 to avoid, or at least lessen, the chances of inadvertent removal of it therefrom as the mechanical motion of retracting the compression sleeve 80 is performed to fully deploy the outer deflector petals 212, as shown in FIG. 46. In the embodiment of FIG. 45, the deflector sheath 80 is moved in the distal direction, also referred to herein as being "extended," to collapse all but a distal portion or portions of the outer deflector 182. Those uncollapsed distal portions of the outer deflector flare outwardly from the distal end of the deflector sheath 80. The delivery system is then inserted through the incision 176 and the uncollapsed distal portions of the outer deflector engage the inside edge 194 of the pericardium 192 providing stability to the delivery device and securing it in position within the pericardium, similar to what was done in FIG. 31 with the flared portions 165 of the introducer sleeve 162. Then, should any pulling movement be applied inadvertently to the delivery device as the compression sheath is retracted, the engaged portions of the outer deflector will resist pulling the introducer out of the incision.

With reference next to FIG. 46, the deflector sheath 80 has now been retracted by being moved in the proximal direction to the deployed position which is far enough proximally to free the petals or arms 212 to assume their "at rest" outward bend or trumpet-shaped configuration in the deployed configuration. In this deployed configuration, the petals and in particular, their distal tips 216, are flared outwardly to a diameter greater than the diameter of the deflector sheath 80 and the housing 36 and preferably to a diameter greater than the size of the incision 176. As such, the flared portions or petals 212 press upon and open the incision 176 and the surrounding portion of the pericardium so as to create a space between at least part of the pericardium 174 and the heart 172. The portion of the pericardium over the delivery system has been cut away in the figure so that its operation within the pericardium can be seen. Further, the flared petals 212 function as a lock to resist pulling the introducer 240 out of the incision 176. Accordingly, the medical device delivery system with integrated introducer 240 is effectively locked in place between the heart 172 and the pericardium 174.

Since the outwardly bending petals 212 pull the pericardium 174 away from the heart 172, an access pathway is created to allow the medical device 244 that is mounted within the delivery system with integrated introducer 240 to be advanced through the housing 36, through the petals 212, and through the pericardium 174 to deliver the medical device, in this case, to the heart 172. When the medical procedure is completed, the medical device 244 is retracted through the housing 36, or left in place as the case may be, the deflector sheath 80 is extended distally over the deflector petals 212 to collapse them into the introducer configuration, as shown in FIG. 44, and the medical delivery system with integrated introducer 240 is withdrawn from the incision.

Figure 30:
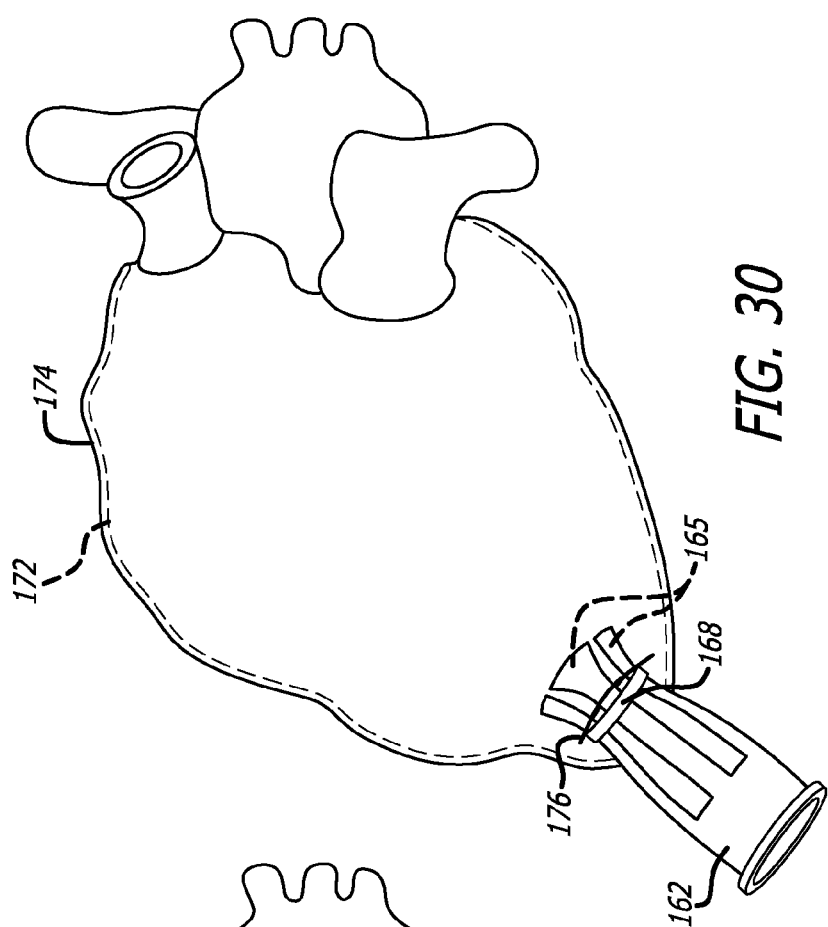
FIG. 30 shows the use of the introducer of FIG. 27 with its strips and flared portions collapsed for use in entry into the pericardium through the incision of FIG. 29.
Figure 29:
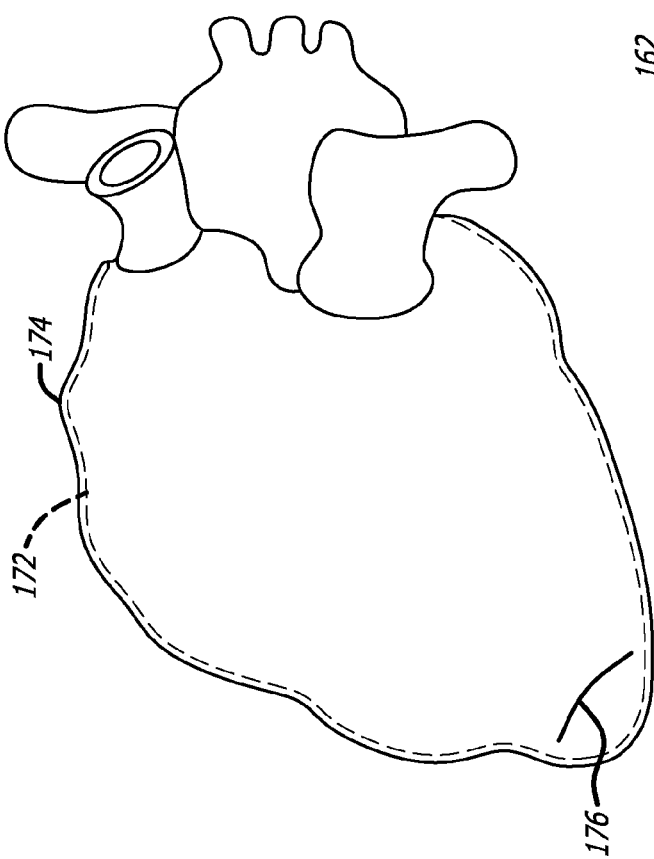
FIG. 29 is a view of the pericardium with an incision formed adjacent the apex of the heart.

Therefore, a medical device delivery system in accordance with the above has obviated the need for a separate introducer device. Neither a separate introducer sleeve 162 (FIG. 27) nor introducer dilator 164 (also FIG. 27) is needed. Instead of having to first locate the introducer in position as shown in FIG. 30 and then assemble the medical device to be delivered with the introducer as show in FIG. 31, the delivery system with integrated introducer 240 in accordance with aspects of the invention already has the medical device 244 to be delivered in position since the outer deflector 220 and deflector sheath 80 are part of the delivery system. This results in a smaller medical device delivery system, fewer manipulations in its use with a resulting associated decrease in trauma to the patient, fewer devices to keep in inventory, and an increase in efficiency. Although shown for use with the pericardium and the heart, other applications are possible.

Although the present invention has been described in the context of a preferred embodiment, it is not intended to limit the invention to the embodiment described. Accordingly, modifications may be made to the disclosed embodiment without departing from the spirit and scope of the invention. It is also contemplated that various combinations or subcombinations of the specific features and aspects of the embodiments can be combined with or substituted for one another in order to form varying modes of the invention. Accordingly, the invention is intended to be defined only by the claims that follow.

We claim:

1. An apparatus for delivering a cardiac harness onto a heart, comprising:

an elongate body having a proximal portion and a distal portion, the distal portion having a tubular housing sized to contain the cardiac harness in a compacted configuration, the tubular housing having a proximal end, an open distal end, an inner surface, and an outer surface;

a plurality of elongate push rods longitudinally movable with respect to the elongate body, the cardiac harness releasably connected to each of the push rods such that advancement of the push rods in a distal direction moves the cardiac harness from the compacted configuration in the housing to an expanded configuration outside the housing;

an outer deflector having a distal end and a proximal end, the outer deflector being flexible and configured so that it can be collapsed into a delivery configuration, and can be flared radially outwardly to a deployed configuration at which it has a first diameter at its distal end;

an inner deflector having a distal end and a proximal end, the inner deflector being flexible and configured so that it can be collapsed into a delivery configuration, and can be flared radially outwardly to a deployed configuration at which it has a second diameter at its distal end;

a deflector sheath slidably mounted over the outer surface of the tubular housing and having a delivery position at which the sheath retains the outer and inner deflectors in a collapsed, delivery configuration; and the deflector sheath being further slidably mounted over the outer surface of the tubular housing to a deployment position at which the outer and inner deflectors flare radially outwardly in deployed configurations so that the outer deflector engages the pericardium and the push rods and cardiac harness slide under the outer deflector and over the inner deflector as the harness slides over the heart.

2. The apparatus for delivering a cardiac harness of claim 1, wherein the inner deflector comprises a plurality of petals, the plurality of petals being configured to be collapsed into the deflector sheath in a delivery configuration and flared radially outwardly in a deployed configuration at which the petals have a second diameter at a distal end, the second diameter being smaller than the first diameter of the outer deflector.

3. The apparatus of claim 1, wherein the plurality of petals number in the range from four to twenty petals.

4. The apparatus of claim 2, wherein the petals are formed from a polymer material.

5. The apparatus of claim 4, wherein the polymer material is taken from the group of polymers including polyamides, polyamide copolymers such as PEBAX, silicone rubber, polyurethanes, and nylons.

6. The apparatus of claim 2, wherein the proximal ends of the petals are biased radially outwardly to form a flared configuration.

7. The apparatus of claim 1, wherein the housing has a substantially circular cross-sectional shape having a diameter, and wherein at least a portion of the housing is compressible to a substantially elliptical cross-sectional shape having a minor axis that is less than the diameter.

8. The apparatus of claim 1, wherein the housing has a cross-sectional shape having a first perimeter, and wherein at least a portion of the housing is compressible to a reduced cross-sectional shape having a second perimeter that is less than the first perimeter.

9. The apparatus of claim 1, wherein the cross-sectional shape is adapted for advancing through a minimally invasive surgical entry path.

10. The apparatus of claim 1, wherein the housing tapers from a first cross-sectional shape having a first perimeter at the proximal end of the housing to a second cross-sectional shape having a second perimeter at the distal end of the housing, the second perimeter being smaller in size than the first perimeter.

11. A method of delivering a cardiac harness onto a heart, comprising:
 advancing an elongated delivery device through a minimally invasive access site;
 deploying an outer deflector from the delivery device to engage the pericardium and open a space between the pericardium and the heart;
 deploying an inner deflector from the delivery device to engage the heart;
 advancing a cardiac harness out of the delivery device under the outer deflector and over the inner deflector;
 flaring the cardiac harness outwardly over the inner deflector and onto the heart; and
 withdrawing the delivery device with the inner and outer deflectors through the access site.

12. The method of claim 11, further comprising:
 extending a suction cup from a distal end of the delivery device;
 engaging the heart with the extended suction cup; and
 applying a vacuum to the suction cup to firmly attach the cup onto the heart.

13. The method of claim 12, wherein the inner deflector extends over the suction cup.

14. The method of claim 11, wherein the step of expanding the inner deflector to engage the heart further comprises guiding delivery of the harness onto the heart with the second deflector.

15. The method of claim 11, wherein the step of expanding the inner deflector out of the delivery housing to engage the heart further comprises protecting the heart with the second deflector during delivery of the medical device.

\* \* \* \* \*